United States Patent [19]
Perkins et al.

[11] Patent Number: 5,837,528
[45] Date of Patent: Nov. 17, 1998

[54] BACTERIAL STRAINS WHICH OVERPRODUCE RIBOFLAVIN

[75] Inventors: John B. Perkins, Reading; Alan Sloma, Watertown; Janice G. Pero, Lexington, all of Mass.

[73] Assignee: Hoffmann La Roche, Inc., Nutley, N.J.

[21] Appl. No.: 384,626

[22] Filed: Feb. 6, 1995

Related U.S. Application Data

[63] Continuation of Ser. No. 873,572, Apr. 21, 1992, abandoned, which is a continuation of Ser. No. 581,048, Sep. 11, 1990, abandoned, which is a continuation-in-part of Ser. No. 370,378, Jun. 22, 1989, abandoned.

[51] Int. Cl.$^6$ .............................. C12N 1/21; C12N 15/31; C12N 15/52
[52] U.S. Cl. ................ 435/252.31; 435/66; 435/69.1; 435/71.1; 435/71.2; 435/252.3; 536/23.2; 536/23.7
[58] Field of Search ................ 435/69.1, 71.1, 435/71.2, 172.3, 252.3, 252.32, 252.31, 252.33, 320.1, 66; 536/23.2, 23.7

[56] References Cited

U.S. PATENT DOCUMENTS

| | | | |
|---|---|---|---|
| 3,900,368 | 8/1975 | Enei et al. | 435/66 |
| 4,783,405 | 11/1988 | Kovacevic | 435/69.1 |
| 4,794,081 | 12/1988 | Kawai et al. | 435/66 |

FOREIGN PATENT DOCUMENTS 2546907  12/1984  France .

OTHER PUBLICATIONS

Chemical abstracts, 97:214, 1982.
Gloeckler et al., *Gene* 87:63–70 (1990).
Panina et al., Chem Abstract, vol. 98, No. 15, p. 177, Abstract No. 120613X.
Windholz et al., eds., Merck & Co., p. 8099, 1983.
Matsui et al., Agric. Biol. Chem. 46:2003, 1982.
Rabinovich et al., Genetika 14:1696, 1978 (with accompanying English translation).
Chikindas et al., Mol. Genet. Mik. Virusol. No. 2:20, 1987.
Morozov et al., Mol. Genet. Mik. Virusol. No. 7:42, 1984 (with accompanying English translation).
Morozov et al., Mol. Genet. Mik. Virusol. No. 11:11, 1984 (with accompanying English translation).
Morozov et al., Mol. Genet. Mik. Virusol. No. 12:14, 1985 (with accompany English translation).
Chikindas et al., Mol. Genet. Mik. Virusol. No. 4:22, 1987 (with accompanying English translation).
Chikindas et al., 5 SSSR 298:997, 1988 (with accompanying English translation).
Okunev et al., Genetika 7:1061, 1984 (with accompany English translation).
Gryczan et al., J. Bact. 134:318–329, 1978.
Janniere et al., GENE 40:47–55, 1985.
Osina et al., FEBS Letters, 196:75, 1980.
Sloma et al., J. Bact. 170:5557, 1988.
Ludwig et al., Jr. Biol. Chem. 262:1016, 1987.
Mironov et al., Doki. Akad. Nauk. SSSR, 30:482, 1989.
Chikindas et al., Doki. Akad. Nauk. SSSR, 298:997, 1988.
Maley et al., J. Biol. Chem. 258:8290–8297, 1983.
Bacher et al., J. Biol. Chem. 255:632–637, 1980.
Henner et al., GENE 1235:169–177, 1984.
Zalkin et al., J. Biol. Chem. 263:1595–1598, 1988.
Ebbole et al., J. Biol. Chem. 262:8274–8287, 1987.
Shimotsu et al., J. Bact. 166:461–471, 1986.

(List continued on next page.)

*Primary Examiner*—Johnny F. Railey, II
*Attorney, Agent, or Firm*—Fish & Richardson P.C.

[57] ABSTRACT

Vectors and recombinant bacteria for overproducing riboflavin, in which nucleic acid overproducing riboflavin biosynthetic proteins is introduced in the chromosome of the host organism, e.g. at multiple sites and in multiple copies per site. A rib operon having at least five genes is used to make such recombinant bacteria.

43 Claims, 38 Drawing Sheets

OTHER PUBLICATIONS

Rabinovich et al., Chem. Abstracts 88:293, 1978.
Jomantis et al., Chem. Abstracts 97:214, 1982.
Panina et al., Chem. Abstracts 97:214, 1983.
Rabinovich et al., Chem. Abstracts 100:138, 194.
Okunev et al., Chem. Abstracts 101,;57, 1984.
Rabiovich et al., Chem. Abstracts 102:160, 1985.
Matsui et al., Agric. Biol. Chem. 43(8):1739, 1979.
Matsui et al., Agric. Biol. Chem. 43(2):393, 1979.
Dubnau, "The Molecular Biology of the Bacilli," vol. 1, *Bacillus subtilis,* ed. Academic Press, 1982.
Kallio et al., Appl. Microbiol. Biotechnol., 27: 64–71 (1987).
Lee et al., Mol. Gen. Genet., 180: 57–65 (1980).
Osburne et al., J. Gen. Microbiol., 132:565–568 (1986).
Yanish–Perron et al., Gene 33 :103–119 (1985).
Rodriguez et al. (Pub. 1988), Vectors: A Survey of Molecular Cloning Vectors and Their Uses. Butterworths. Stoneham MA., pp. 179–203.
Maniatis et al. Molecular Cloning. 1982, Cold Spring Harbor Laboratory, Cold Spring Harbor New York.
Wahl et al. 1987. Meth. in Enzymology, vol. 152: 399–407.

*Upstream from*
*ribP1*

```
    A    T
  G
    G·C
    C·G
    T·A
    T·A
    T·G
    C·G
    C·G
    A·T
    C·G
    T·A
    A·T
    C·T
    A·T
    A·T
~ AA·TG(T₅) ~
```

708    #742

$\Delta G = -20 \ kcal/mol$

*Within 5'*
*leader mRNA*

```
         T
      T  A    T
      T·A
      T·A
      T·A
      A·T
      A·T
      G·C
      C·G
      C·G
      C·G
      C·G
      G·C
~AAA·T(T₅) ~
```

1034    #1062

$\Delta G = -26 \ kcal/mol$

*At 3' end of*
*rib operon*

```
      G  A    T
    T    G·C
         T·A
         C·G
         G·T
         G·C
         A·T
         G·C
         A·T
         G·C
         A·T
~ TA·T(T₆) ~
```

5037    #5064

$\Delta G = -16.5 \ kcal/mol$

FIG. 9

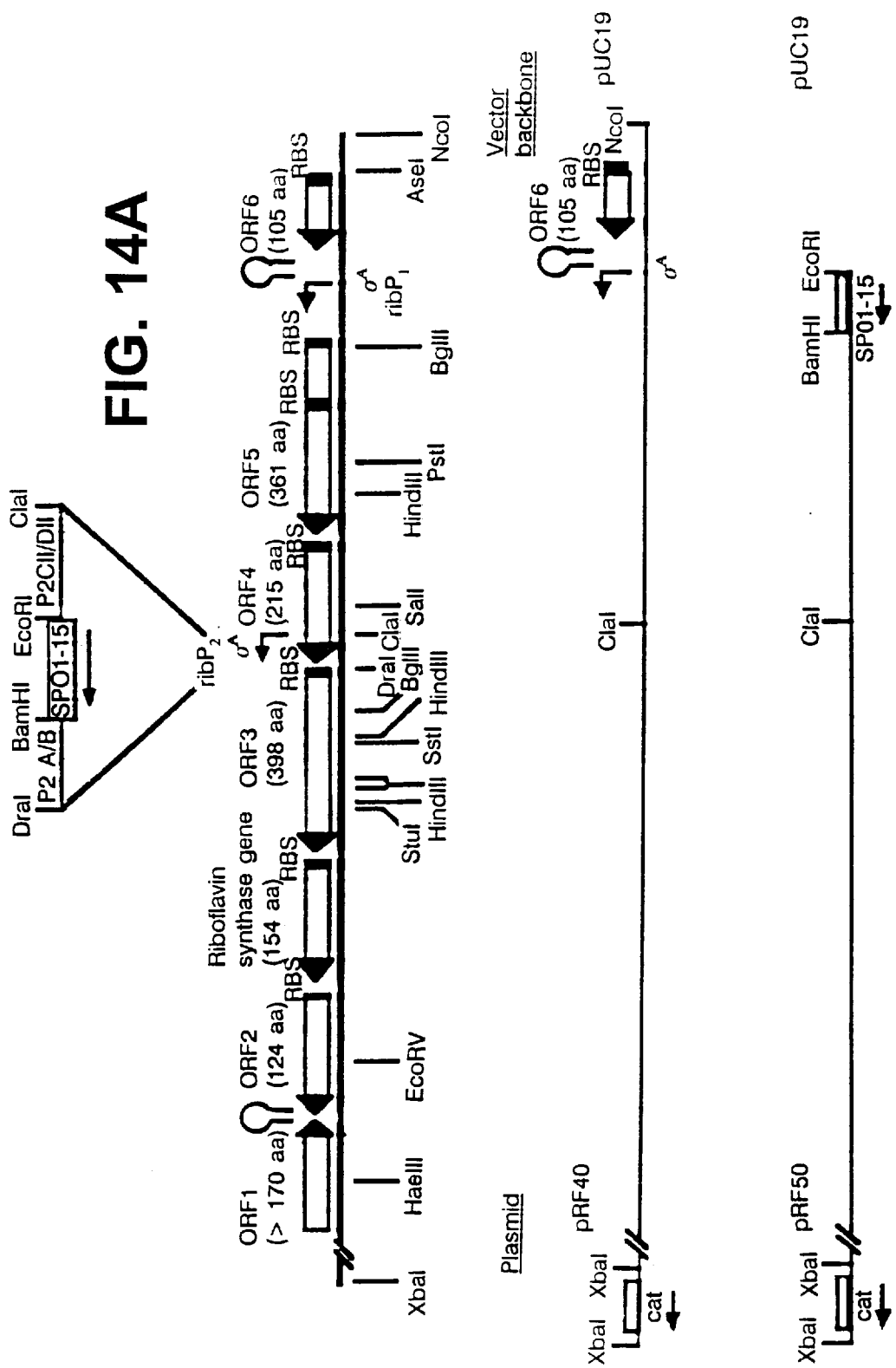

RB-5    AATTCATGCATGGATCCGACGGTAAATAAC
AAAAGAGGGGAGGGAAACAAATGGAAGAGT
ATTATATGAAGCTGGCCTTA

RB-6    GATCTAAGGCCAGCTTCATATAATACTCTT
CCATTTGTTTCCCTCCCCTCTTTTGTTATT
TACCGTCGGATCCATGCATG

P2-A    TCGACGGATCCTTTTAGAGAGGAAGATTTG
CATGTTTCATCCGATAGAAGAAGCACTGGA
CGCTTT

P2-B    AAAGCGTCCAGTGCTTCTTCTATCGGATGA
AACATGCAAATCTTCCTCTCTAAAAGGATC
CG

P2-CII  CGATTTTTGCATAAAGCCAATGAAAATAAG
ACCCAACAAACCATTACAAAAGCCTTCTTA
AGCGAAAACGGCTTTTAG

P2-DII  AATTCTAAAAGCCGTTTTCGCTTAAGAAGG
CTTTTGTAATGGTTTGTTGGGTCTTATTTT
CATTGGCTTTATGCAAAAAT

FIG. 18

BACTERIAL STRAINS WHICH OVERPRODUCE RIBOFLAVIN

This is a continuation of application Ser. No. 07/873,572, filed Apr. 21, 1992, now abandoned, which is a continuation of application Ser. No. 07/581,048, filed Sep. 11, 1990, now abandoned, which is a continuation-in-part application of U.S. Ser. No. 07/370,378, filed Jun. 22, 1989, now abandoned.

BACKGROUND OF THE INVENTION

Riboflavin (vitamin $B_2$) is synthesized by all plants and many microorganisms but is not produced by higher animals. Because it is a precursor to coenzymes such as flavin adenine dinucleotide and flavin mononucleotide, that are required in the enzymatic oxidation of carbohydrates, riboflavin is essential to basic metabolism. In higher animals, insufficient riboflavin can cause loss of hair, inflammation of the skin, vision deterioration, and growth failure.

Riboflavin can be commercially produced either by a complete chemical synthesis, starting with ribose, or by fermentation with the fungi *Eremothecium ashbyii* or *Ashbya gossypii* (*The Merck Index*, Windholz et al., eds., Merck & Co., p. 1183, 1983). Mutants of *Bacillus subtilis*, selected by exposure to the purine analogs azaguanine and azaxanthine, have been reported to produce riboflavin in recoverable amounts (U.S. Pat. No. 3,900,368, Enei et al., 1975). In general, exposure to purine or riboflavin analogs selects for deregulated mutants that exhibit increased riboflavin biosynthesis, because the mutations allow the microorganism to "compete out" the analog by increased production (Matsui et al., *Agric. Biol. Chem.* 46:2003, 1982). A purine-requiring mutant of *Saccharomyces cerevisiae* that produces riboflavin has also been reported (U.S. Pat. No. 4,794,081, Kawai et al., 1988). Rabinovich et al. (*Genetika* 14:1696 (1978)) report that the riboflavin operon (rib operon) of *B. subtilis* is contained within a 7 megadalton (Md) EcoRI fragment (later referred to as a 6.3 Md fragment in Chikindas et al., *Mol. Genet. Mik. Virusol.* no. 2:20 (1987)). It is reported that amplification of the rib operon may have been achieved in *E. coli* by cloning the operon into a plasmid that conferred resistance to ampicillin and exposing bacteria containing that plasmid to increasing amounts of the antibiotic. The only evidence for rib amplification is a coincident increase in the presence of a green-fluorescing substance in the medium; the authors present a number of alternative possibilities besides an actual amplification of the operon to explain the phenomenon observed.

French Patent Application No. 2,546,907, by Stepanov et al. (published Dec. 7, 1984), discloses a method for producing riboflavin that utilizes a mutant strain of *B. subtilis* which has been exposed to azaguanine and roseoflavin and that is transformed with a plasmid containing a copy of the rib operon.

Morozov et al. (*Mol. Genet. Mik. Virusol.* no. 7:42 (1984)) describe the mapping of the *B. subtilis* rib operon by assaying the ability of cloned *B. subtilis* rib fragments to complement *E. coli* riboflavin auxotrophs or to markerrescue *B. subtilis* riboflavin auxotrophs. Based on the known functions of the *E. coli* rib genes, the following model was proposed for the *B. subtilis* operon: ribG (encoding a deaminase) -ribO (the control element) -ribB (a synthetase) -ribF -ribA (a GTP-cyclohydrolase) -ribT/D (a reductase and an isomerase, respectively) -ribH (a synthetase).

Morozov et al. (*Mol. Genet. Mik. Virusol.* no. 11:11 (1984)) describe the use of plasmids containing the *B. subtilis* rib operon with either wild-type (ribO$^+$) or constitutive (ribO 335) operator regions to assay their ability to complement *B. subtilis* riboflavin auxotrophs. From the results, a revised model of the rib operon was proposed, with ribO now located upstream of all of the structural genes, including ribG, and with the existence of an additional operator hypothesized, possibly located just upstream of ribA.

Morozov et al. (*Mol. Genet. Mik. Virusol.* no. 12:14 (1985)) report that the *B. subtilis* rib operon contains a total of three different promoters (in addition to a fourth "promoter" that is only active in *E. coli*). The primary promoter of the operon was reported to be located within the ribO region, with the two secondary promoters reported between the ribB and ribF genes and within the region of the ribTD and ribH genes, respectively.

Chikindas et al. (*Mol. Genet. Mik. Virusol.* no. 2:20 (1987)) propose a restriction enzyme map for a 6.3 Md DNA fragment that contains the rib operon of *B. subtilis*. Sites are indicated for the enzymes EcoRI, PstI, SalI, EcoRV, PvuII and HindIII.

Chikindas et al. (*Mol. Genet. Mik. Virusol.* no. 4:22 (1987) report that all of the structural genes of the *B. subtilis* rib operon are located on a 2.8 Md BglII-HindIII fragment and that the BglII site is located between the primary promoter of the operon and the ribosomal-binding site of its first structural gene. As described infra, Applicants show that this BglII site is actually located within the most-5' open reading frame of the rib operon, so that the 2.8 Md fragment described does not contain all of the rib structural genes. Thus, in contrast to the report of Chikindas et al., the 1.3 Md BglII fragment does not contain the ribosomal-binding site of the first structural gene; insertions at this site lead to a riboflavin-negative phenotype. Consequently, any attempt to use this BglII site to engineer the rib operon in order to increase expression, for example by replacing the 5' regulatory region with a stronger promoter, would actually destroy the integrity of the first structural gene and thus the operon as well.

Chikindas et al. (*Dokl. Akad. Nauk. 5 SSSR* 298:997 (1988)) disclose another model of the *B. subtilis* rib operon, containing the primary promoter, $p_1$, and two minor promoters, $P_2$ and $p_3$: ribO($p_1$)-ribG-ribB-$p_2$-ribF-ribA-ribT-ribD-$p_3$-ribH. As before, it is incorrectly reported that the 1.3 Md BglII fragment contains the entire first structural gene of the operon and that this proximal BglII site maps within the primary regulatory region.

SUMMARY OF THE INVENTION

The present invention relates (inter alia) to recombinant bacteria useful in riboflavin production. The invention also involves the nucleotide sequence of the rib operon and its open reading frames, and recombinant bacteria that contain the rib operon. Additionally, the invention involves bacteria that have been mutated so that their production of riboflavin and/or purines is deregulated, and to bacteria which have copies of the rib operon inserted and amplified within their chromosomal DNA. In one embodiment, the rib operon itself can be deregulated by replacing its control regions with sequences that allow constitutive or unregulated expression. The bacteria, operons and sequences of this invention can be used to produce large amounts of riboflavin by fermentation. Finally, this invention involves the production of large quantities (over 10 g/l) of riboflavin by construction of various bacterial strains and growth of those bacterial strains within a medium and under conditions suitable for production of the riboflavin.

The present invention is illustrated by way of specific examples detailed below, one of which includes a mutant of B. subtilis 1A382, RB50::[pRF8]$_{60}$(Ade$^+$), that is deregulated for riboflavin and purine production and has the rib operon amplified within its chromosome. This mutant is able to produce greater than 5 g/l of riboflavin after 48 hours of fermentation in a 14-liter vessel. Other bacteria are described in which riboflavin production is increased to over 10 g/l under similar conditions.

The invention specifically includes the following aspects.

A first aspect of the invention features a recombinant bacterium which includes at least one copy of an exogenously introduced nucleic acid within its chromosome. This nucleic acid encodes one or more riboflavin biosynthetic proteins, is heritable, and is capable of expression by the bacterium such that riboflavin biosynthesis by the bacterium is increased relative to a bacterium lacking such a sequence.

By "recombinant bacterium" is meant a bacterium which contains one or more nucleic acid sequences, from the same or another organism, at a site at which those sequences do not naturally occur, or in a copy number in which they do not naturally occur. Thus, not only does the term include bacteria containing heterologous DNA sequences, it also includes those bacteria in which two copies of a nucleic acid sequence, e.g., a gene or an operon, are provided at a site which normally includes only one copy of the sequence; and it includes bacteria in which one or more copies of a nucleic acid sequence are introduced at a site which does not normally include that sequence. Such recombinant bacteria are constructed by standard recombinant DNA technology.

By "exogenously introduced" is meant that the nucleic acid is introduced into the chromosome from a source outside of that chromosome by any standard technique, including recombinant DNA technology, transformation, and transfection. It also includes the progeny of such bacteria, for example, those bacteria produced by cellular division of an originally constructed, transformed, or transfected bacterium.

By "riboflavin biosynthetic proteins" is meant to include those peptides, polypeptides or proteins which are directly involved in the synthesis of riboflavin from guanosine triphosphate. These proteins may be identical to those which naturally occur within a bacterium and are involved in the synthesis of riboflavin within that bacterium. Alternatively, they may be modifications of such proteins, for example, they may contain modifications which do not significantly affect the biological activity of the protein. For example, the natural protein may be modified by introducing or substituting one or more amino acids, preferably by conservative amino acid substitution, or by removing nonessential regions of the protein. Such modifications are readily performed by standard techniques.

In some embodiments, the bacterium contains two or more copies of the nucleic acid sequence; and the nucleic acid encoding one or more of the riboflavin biosynthetic proteins is present at at least two sites within the chromosome of the bacterium.

By "site" is meant a distinct chromosomal location relative to a wild-type bacterium at which the nucleic acid encoding the biosynthetic proteins is located. For example, such nucleic acid may be located at the naturally occurring site for genes encoding such proteins (i.e., at a rib locus), or it may be located at a site distant from this location. Preferably such distant sites are chosen from regions of chromosomal nucleic acid which are not essential to the recombinant bacterium, such as regions which encode proteins which are not essential to production of riboflavin. Examples of such regions include those which encode certain extracellular enzymes such as proteases. Insertion at such sites does not interfere with a desirable quality or trait. Any site is suitable as long as the functioning of the bacterium, with regard to riboflavin production, is not substantially affected.

In other embodiments, the nucleic acid is present in a plurality of copies at one or more of the sites; and the nucleic acid is present at at least three sites within the chromosome. By introducing the nucleic acid at different sites, the total number of copies of the nucleic acid within the chromosome can be increased. Increasing the copy number, increases the amount of riboflavin production.

Generally the riboflavin biosynthetic proteins are encoded by one or more rib genes (e.g., an inactivation of which creates a riboflavin auxotroph), preferably at least five distinct rib genes identifiable from the nucleotide sequence provided in FIG. 3. Preferably, at least five copies of such genes are provided. By "rib genes" is meant those genes or portions of genes which encode proteins which occur naturally within an organism, or perform a similar function to such proteins, which are involved in the biosynthetic conversion of guanosine triphosphate to riboflavin within a bacterium.

In a related aspect, the invention features a recombinant bacterium which includes nucleic acid encoding one or more riboflavin biosynthetic proteins, e.g., the gene products identified in FIG. 4, β subunit riboflavin synthetase gene, ORF's 2, 3, 4 and 5, the expression of at least one of which is controlled by a transcription element not naturally associated with the nucleic acid. Alternatively, the recombinant bacterium includes one or more rib genes or transcription units the expression of which is controlled by a transcription element not naturally associated with that rib gene.

By "transcription element" is meant to include any nucleic acid which effects (i.e., turns on) the transcription of nucleic acid downstream from that transcription element. Examples of such elements include promoters and operators. Such transcription elements are not naturally associated with the nucleic acid, for example, they may be heterologous transcription elements. That is, they may be isolated from other species or genera of bacteria or other organisms. Alternatively, the transcription element may be one naturally present in the bacterium but not normally associated with a rib gene to which it is now transcriptionally linked. Such elements do not include those which are naturally associated with a rib gene.

In other embodiments, the recombinant bacterium includes at least three (or at least five) rib genes and the expression of all three rib genes is controlled by a transcription element not naturally associated with those rib genes; at least two transcription elements are provided; the rib genes are provided within the chromosome of the recombinant bacterium; the recombinant bacterium is deregulated for riboflavin gene expression; and the transcription element is a promoter. For example, the promoter is a constitutive, growth-regulated, or inducible promoter, such as one associated with the SPO1 phage, and/or veg, amy, and sacQ-sensitive promoters, e.g., apr.

By "deregulated" is meant that the level of riboflavin production is greater than that observed in a bacterium with natural riboflavin regulatory systems (i.e., a wild type bacterium). Examples of such deregulated bacteria include those which are resistant to various purine analogs or antagonists, or riboflavin analogs.

In other specific embodiments, at least one of the rib genes includes a ribosome binding site not naturally associated with the rib gene; the rib genes are present at two sites within the chromosome; and the rib genes are present in a plurality of copies within the chromosome. In more preferred embodiments, the rib genes are Bacillus rib genes, for example ORF3 and ORF5 shown in FIG. 4, and the transcription element is located in a region 5'-upstream of ORF3 or ORF5; and the rib genes are chosen from a β-riboflavin synthase-encoding gene, ORF2, ORF3, ORF4, and ORF5; and the bacterium belongs to a species of Esherichia, e.g., E. coli, Bacillus, e.g., B. subtilis, Klebsiella, or Cornyebacterium.

In another related aspect, the invention features nucleic acid, which includes five or more rib genes, the expression of which is controlled by a transcription element not naturally associated with that rib gene.

In another aspect, the invention features a method for production of riboflavin. The method includes growing cells which are able to produce riboflavin under aerobic conditions with the level of dissolved oxygen maintained at a concentration between 5 and 30%. The method further includes limiting the growth of the cells by limiting the availability of a component in the growth medium such that the dissolved oxygen concentration is maintained at that level.

In this method the growth of cells is maintained at a level which prevents the growth conditions becoming anaerobic. Under anaerobic conditions the synthesis of riboflavin is reduced. In some embodiments, the limiting component is chosen from a carbon source, nitrogen source, or a component required by the cells (e.g., in the feed medium). For example, if the cells are auxotrophic, for example, for methionine, a limiting level of methionine may be provided in the growth medium. In another example, the limiting component is a carbon source such as glucose or a citric acid cycle acid. Exemplary citric acid cycle acids are citric acid or succinic acid.

In a related aspect, the invention features another method for increasing production of riboflavin by a bacterium. In this method, the strain of bacterium used is deregulated for riboflavin production. More than one copy of a nucleic sequence encoding one or more riboflavin biosynthetic proteins is introduced into the chromosomal DNA of this bacterium. Preferably the bacterium used in this method is selected from one of those described above.

In other aspects of the invention, purified nucleic acid and the recombinant polypeptide product of such nucleic acid is provided. Generally, the purified nucleic acid consists essentially of all or a portion of the rib operon, for example, the specific open reading frames shown in FIG. 3. Such purified nucleic acid may be provided within a vector such as a plasmid, phage, or cosmid, or may be integrated within the chromosome of a bacterium. This nucleic acid is separated from nucleic acid with which it is naturally linked. For example, 6.5 kb of the nucleic acid encoding the whole rib operon may be inserted within a Bacillus subtilis chromosome at a site distant from that site in which the 6.5 kb DNA is normally present. By recombinant polypeptide is meant biologically active protein free of extraneous polypeptide (i.e., not fused to a heterologous polypeptide) having an enzymatic activity equivalent to such a naturally produced polypeptide.

Other features and advantages of the invention will be apparent from the following description of the preferred embodiments thereof, and from the claims.

DESCRIPTION OF THE PREFERRED EMBODIMENTS

The drawings will first briefly be described.

Drawings

Figure 1:
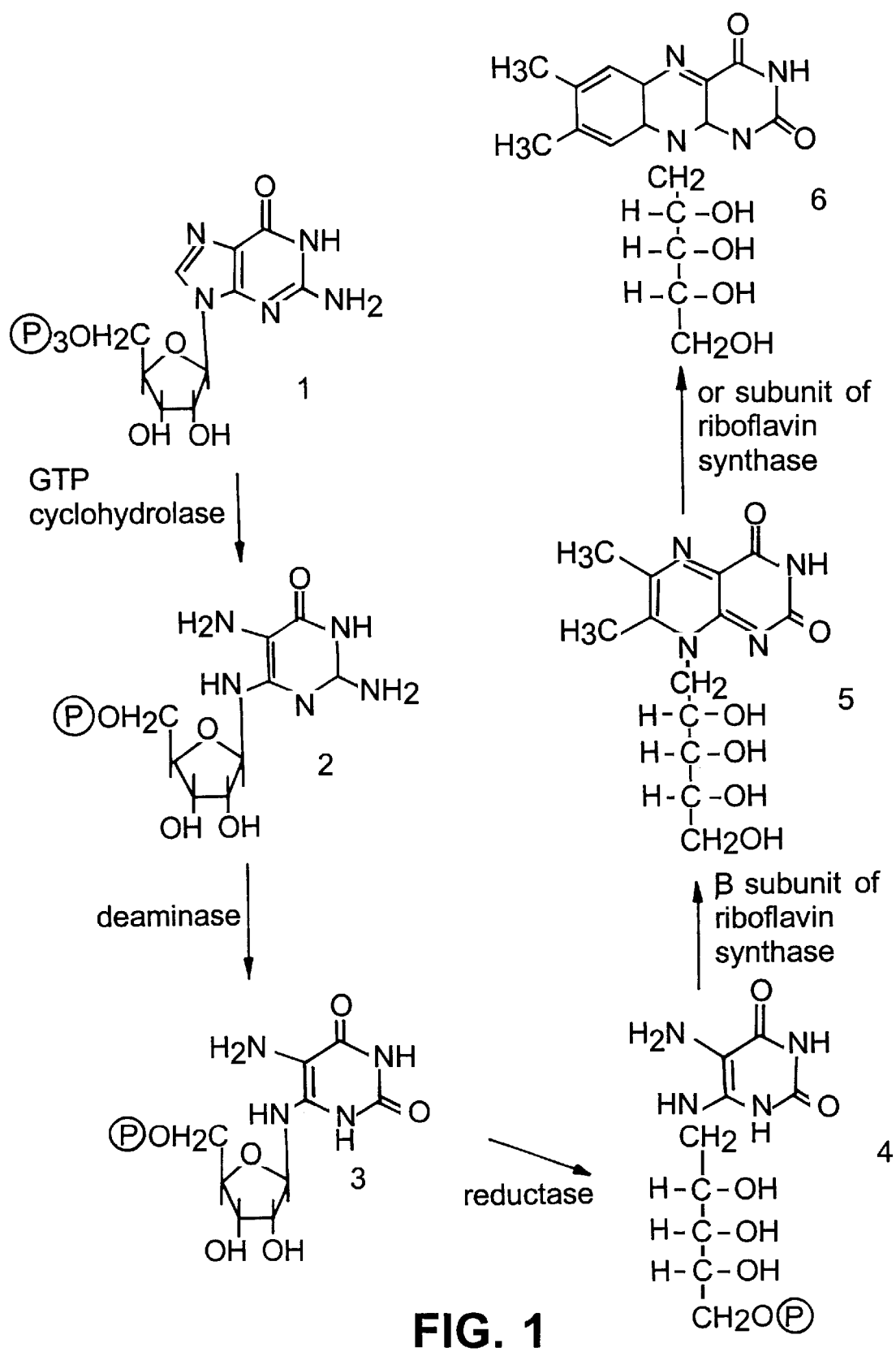

FIG. 1. The riboflavin biosynthetic pathway, modified from Keller et al., Biochem. 27:1117 (1988). The corresponding intermediates shown are those produced by E. coli (which are presumably the same as those produced by B. subtilis): structure 1, guanosine triphosphate (GTP); structure 2,2,5-diamino-6-(ribosylamino)-4(3H)-pyrimidinone-5'-phosphate; structure 3,5-amino-6-(ribosylamino)-2,4(1H, 3H)-pyrimidinedione-5'-phosphate; structure 4,5-amino-6-(ribitylamino)-2,4(1H,3H)-pyrimidinedione-5'-phosphate; structure 5,6,7-dimethyl-8-ribityllumazine; structure 6, riboflavin. The biosynthetic enzymes indicated are those encoded by B. subtilis (GTP cyclohydrolase, α and β subunits of riboflavin synthase) or those proposed to be encoded by B. subtilis (a rib-specific deaminase, and a rib-specific reductase).

Figure 2:
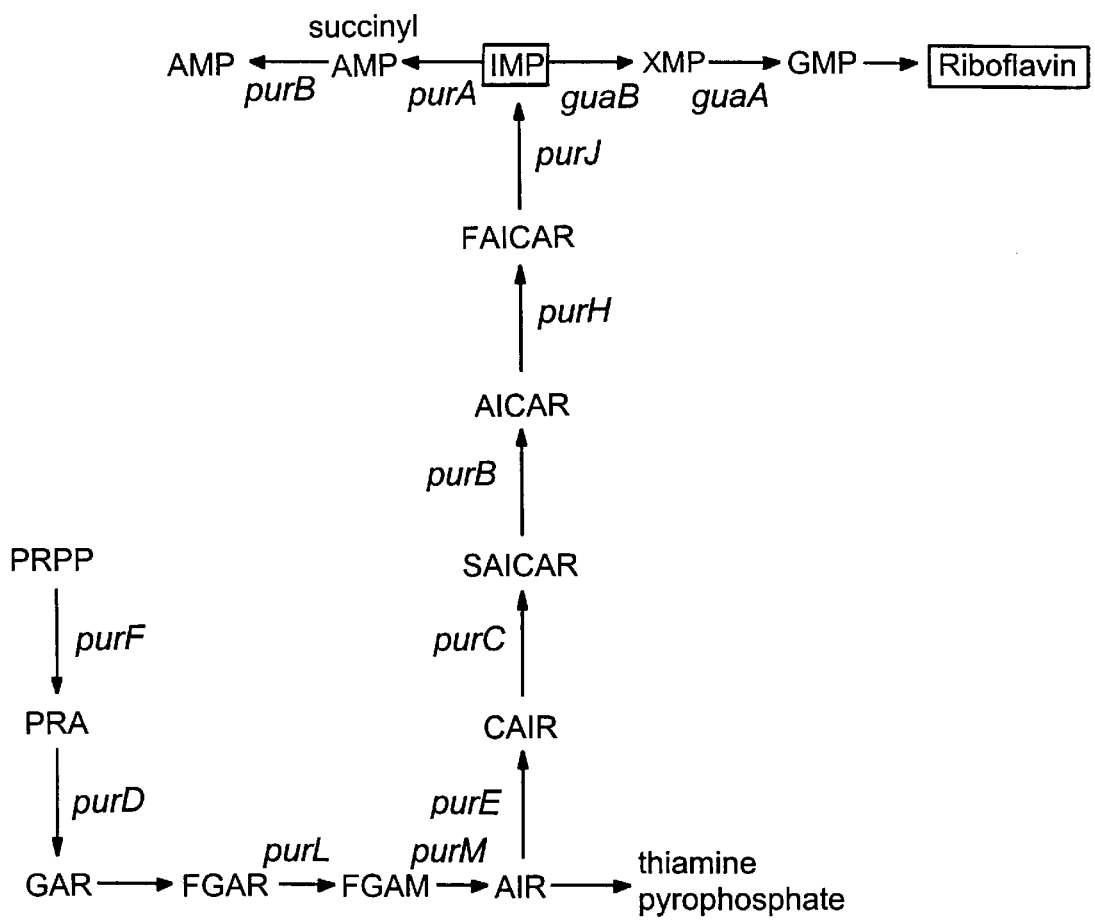

FIG. 2. Schematic representation of purine biosynthesis. The purine biosynthetic pathway, including the portion responsible for riboflavin biosynthesis, is depicted. The individual enzymes of the pathway are identified by their gene symbols (E. coli nomenclature). Abbreviations are as follows: PRPP, phosphoribosylpyrophosphate; GAR, glycinamide ribonucleotide; pur, GAR formyltransferase; PRA, phosphoribosylamine; purA, adenylosuccinate synthetase; purB, adenylosuccinate synthetase; FGAR, formylglycinamide ribonucleotide; SAICAR, aminoimidazolesuccinocarboxamide ribonucleotide; purc, SAICAR synthetase; FGAM, formylglycinamidine ribonucleotide; purD, GAR synthetase; AIR, aminoimidazole ribonucleotide; purE, AIR carboxylase; CAIR, carboxyaminoimidazole ribonucleotide; purF, PRPP amidotransferase; AICAR, aminoimidazolecarboxamide ribonucleotide; purH, AICAR formyltransferase; purJ, inosine monophosphate (IMP) cyclohydrolase; FAICAR, formamidoimidazolecarboxamide ribonucleotide; purL, FGAR amidotransferase: guaA, guanosine monophosphate (GMP) synthetase; purM, AIR synthetase; guaB, IMP dehydrogenase.

Figure 3A:
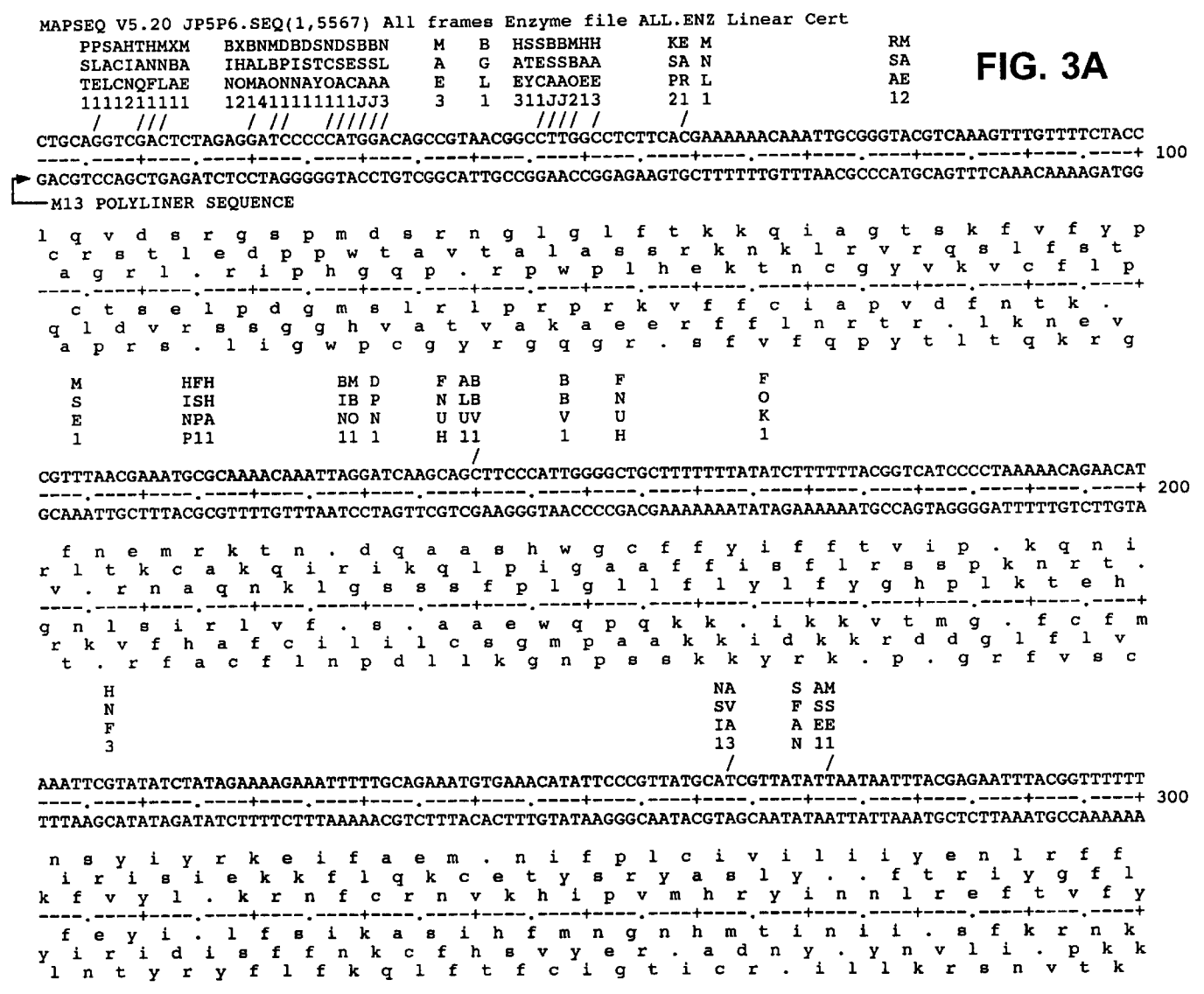
Figure 3B:
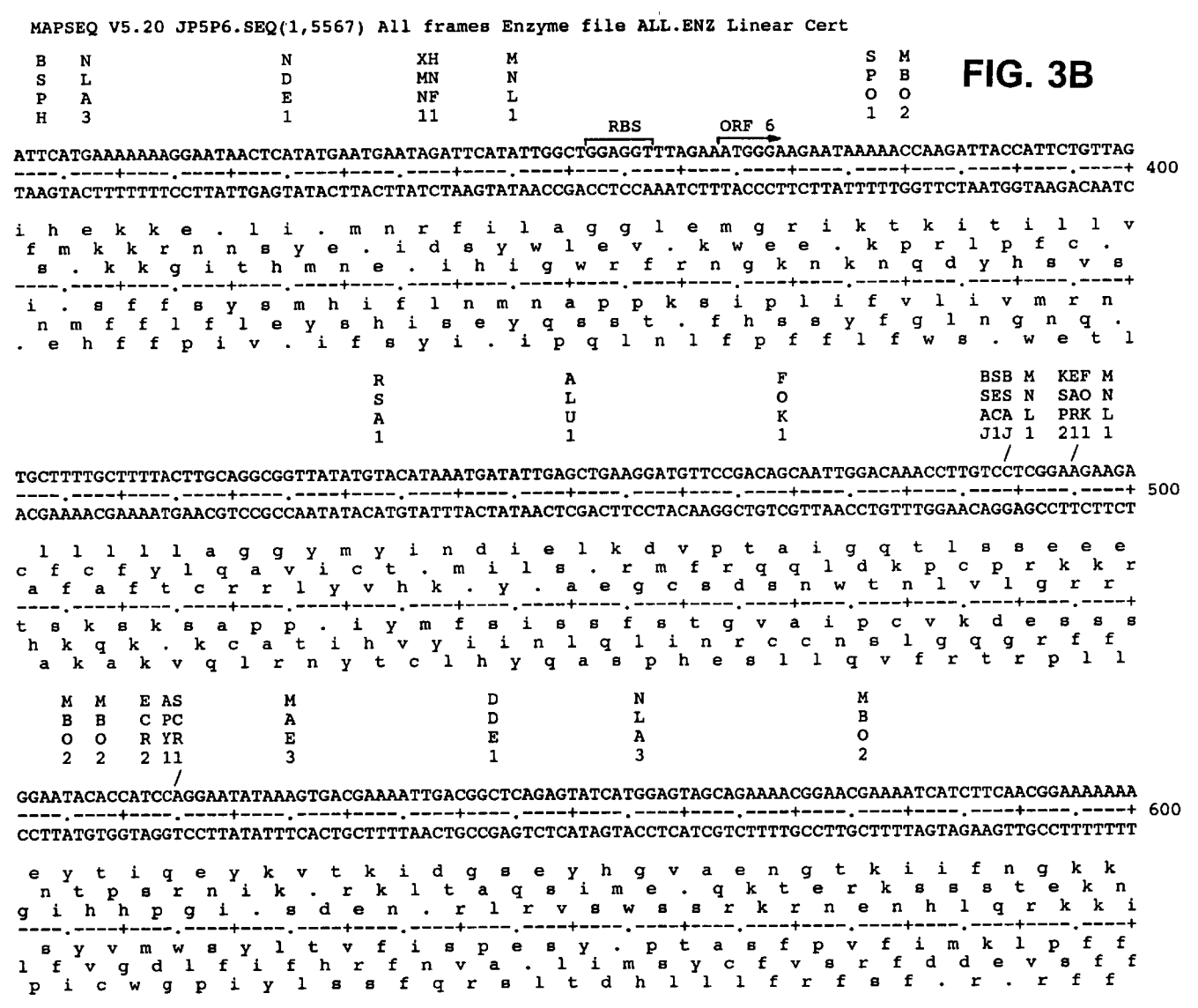
Figure 3C:
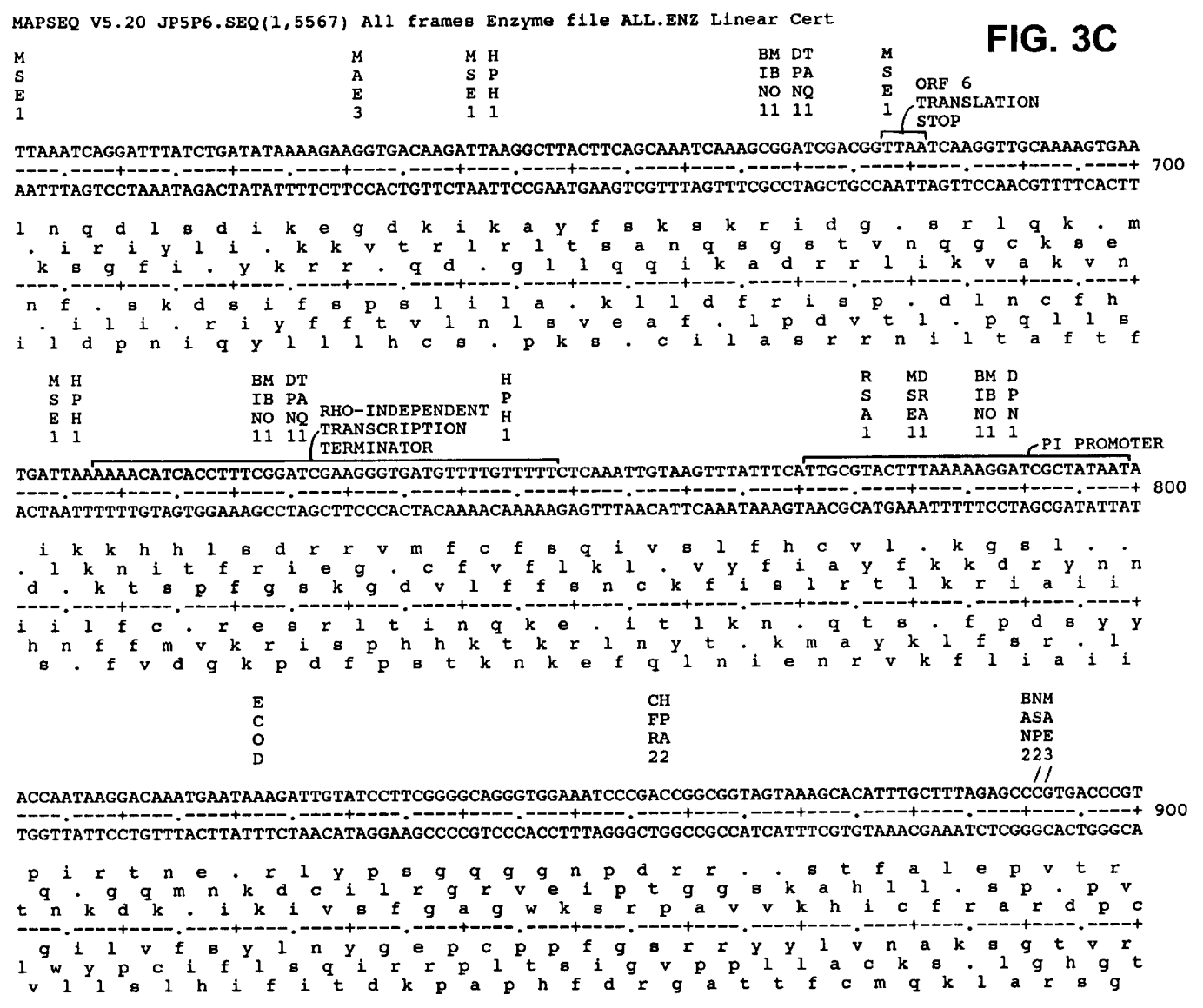
Figure 3D:
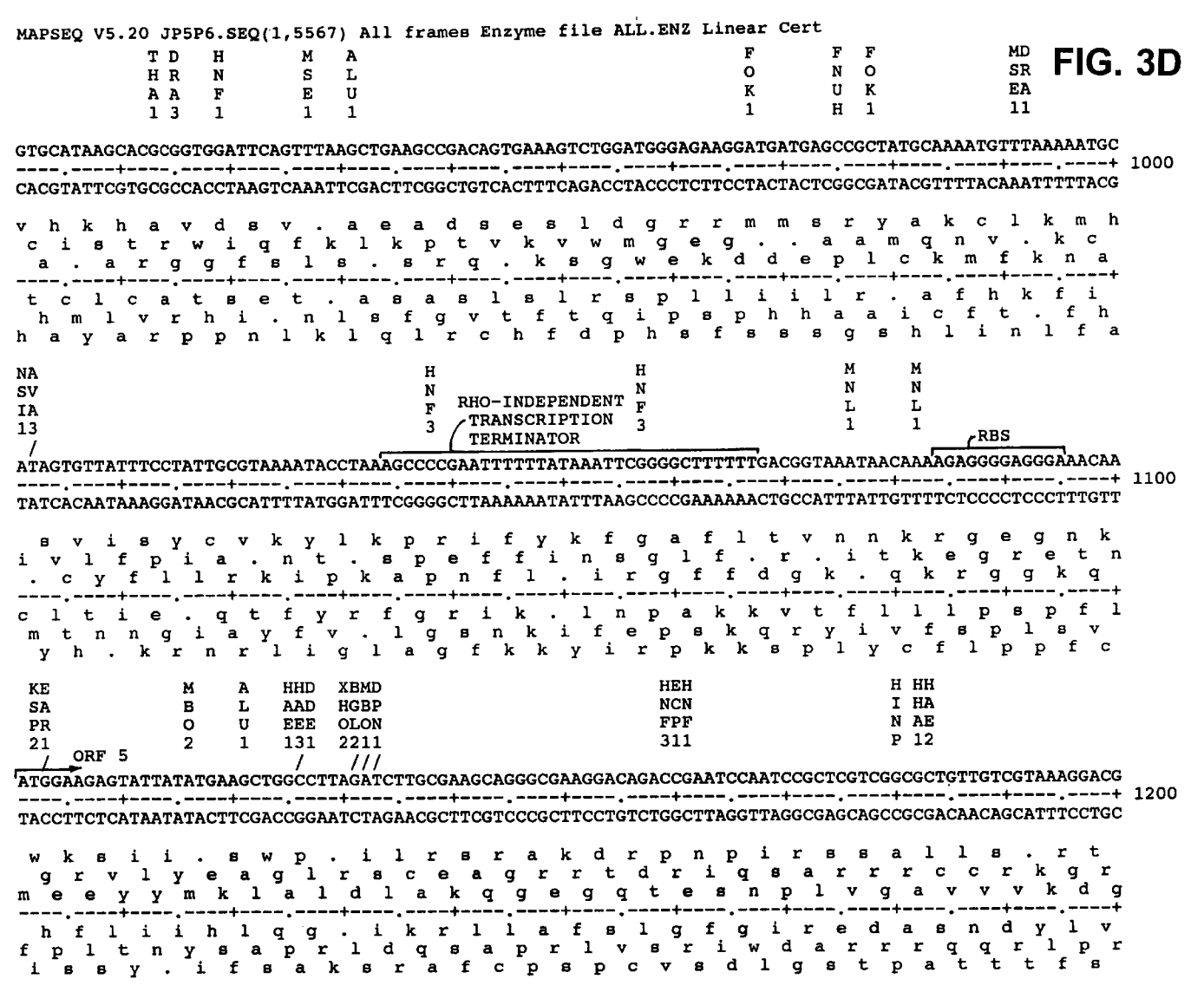
Figure 3E:
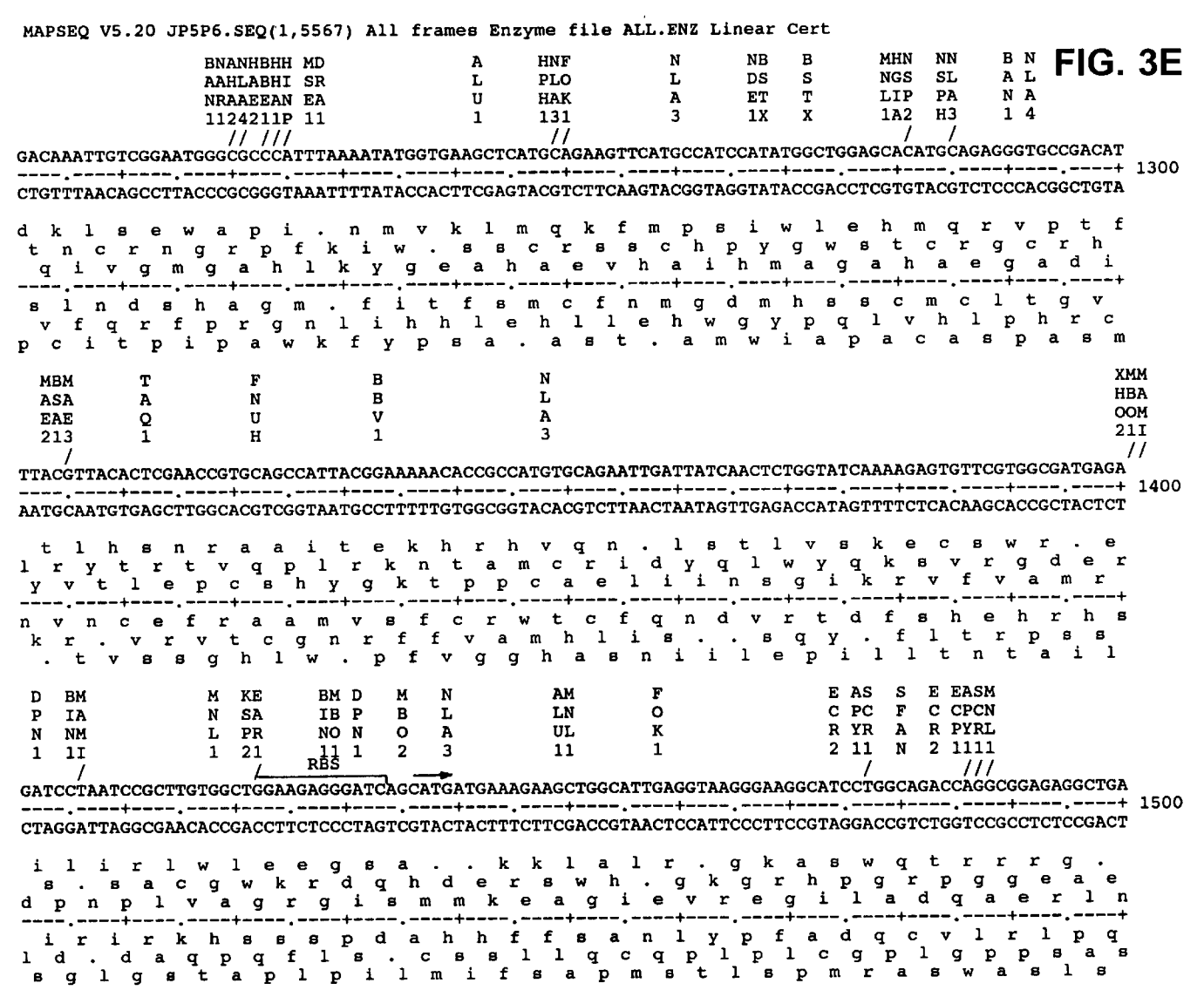
Figure 3F:
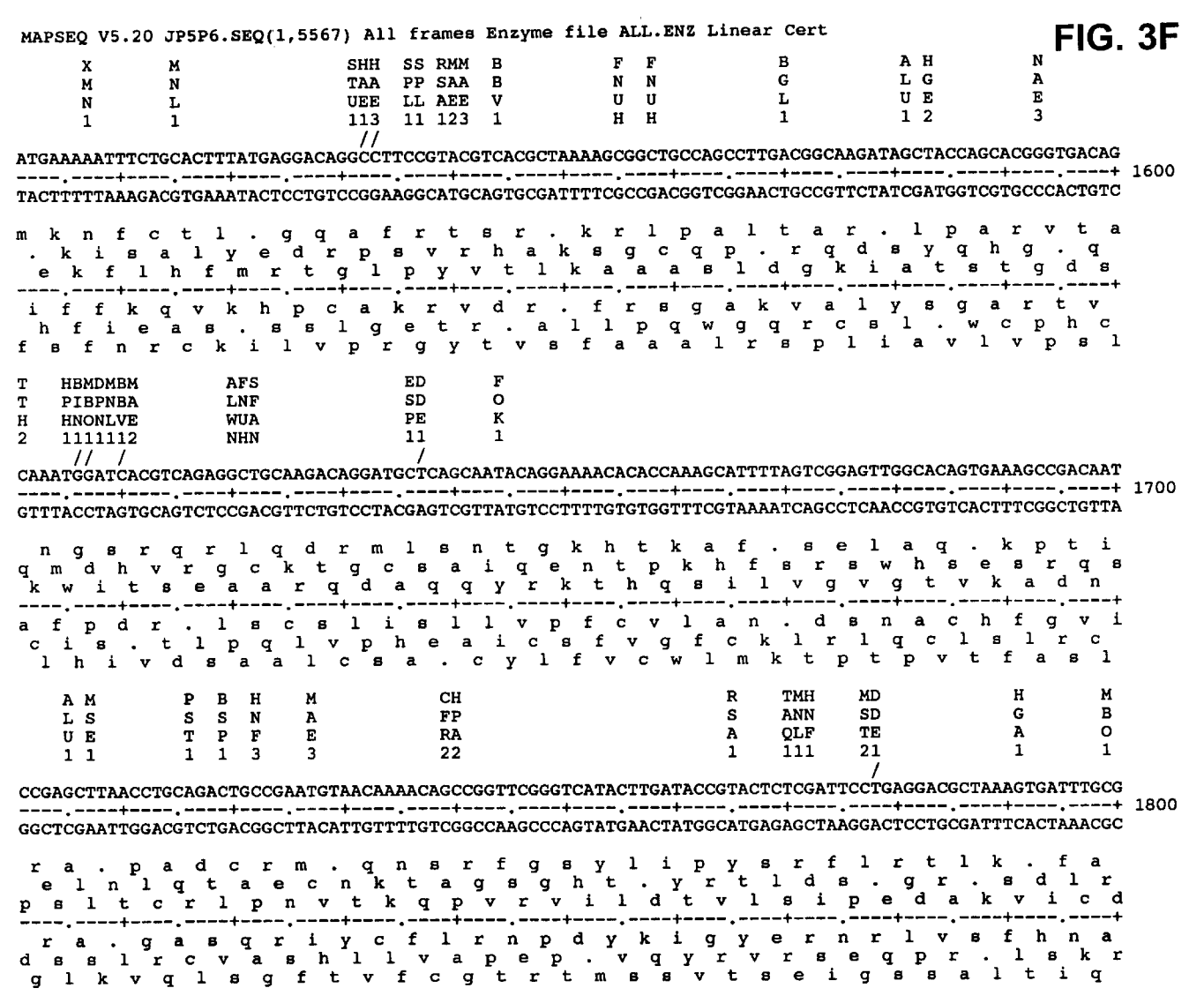
Figure 3G:
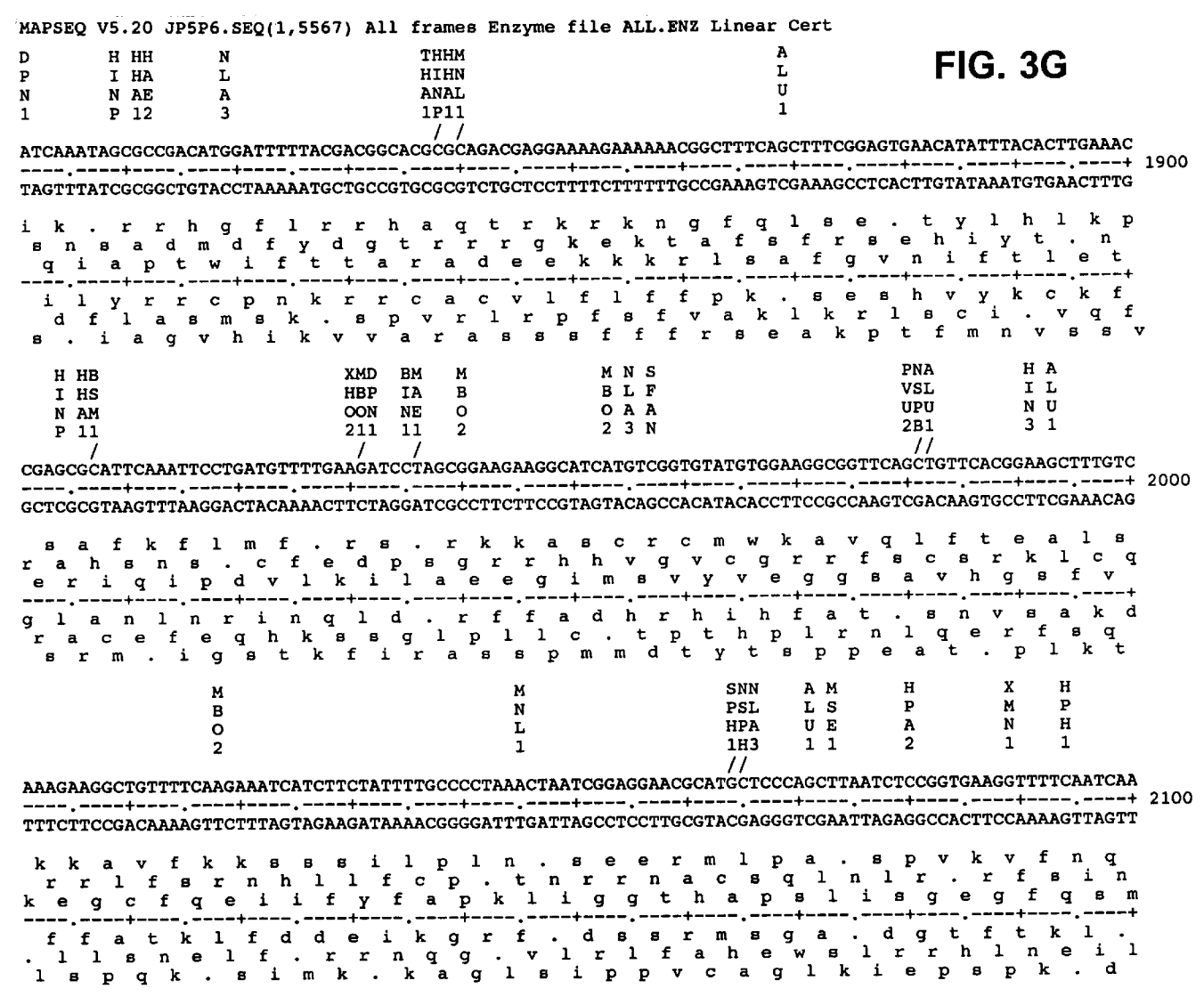
Figure 3H:
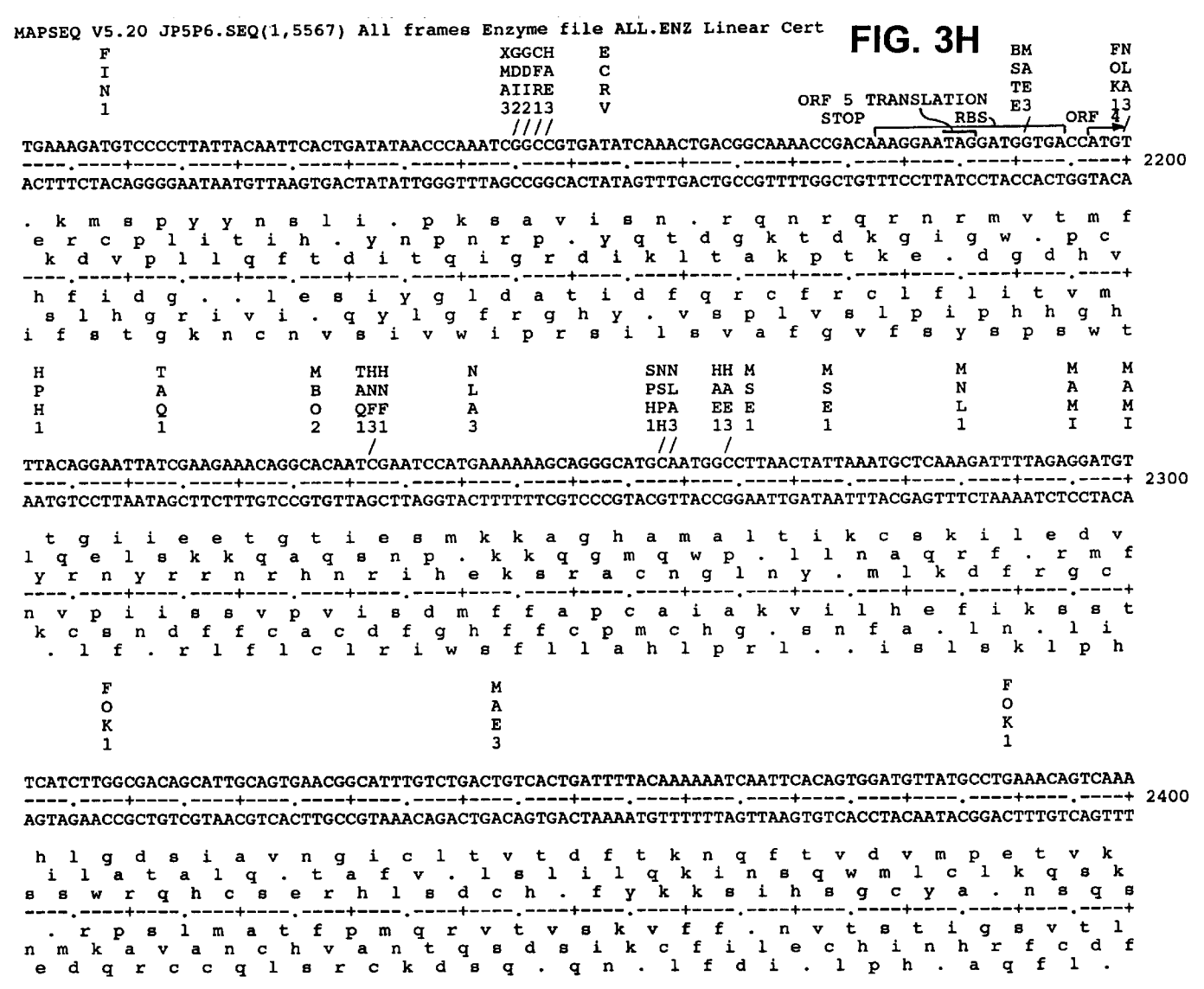
Figure 3J:
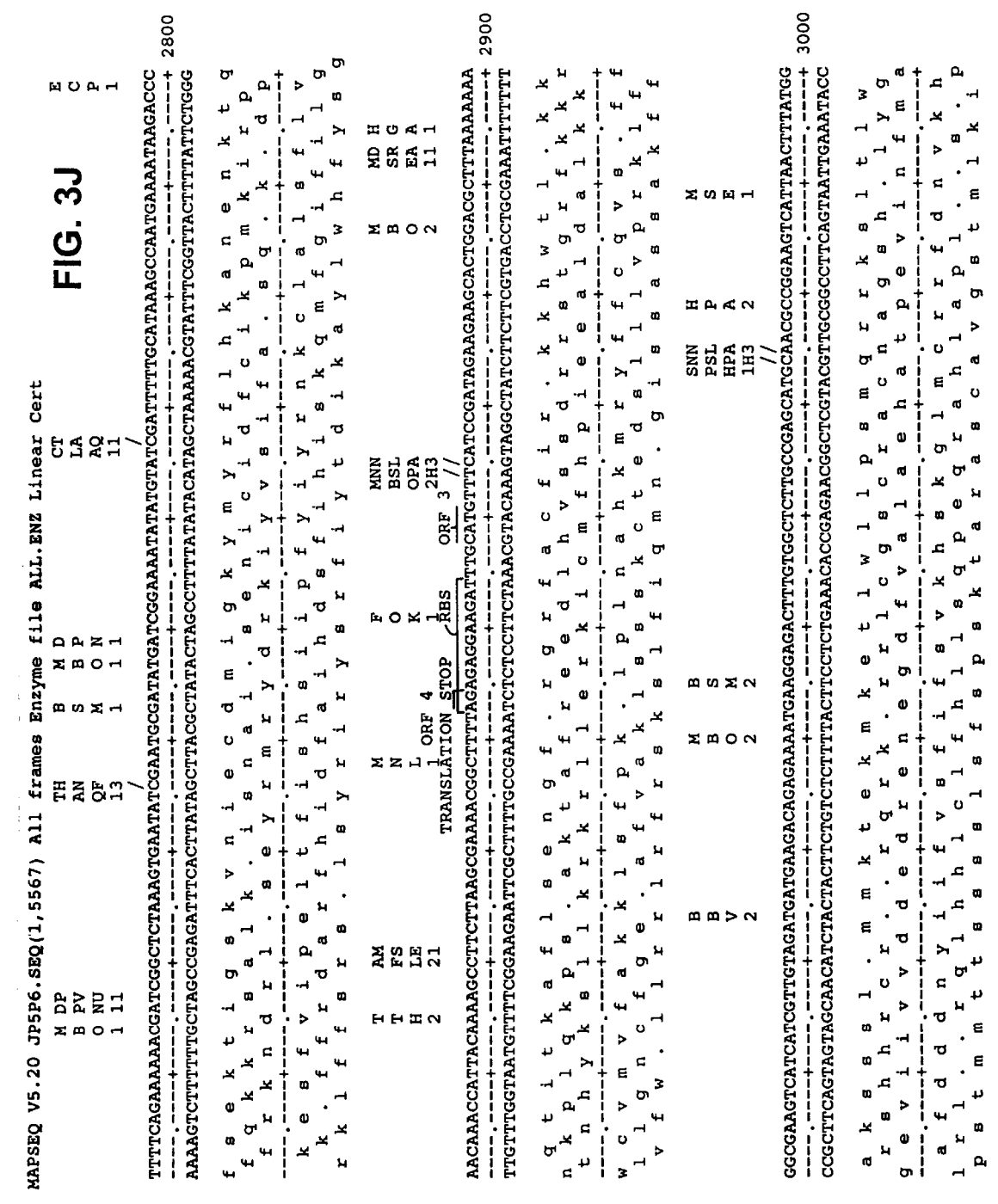
Figure 3K:
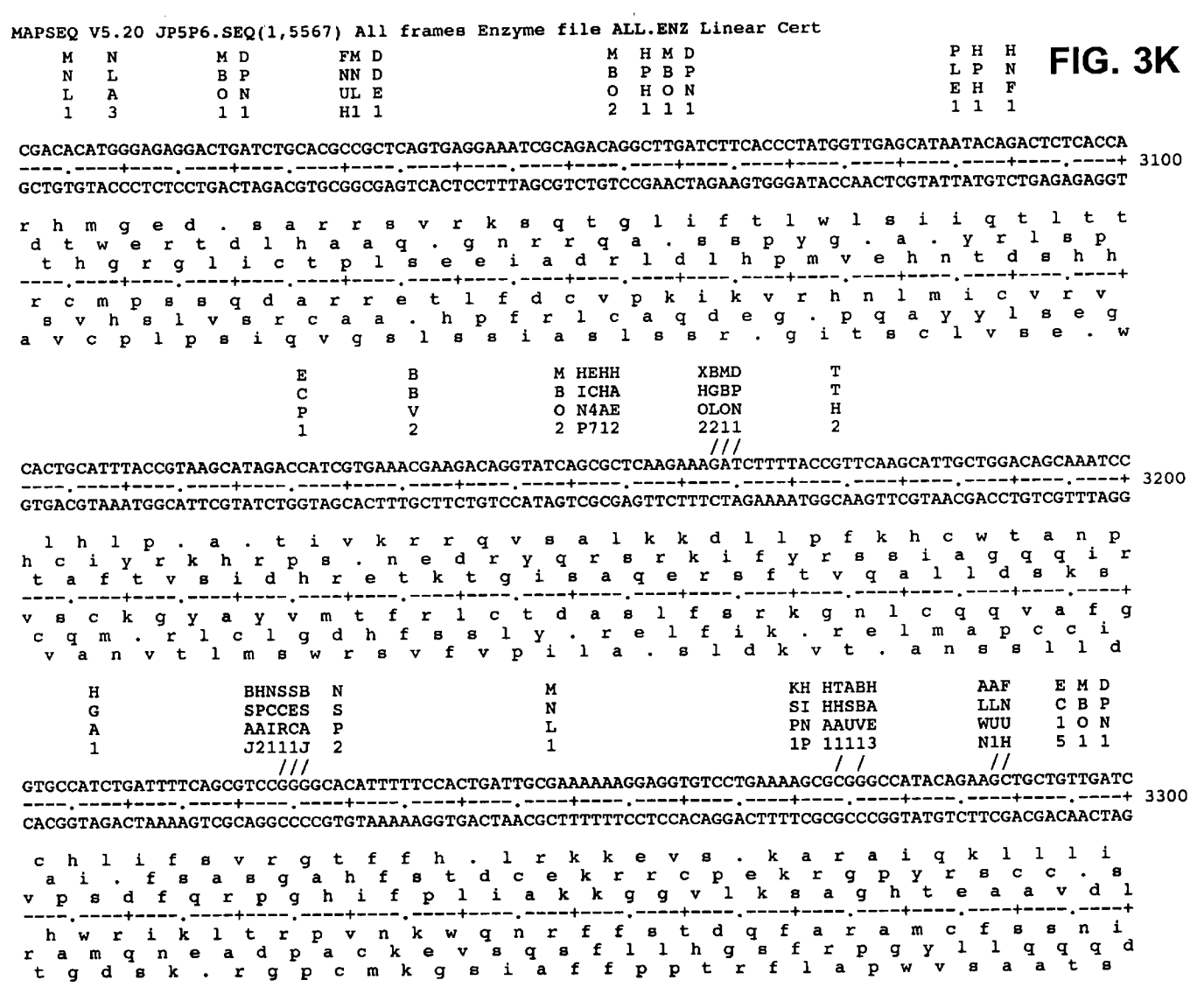
Figure 3L:
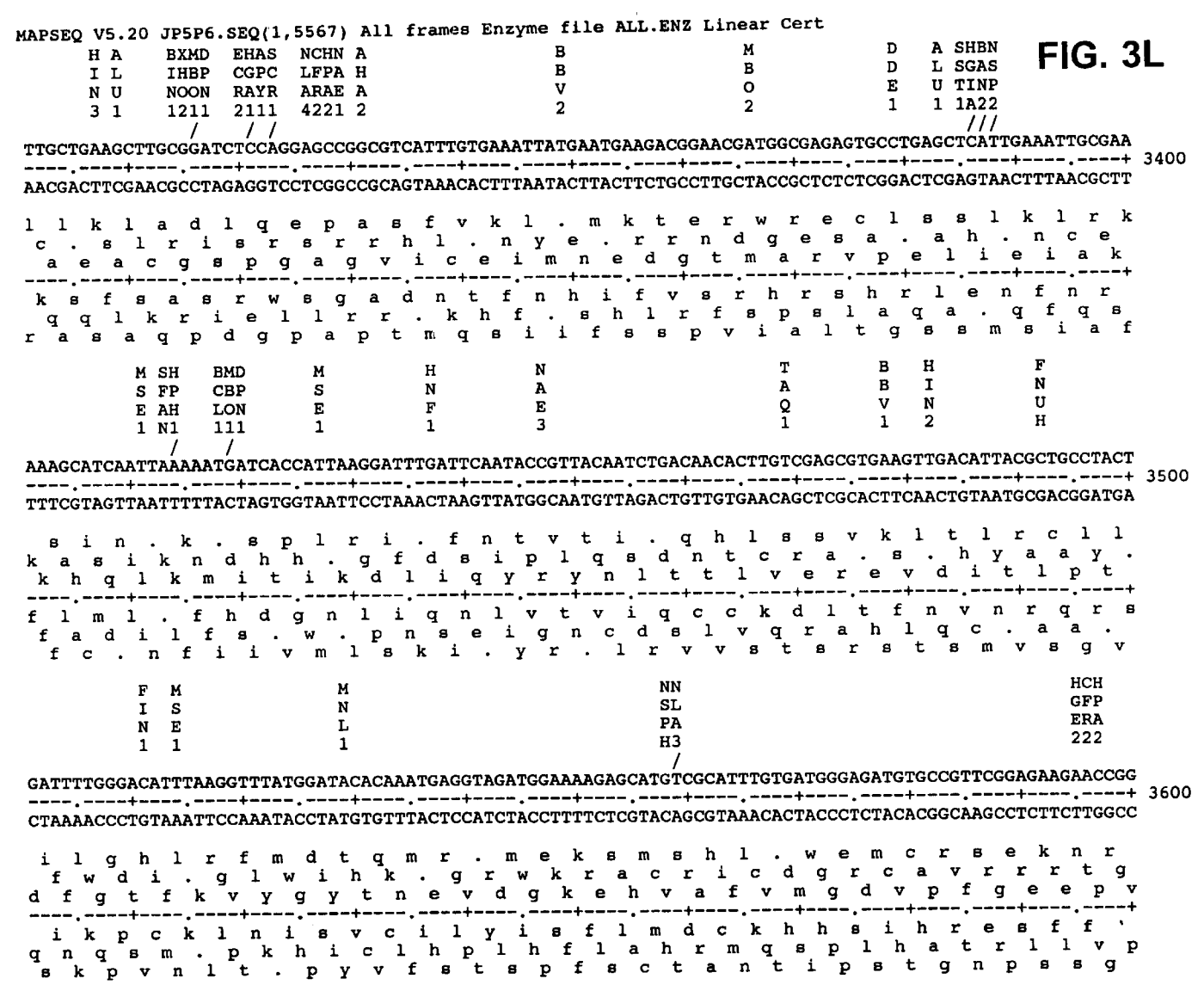
Figure 3M:
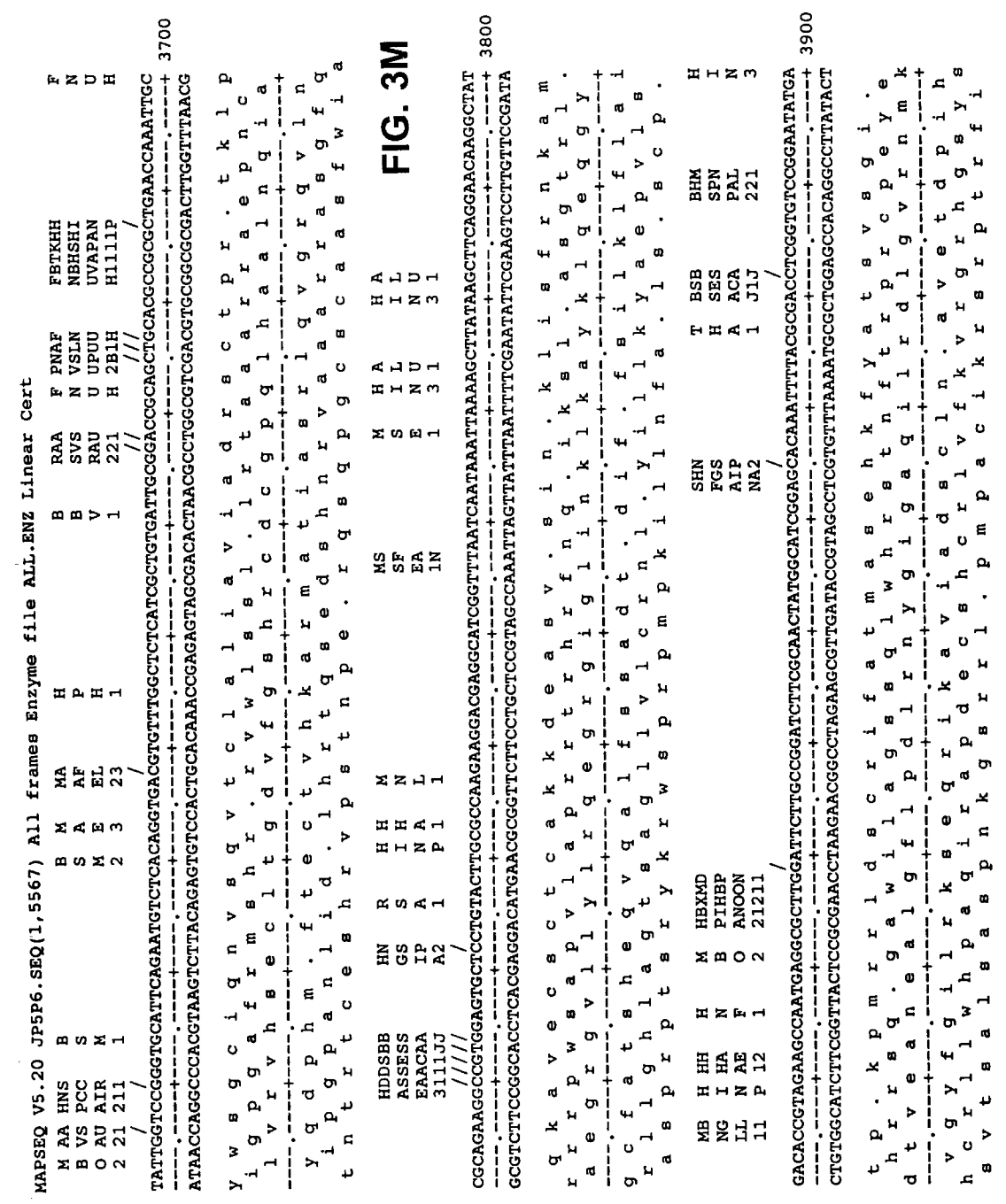
Figure 3N:
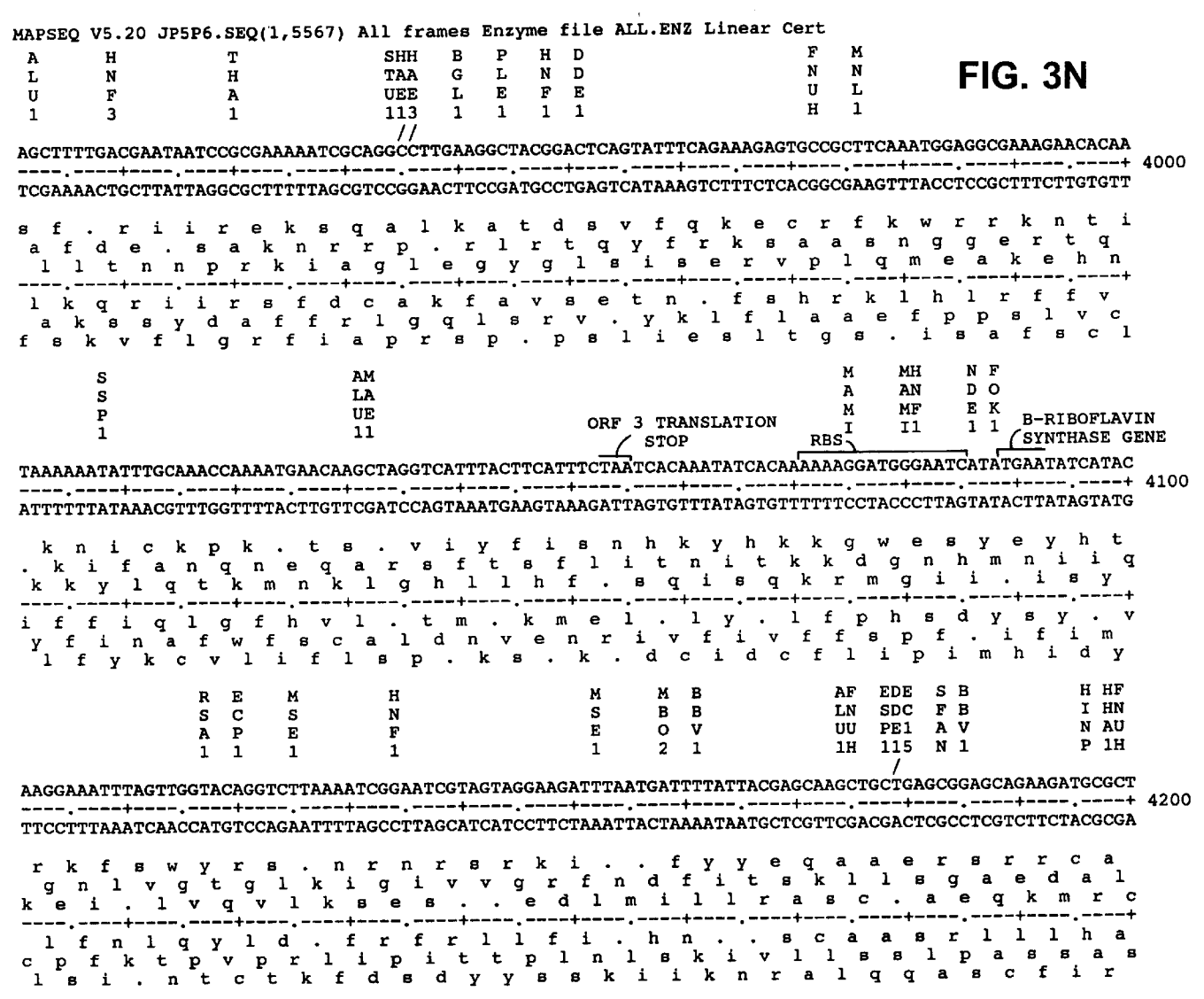
Figure 3P:
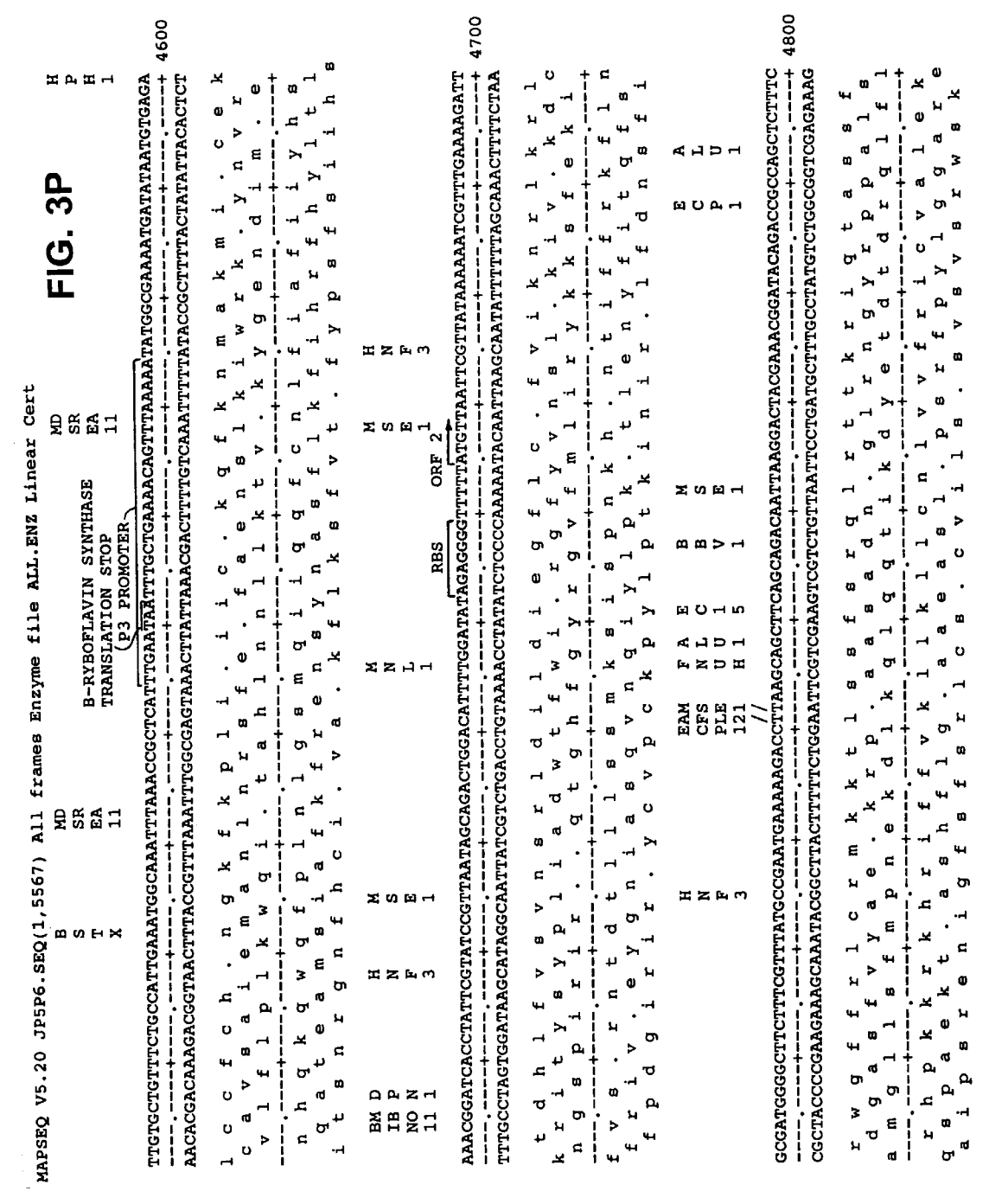
Figure 3Q:
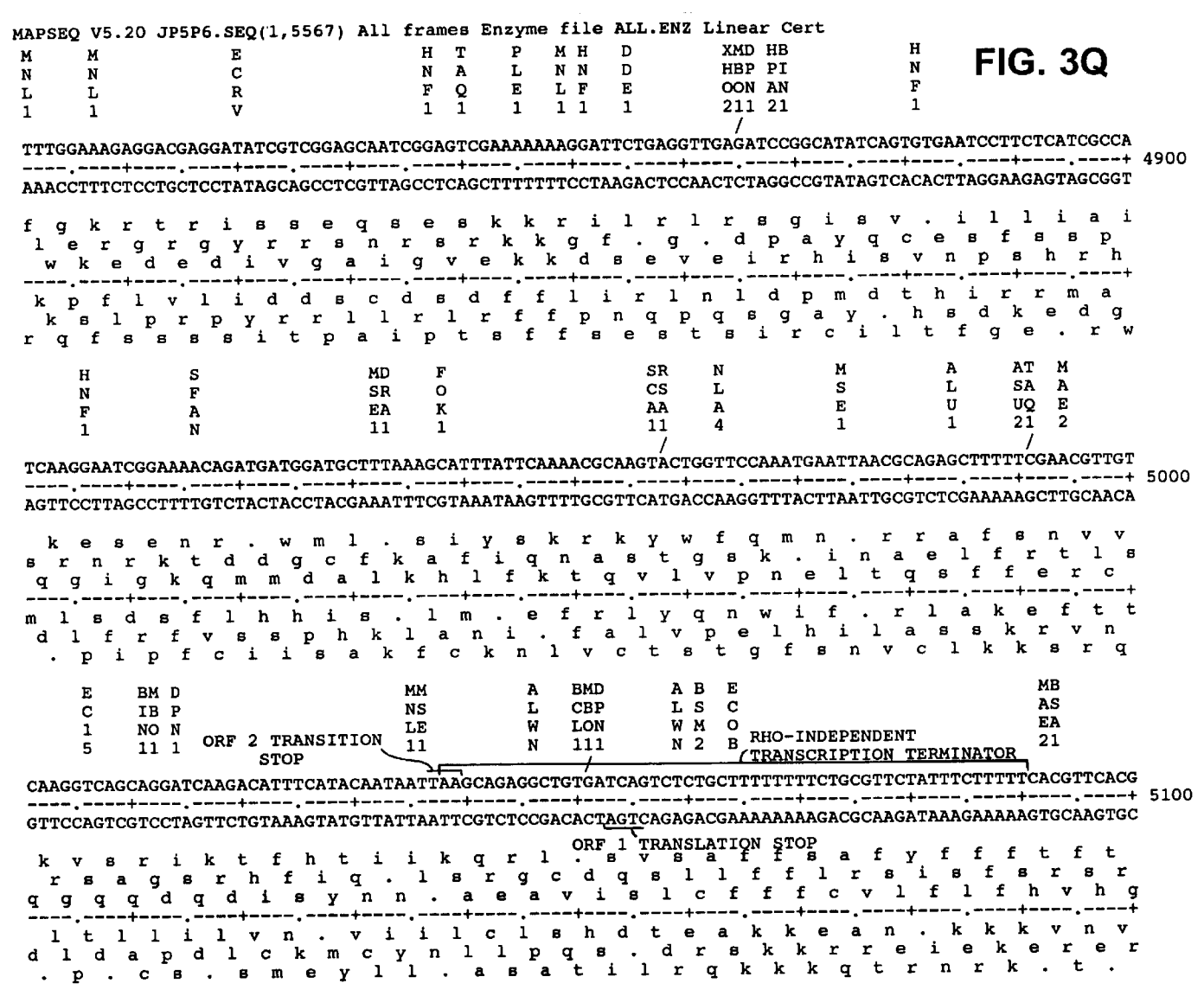
Figure 3R:
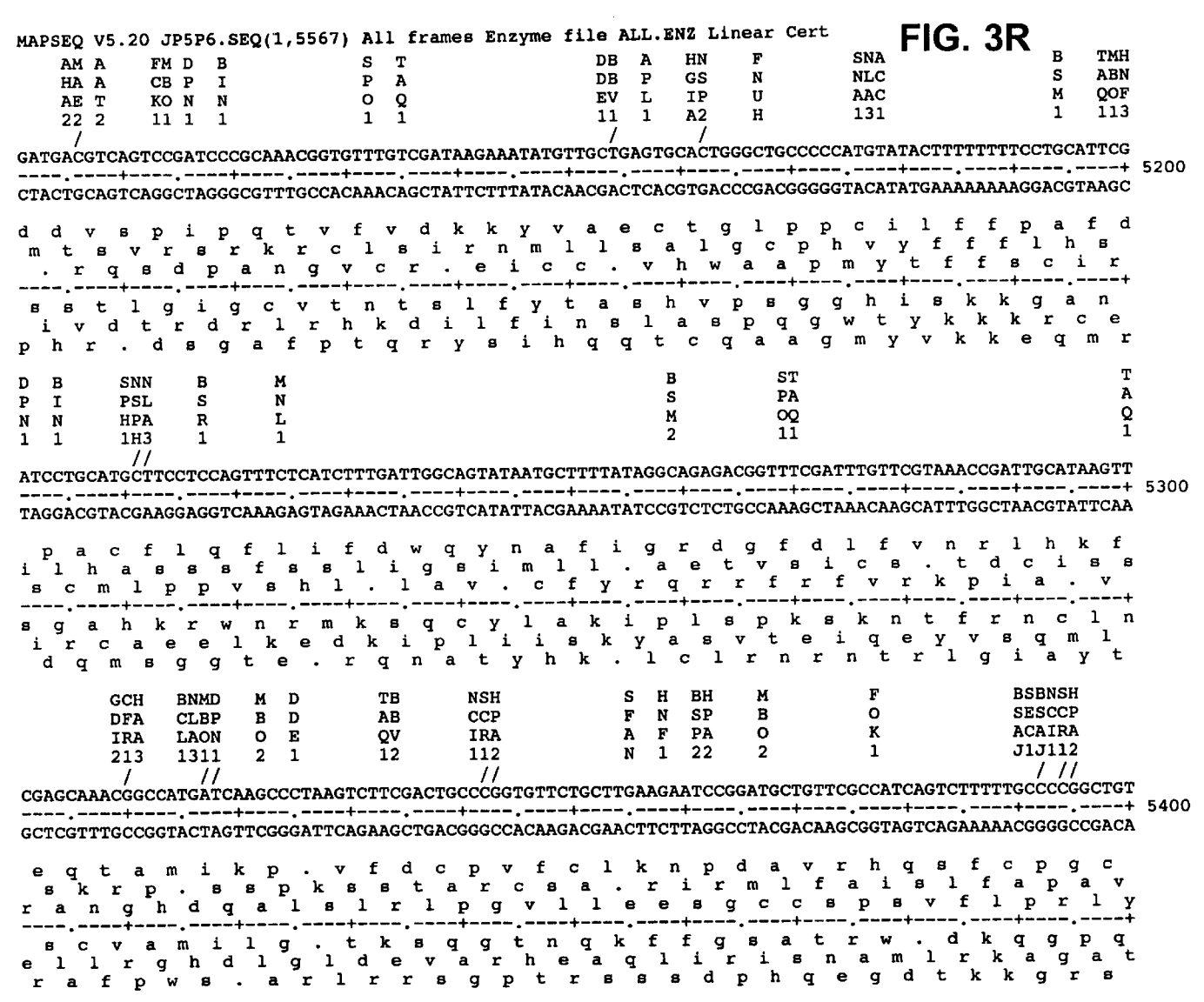
Figure 3S:
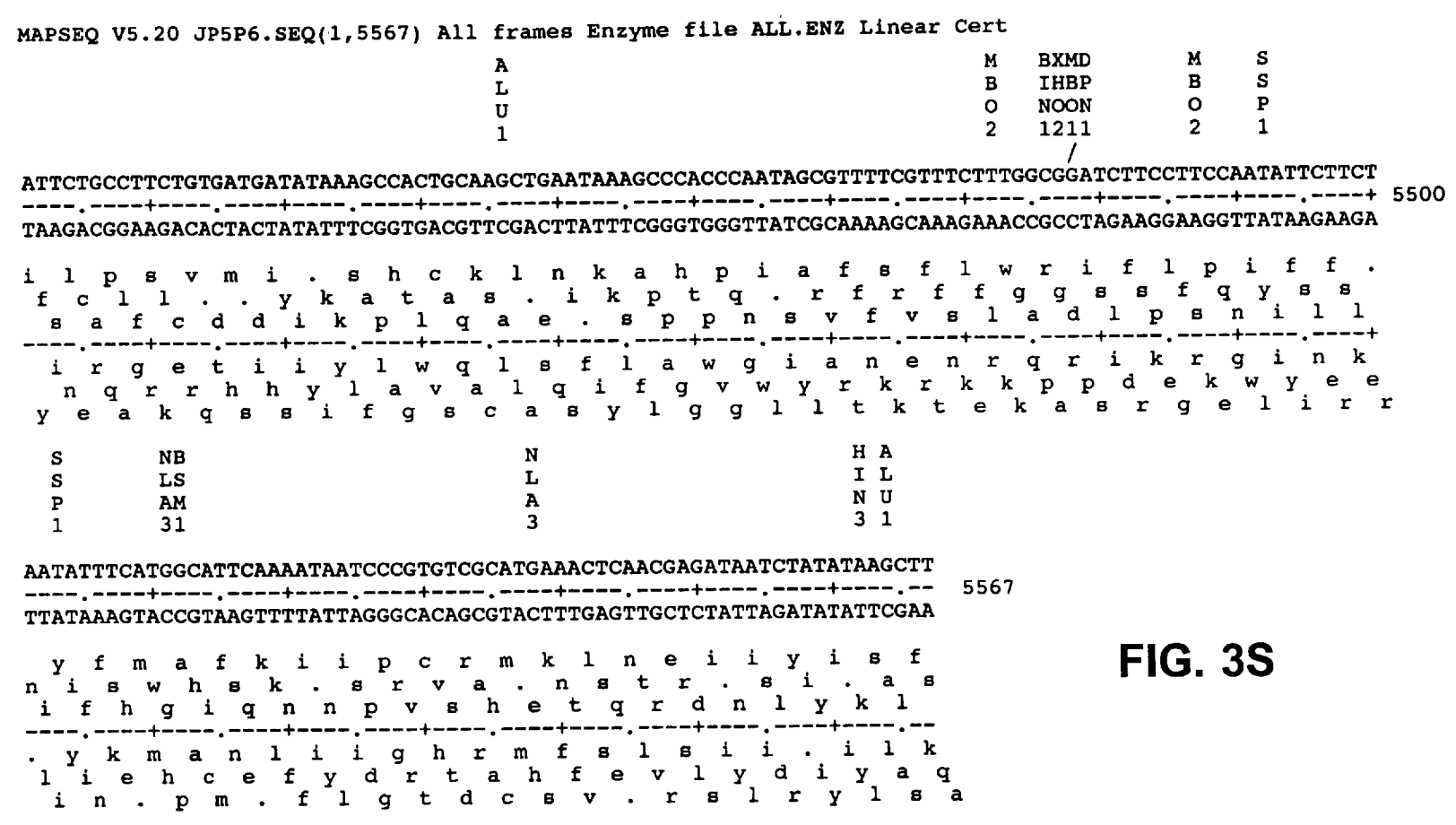

FIGS. 3A–S. The complete nucleotide and deduced amino acid sequences of the B. subtilis rib operon. The nucleotide sequence was determined by dideoxy sequencing of M13 clones. The deduced amino acid sequence is indicated by the one letter code (Lehninger, Biochemistry, 2d Ed., Worth Publishers, Inc., New York, p. 72).

Figure 4:
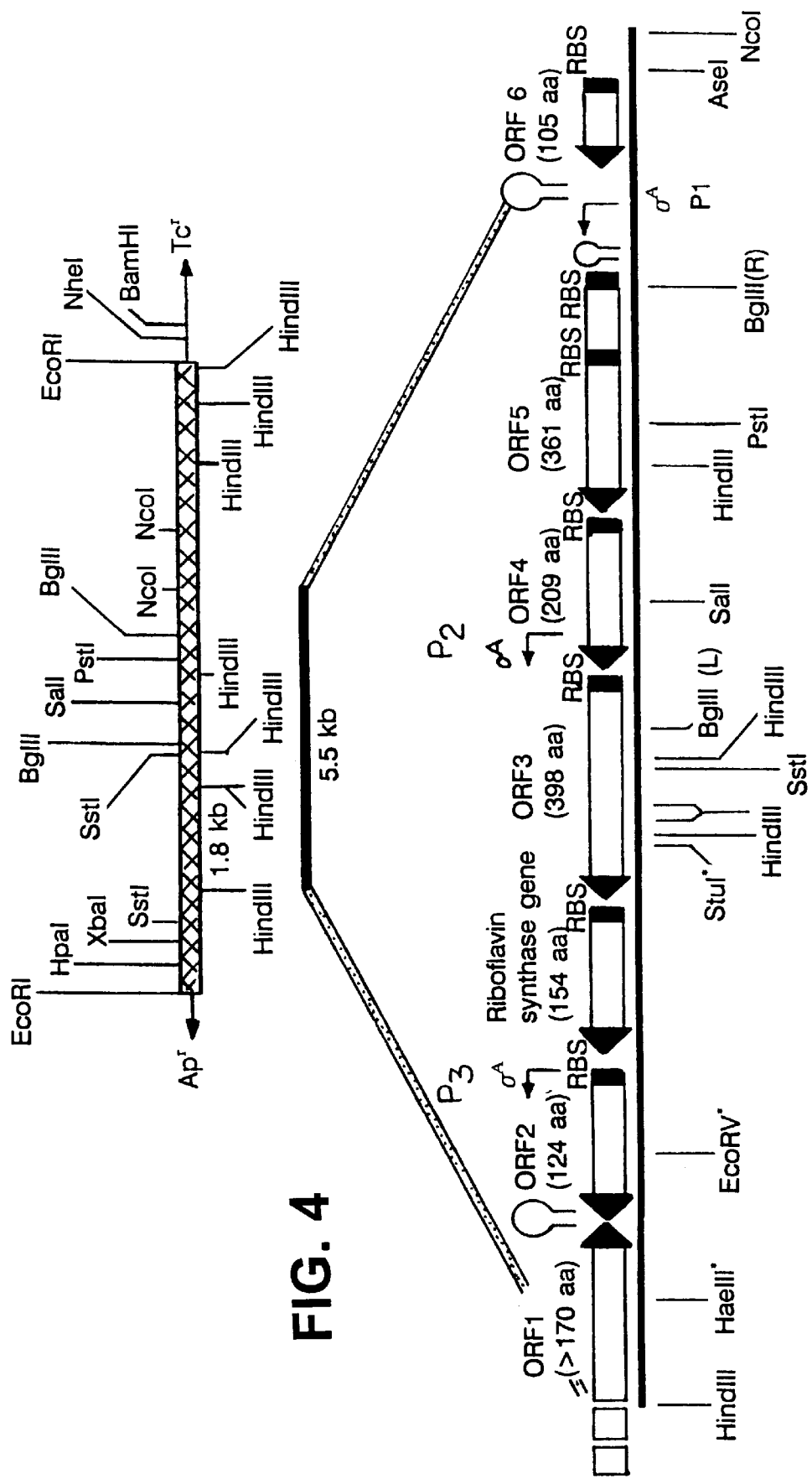

FIG. 4. A schematic representation of the rib gene cluster. The top diagram is the restriction endonuclease map of the cloned 10 kb EcoRI DNA fragment in plasmid pRF2, containing the B. subtilis rib operon. The hatched box depicts Rib+ cloned DNA, while the thin black line represents pBR322 DNA. The bottom diagram is based on the complete nucleotide sequence of the 6.0 kb fragment to which the rib operon was localized. Open reading frames are depicted by open boxes, with arrows indicating the direction of transcription, and closed boxes indicating the putative ribosome binding sites. Probable $\sigma^A$ promoter regions are shown. Tentatively identified rho-independent transcription termination sites are indicated by a "hairpin" symbol. Not all restriction sites are indicated.

Figure 5:
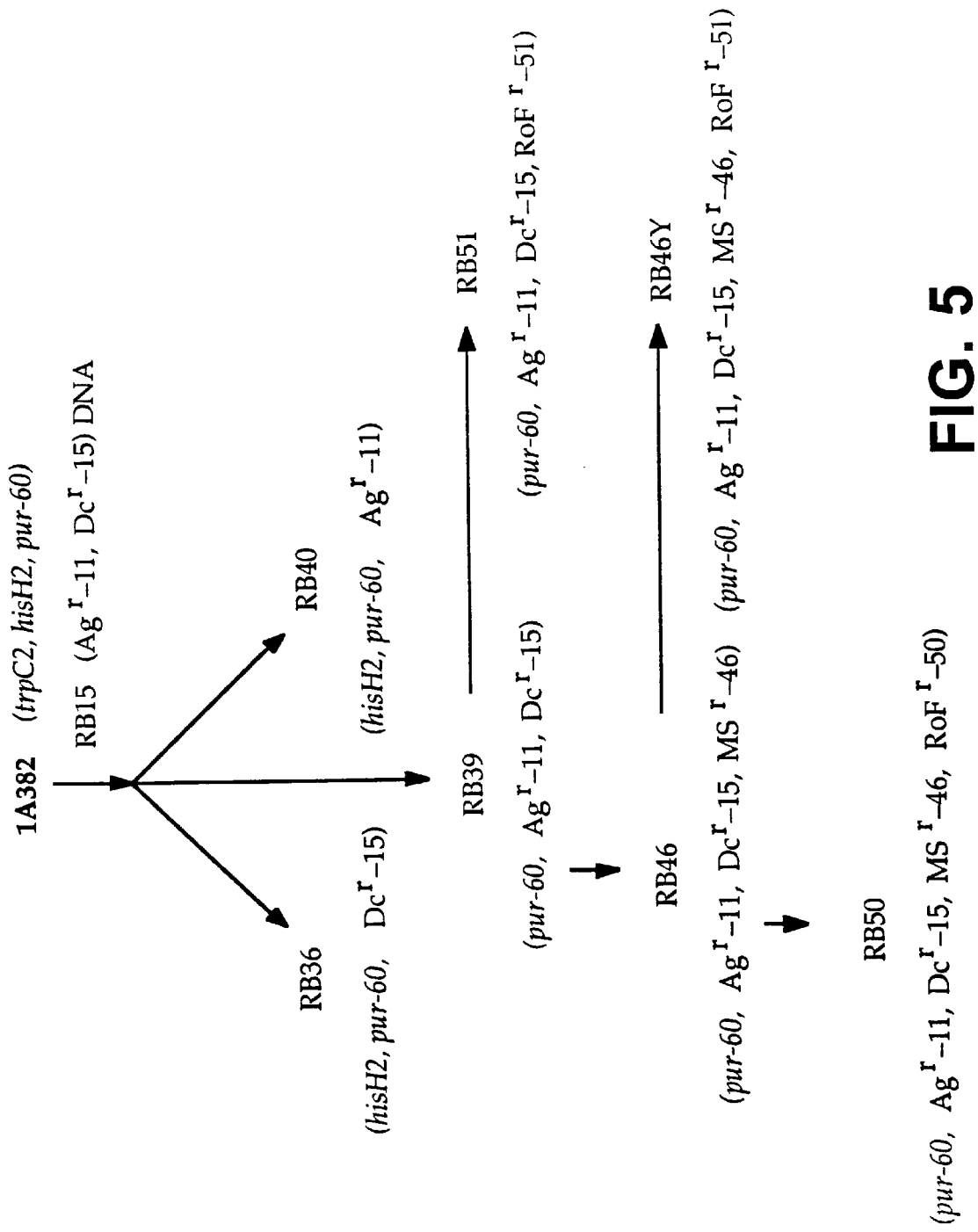

FIG. 5. Strain lineage of RB50. The lineage of the riboflavin overproducing strain of B. subtilis, RB50, is depicted. The various parent strains were exposed to riboflavin and purine analogs to select appropriate mutations.

Figure 6:
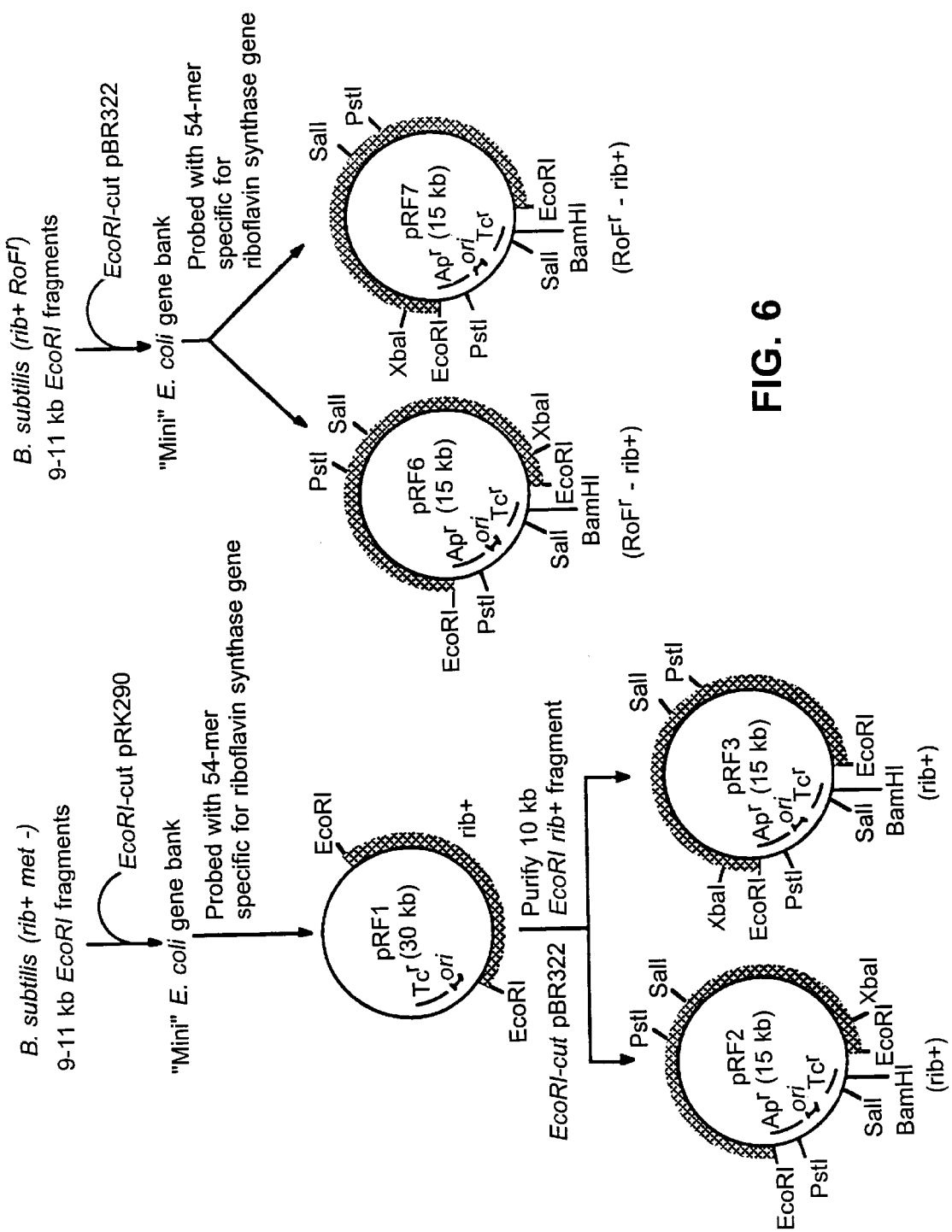

FIG. 6. Origins of rib+ recombinant plasmids. A schematic diagram of the production of the rib operon-containing recombinant plasmids pRF1, pRF2, pRF3, pRF6 and pRF7 is presented. A library of size-selected, 9–11 kb fragments of *B. subtilis* DNA was used to produce a gene library in *E. coli* plasmid vectors. Clones were selected by hybridization to the 54-mer probe specific for the β subunit of the riboflavin synthase gene.

Figure 7:
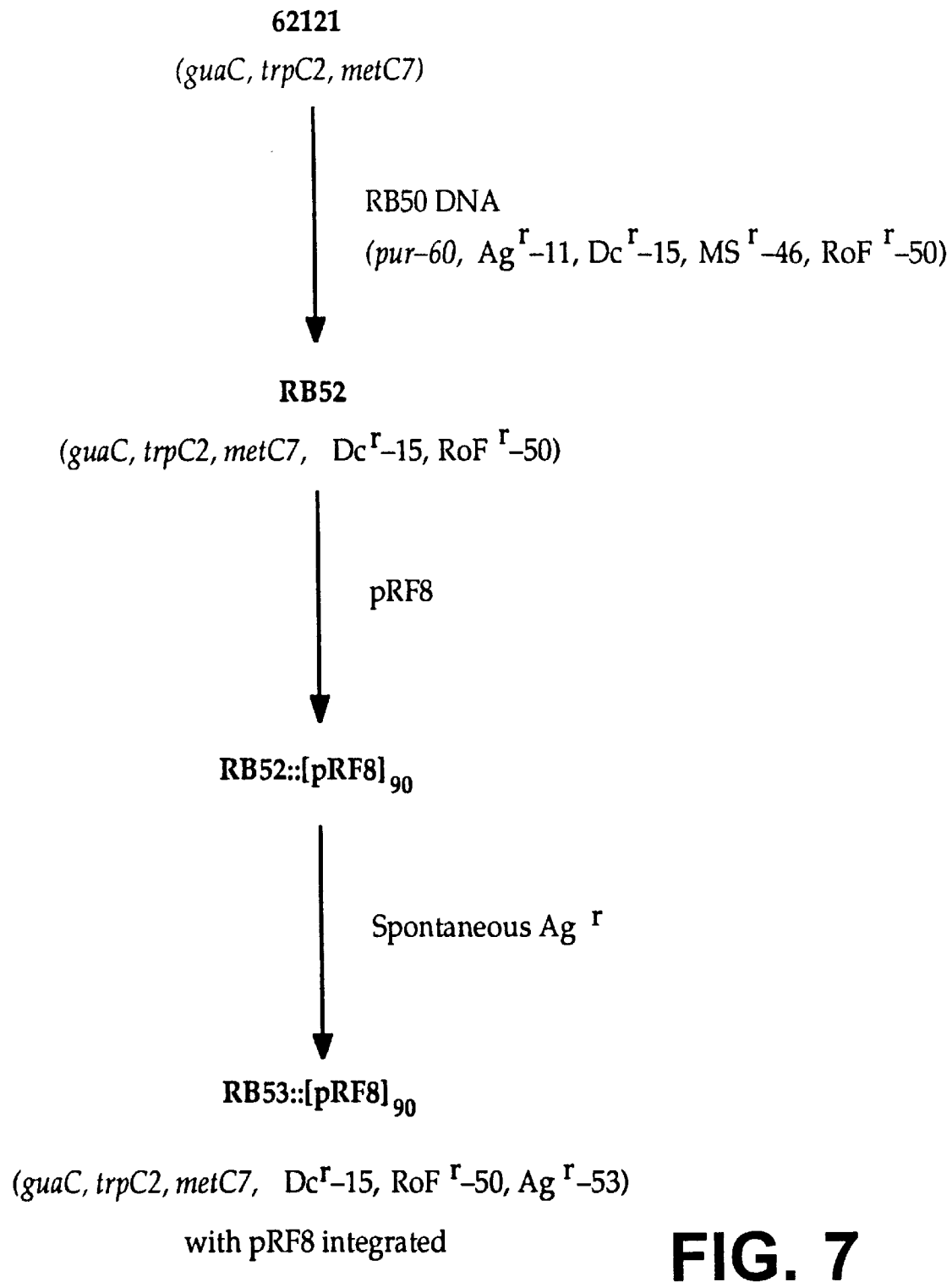

FIG. 7. The strain lineage of *B. subtilis* RB53::[pRF8]$_{90}$. Plasmid pRF8 was integrated into the chromosome of the intermediate strain RB52 and amplified; the resulting strain was exposed to the purine analog azaguanine.

Figure 8:
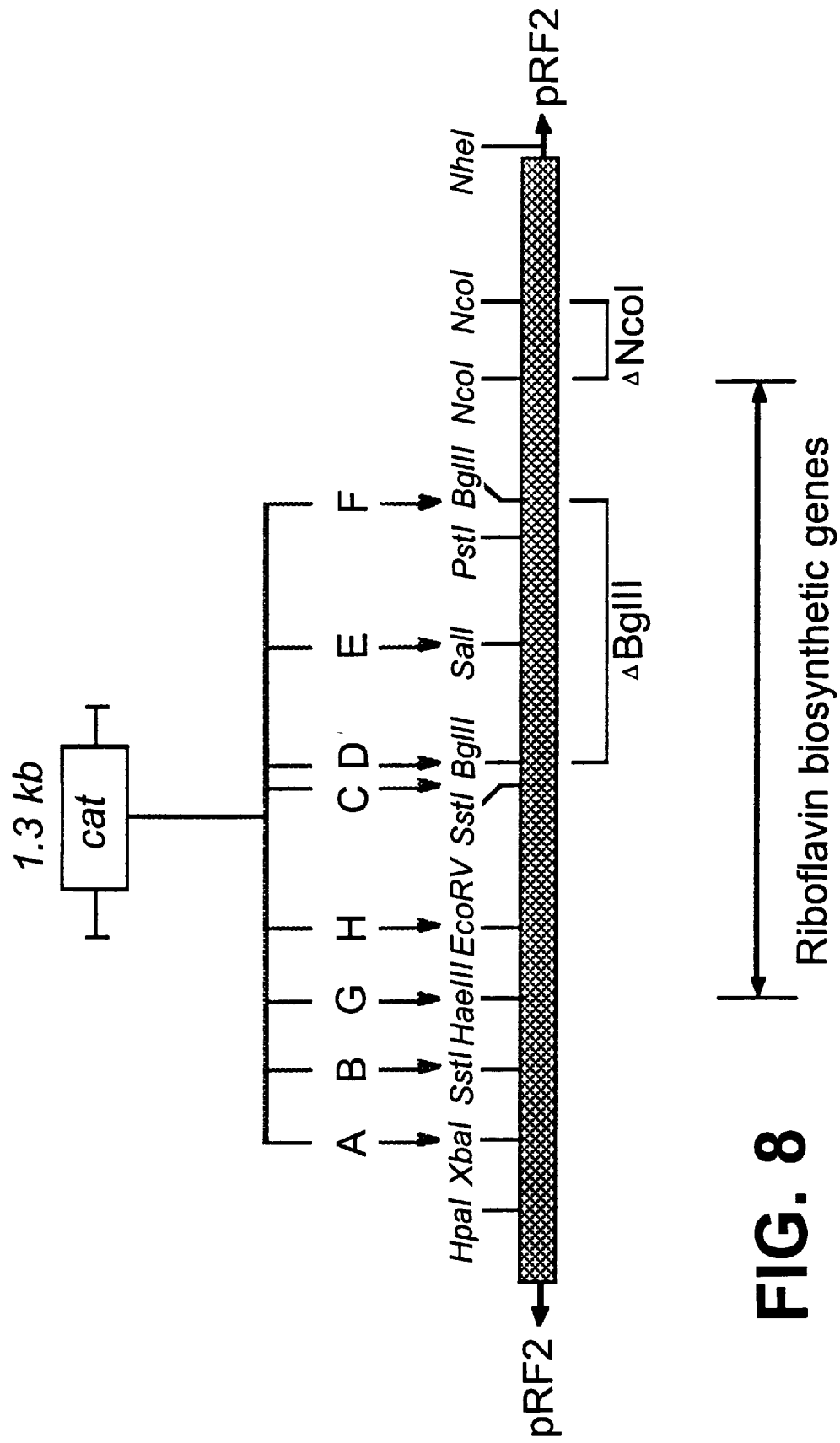

FIG. 8. Identification of regions essential for riboflavin biosynthesis using insertions and deletions. A diagram is presented of the 10 kb cloned EcoRI DNA fragment with the regions essential for riboflavin biosynthesis indicated. Insertions and deletions at the indicated restriction sites enabled the localization of the rib operon. Not all restriction sites are indicated.

FIG. 9. Hairpin-loop structures of the possible rho-independent transcription termination sites. Their locations in the nucleotide sequence of FIG. 3 are shown below each structure. Also presented are their free energies of formation, determined according to Tinoco et al. (*Nature* (*London*) *New Biology* 246:40 (1973)).

Figure 10:
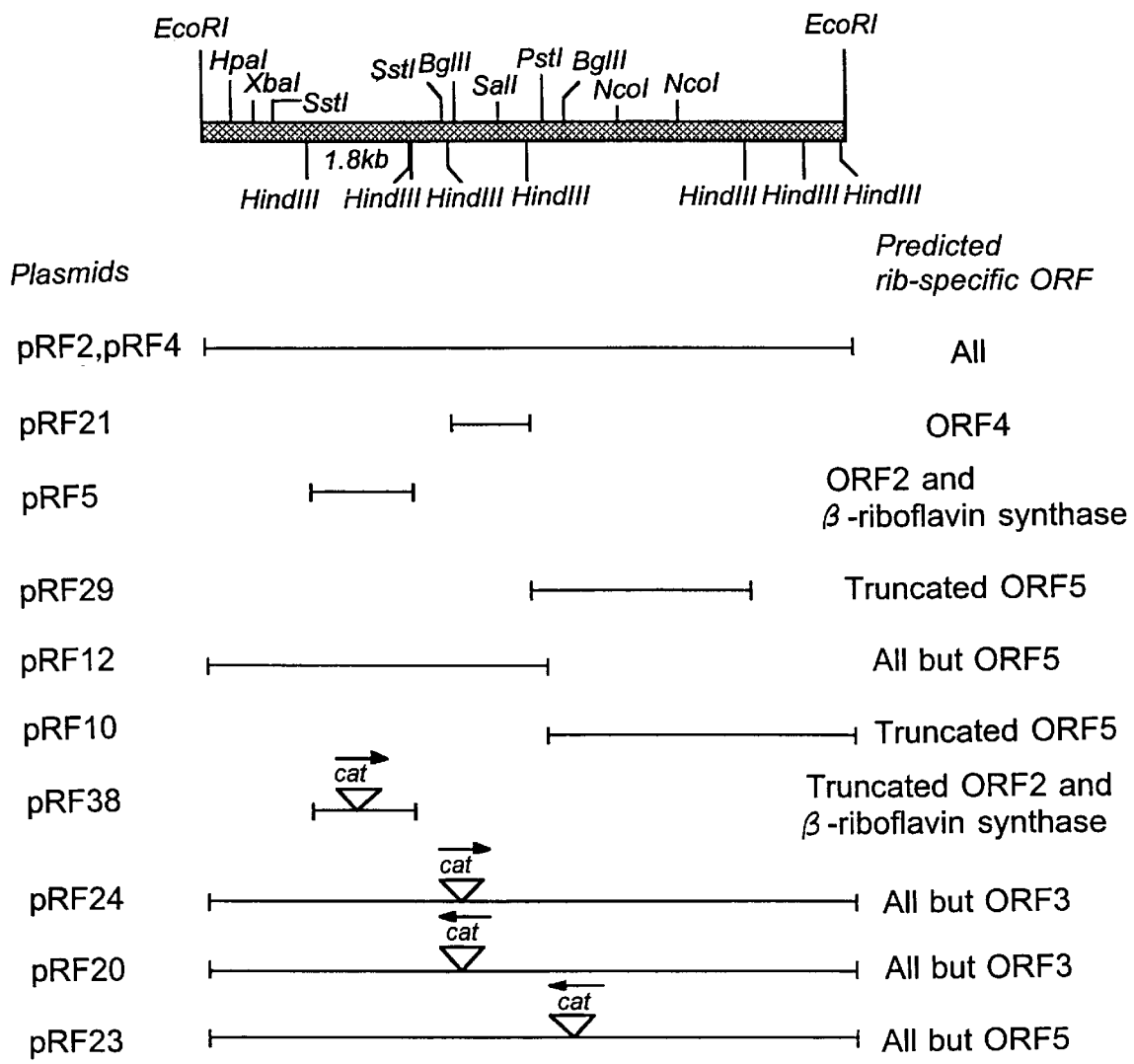

FIG. 10. Structure of various plasmid derivatives used in S-30 in vitro coupled transcription/translation reactions. A schematic diagram is shown of the rib operon regions contained in the plasmid derivatives used in the S-30 reactions, as well as the open reading frames predicted to be expressed.

Figure 11:
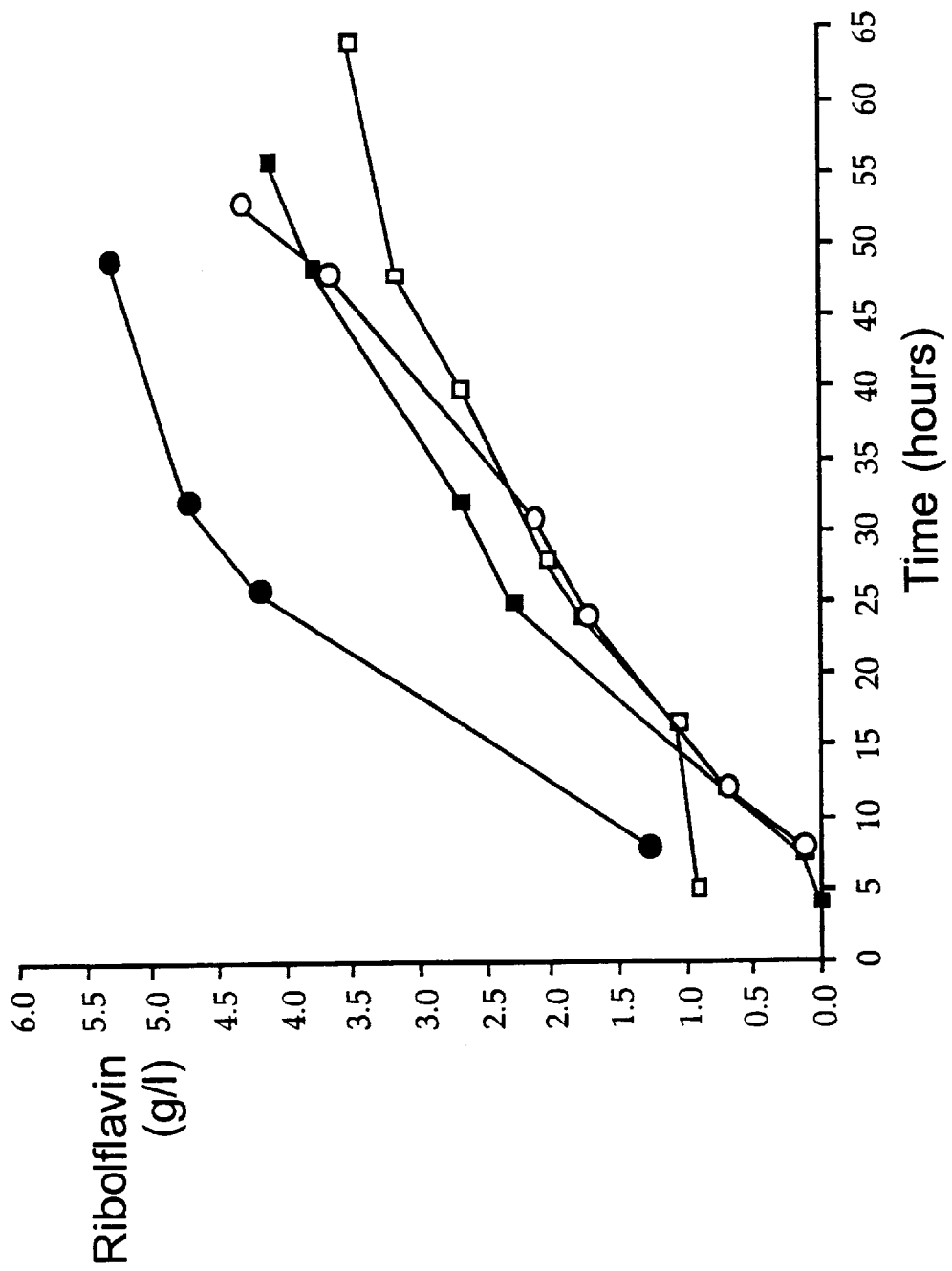

FIG. 11. Comparison of riboflavin production curves. Riboflavin production curves for various fermentation protocols are shown. Open squares: RBF-14 using RB50::[pRF8]$_{60}$ (Ade$^-$). Closed squares: RBF-22 using RB50::[pRF8]$_{60}$(Ade$^-$). Open circles: RBF-23 using RB50::[pRF8]$_{60}$(Ade$^-$). Closed circles: RBF-29 using RB50:: [pRF8]$_{60}$ (Ade$^+$).

Figure 12:
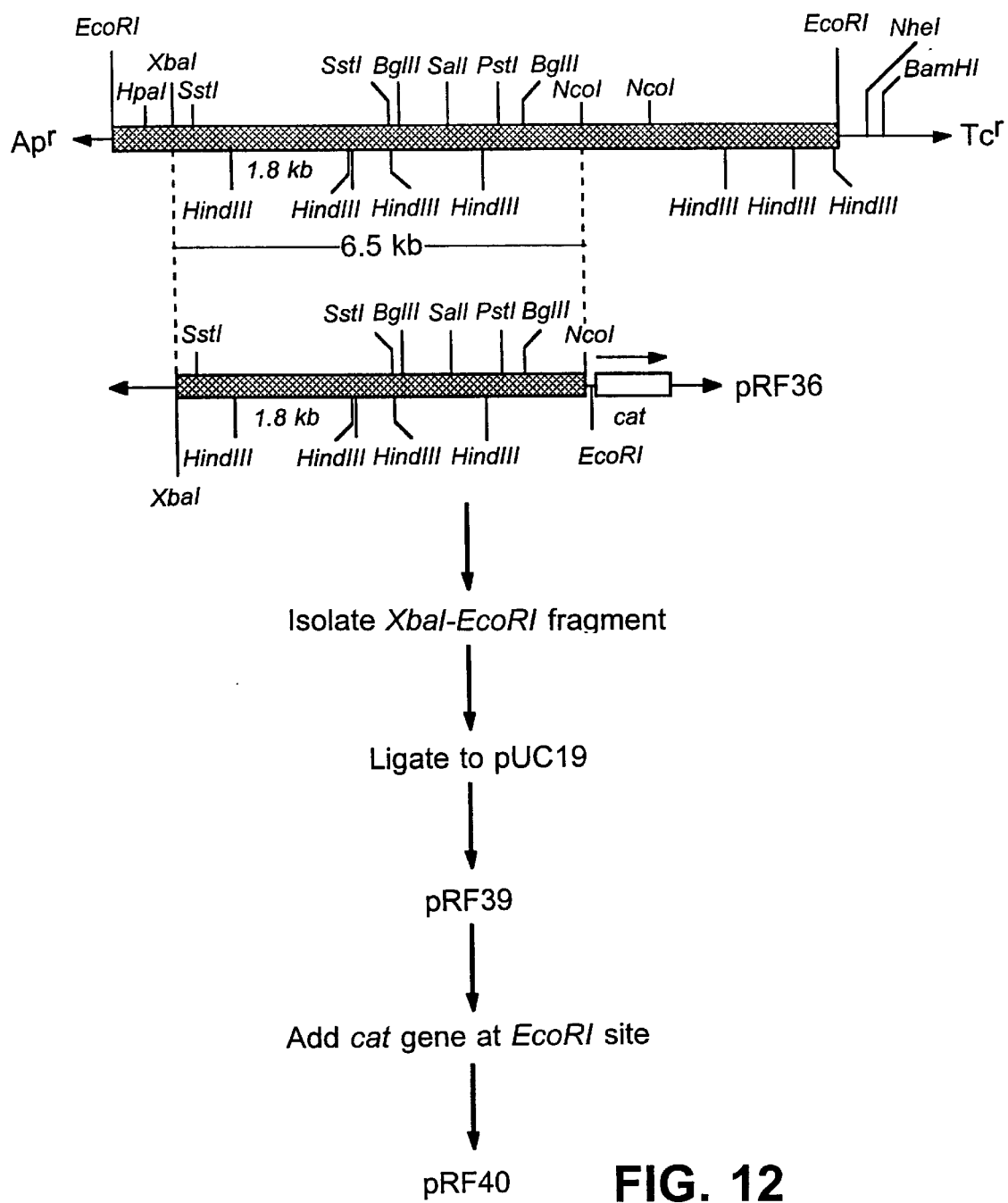

FIG. 12. Construction of pRF40.

Figure 13:
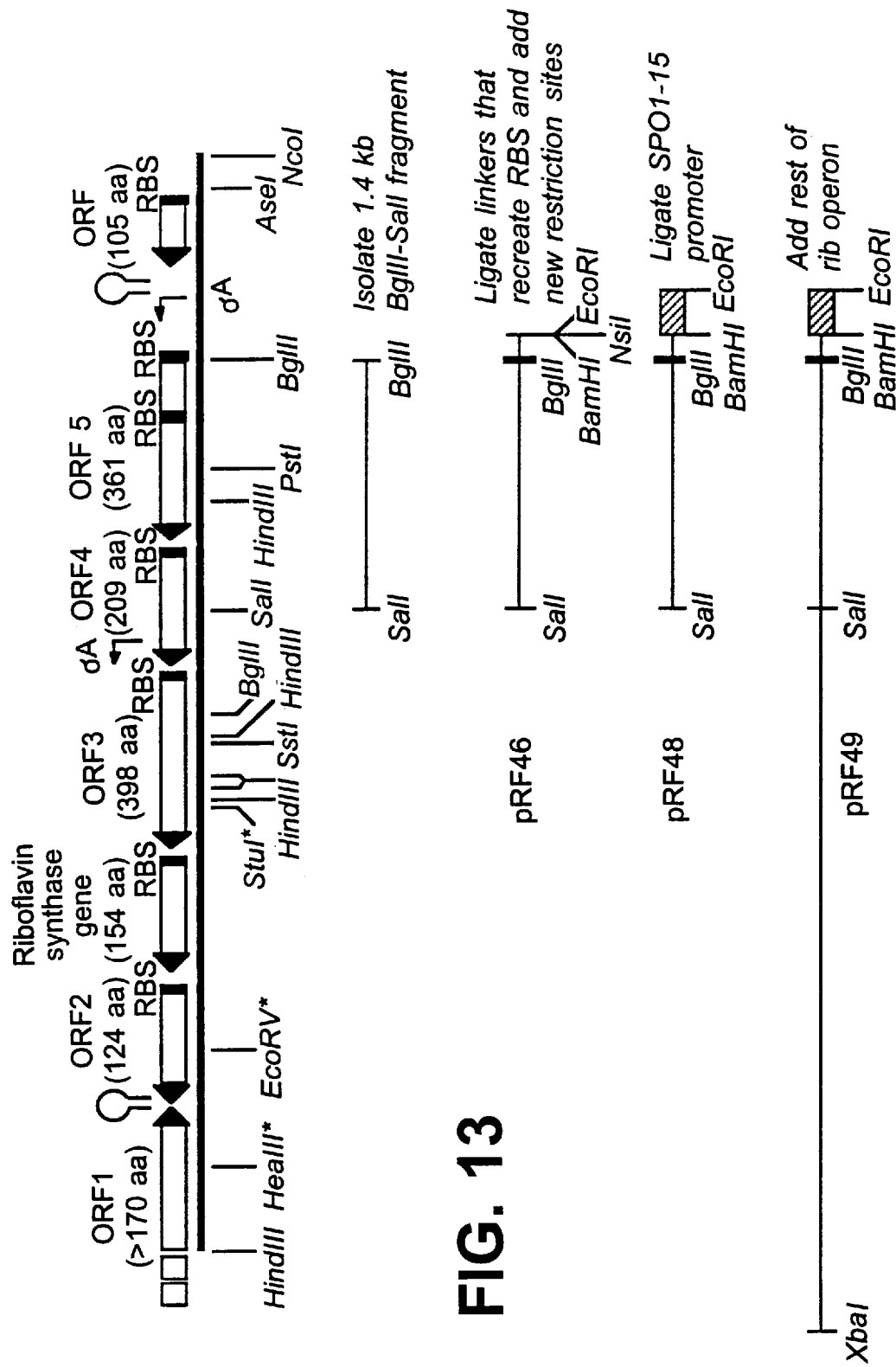

FIG. 13. Construction of pRF50.

Figure 14B:
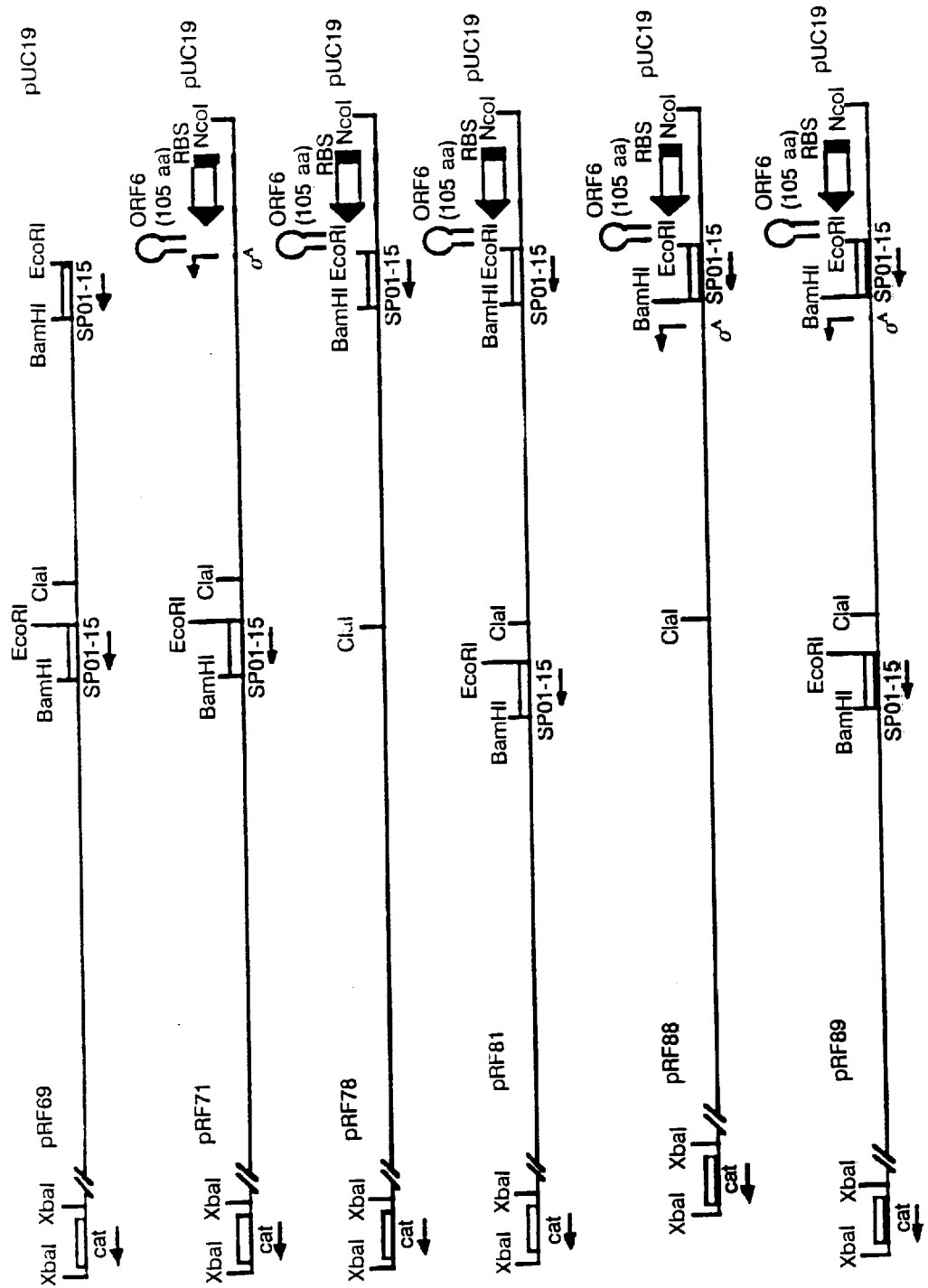
Figure 15:
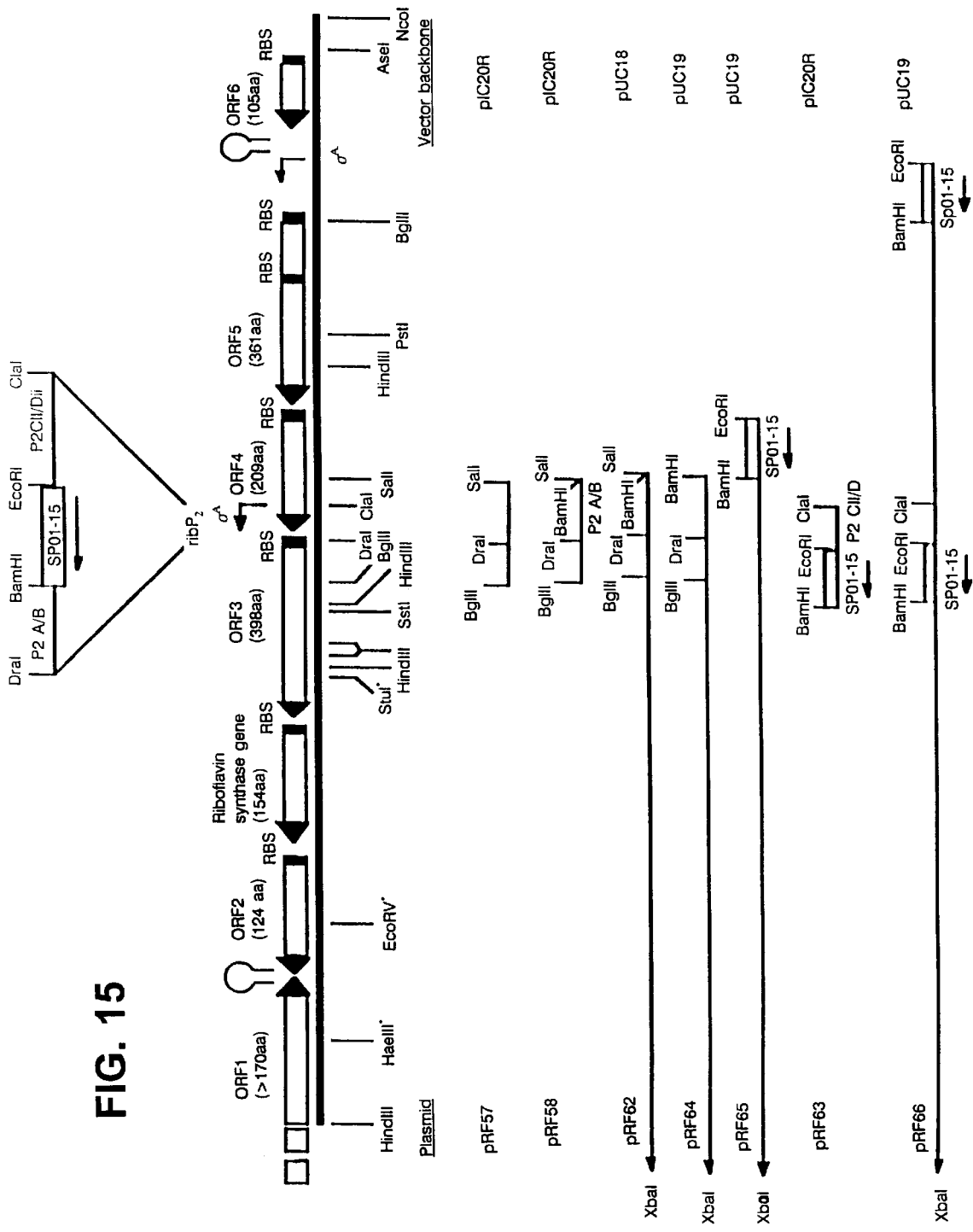
Figure 16A:
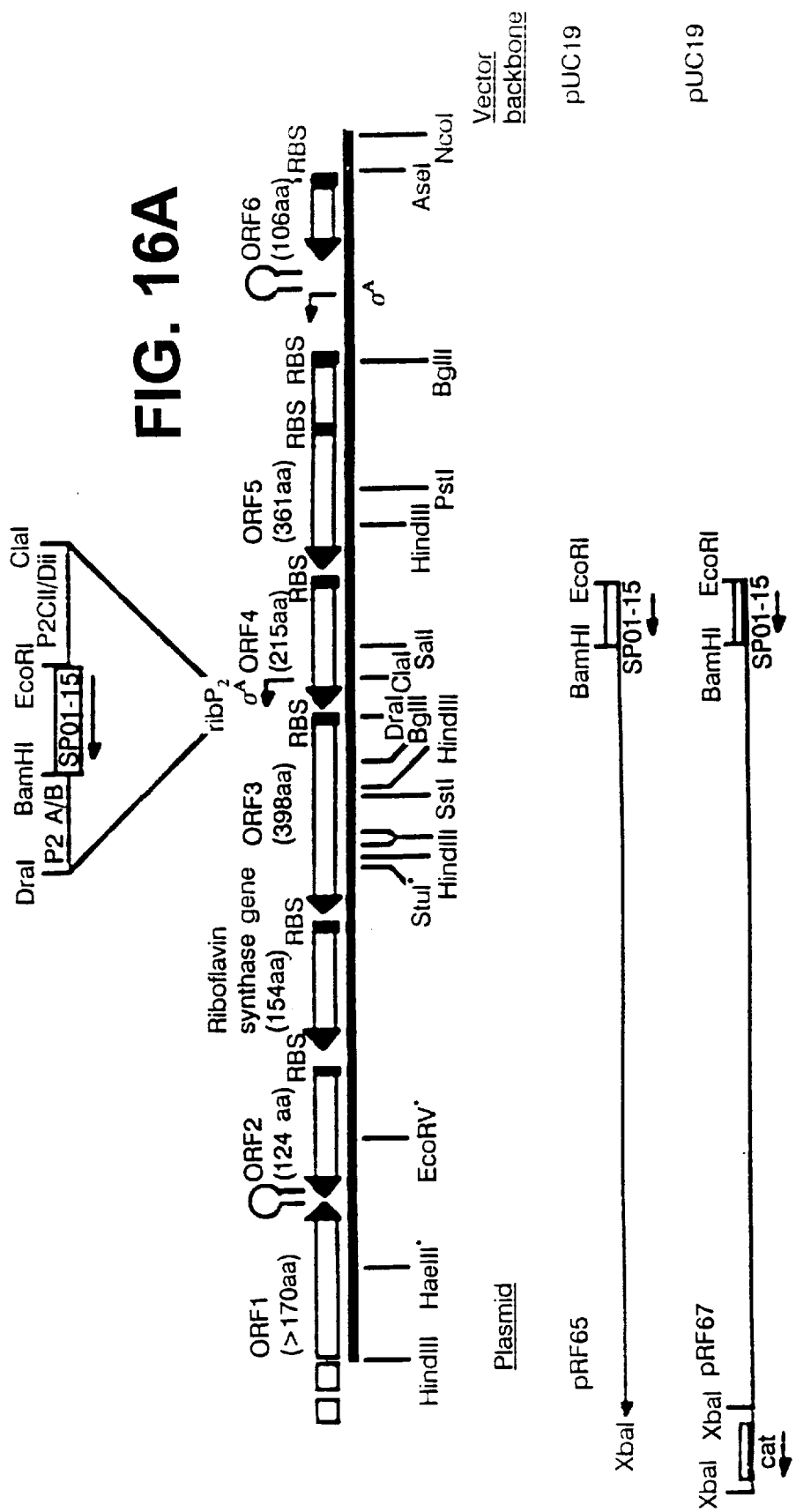
Figure 16B:
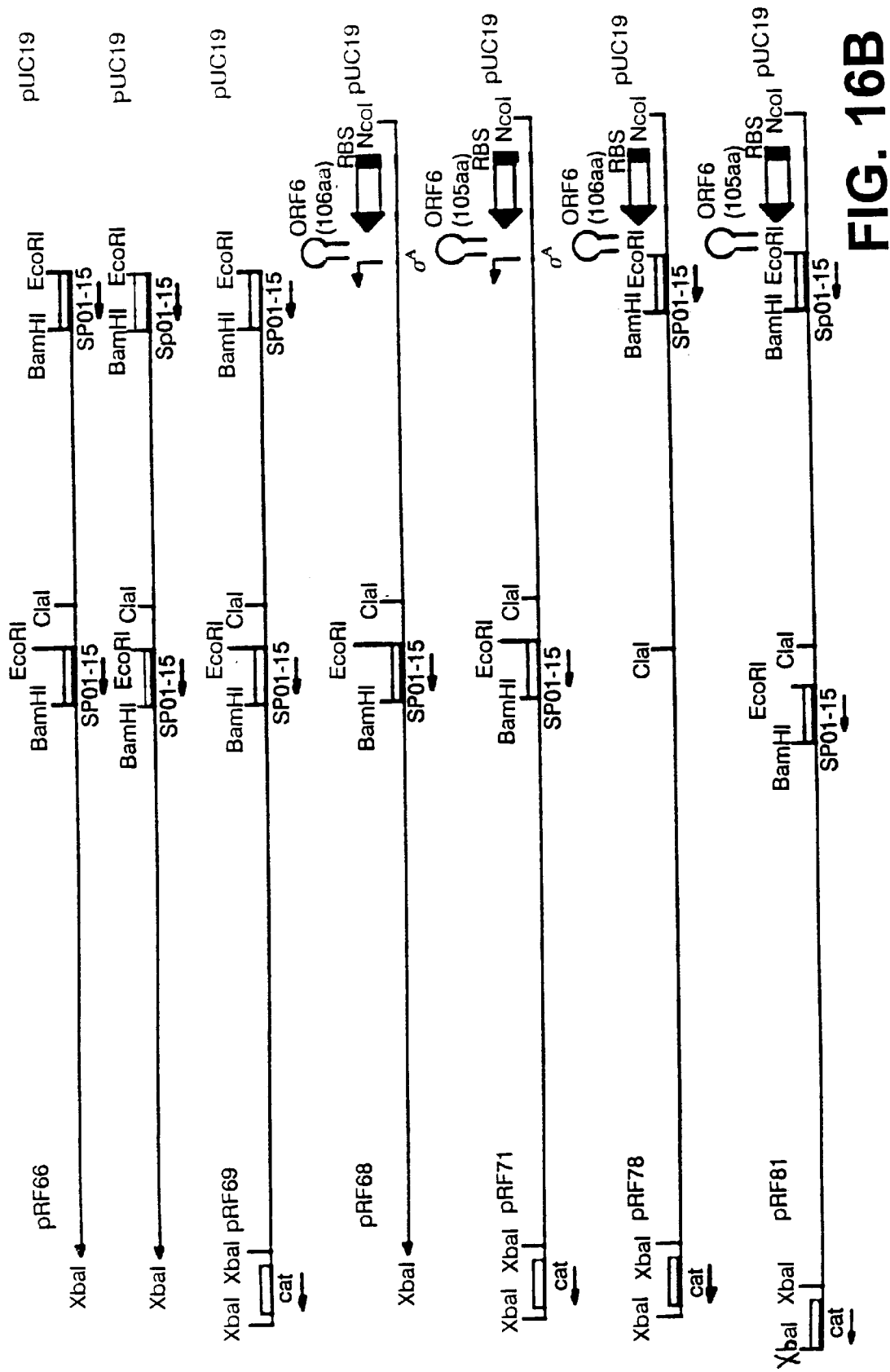

FIGS. 14, 15, and 16. Structure of various vectors.

Figure 17:
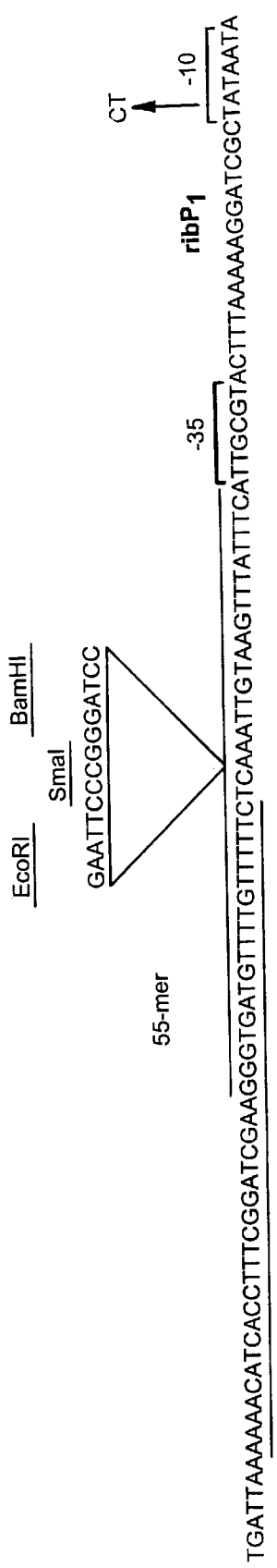

FIG. 17. 55-mer used in plasmid construction.

FIG. 18. Various oligonucleotides used in vector construction.

Host Bacteria

In the practice of the present invention, host bacterial strains are derived that contain one or more mutations in genes of the riboflavin biosynthetic pathway or in the biosynthetic pathway of various purines, which mutations lead to riboflavin overproduction. In one embodiment, such mutations lead to riboflavin overproduction by deregulating steps in the riboflavin biosynthetic pathway. In another embodiment, the mutations increase riboflavin production by causing an inhibition in the use in an alternative metabolic pathway of a precursor for riboflavin biosynthesis.

In a specific embodiment, desired mutations in the genetic background of the host bacteria can be induced by exposure to analogs of purine or riboflavin that compete with their authentic counterparts in the metabolic pathways of the host; bacteria that survive such exposure will have mutations that allow them to overproduce the authentic counterpart to the analog, thus "competing out" the purine or riboflavin analog that would otherwise be lethal. The biosynthesis of riboflavin in *B. subtilis* originates with guanosine triphosphate (FIG. 1, structure 1). Guanosine triphosphate (GTP), via guanosine monophosphate (GMP), is a product of the purine biosynthetic pathway (FIG. 2). In a preferred embodiment, to obtain a host strain that overproduces riboflavin, one can use classical genetics to both increase the amount of GTP that the cell produces and to deregulate the riboflavin pathway. Purine overproduction in *B. subtilis* can be achieved by obtaining mutants resistant to purine analogs or antagonists. Examples of some of the purine analogs that can be used include but are not limited to 8-azaguanine (Ishii and Shiio, *Agric. Biol. Chem.* 36:1511, 1972; Konishi and Shiro, *Agric. Biol. Chem.* 32:396, 1968), psicofuranine and decoyinine (Matsui et al., *Agric. Biol. Chem.* 43:1739, 1979; Matsui et al., *Agric. Biol. Chem.* 43:393, 1979), 8-azaxanthine, sulfaguanine, 6-thioguanine (Debabov, V. G. in *The Molecular Biology of the Bacilli* vol. 1 *Bacillus subtilis*, D. A. Dubnau, ed. (Academic Press, New York), pp. 331–370, 1982) and others, and/or the antagonist methionine sulfoxide (Matsui et al., *App. Env. Microbiol.* 34:337, 1977), and any combination thereof.

The riboflavin pathway can be deregulated by obtaining mutants resistant to a riboflavin analog. An example of a riboflavin analog that can be utilized is roseoflavin (Matsui et al., *Agric. Biol. Chem.* 46:2003, 1982).

In a specific embodiment of the present invention, bacteria that are mutationally resistant to the analogs azaguanine, decoyinine and roseoflavin, can be used. Specific mutants resistant to each of these compounds are described below. Bacteria with mutations rendering them resistant to other analogs can also be used. It is also deemed within the scope of the present invention to utilize bacteria with different mutations rendering resistance to these same analogs, or different combinations of these mutations, either in combination, with or without, various mutations to other analogs.

If exposure to the analog alone does not produce resistant mutants at a high enough frequency, various mutagens can be used to increase the frequency of mutation in general and thus increase the number of analog-resistant mutants. As one example, ethyl methyl sulfonate can be used, but other mutagens including but not limited to nitrosoguanidine or UV irradiation can also be used.

Suitable bacterial hosts include all Bacilli species (including in a preferred embodiment *B. subtilis*), *E. coli*, and many other gram-positive and gram-negative bacteria. Species which can recognize the promoter sequences of the cloned rib operon to be inserted within their genome are suitable for use. The plasmids described below can be used to introduce rib genes into other bacteria by standard procedure, e.g., transformation. Expression of the inserted rib genes can be determined by spectroscopy as described below, or by observation of the bacteria under UV light, as described below.

In addition to creating mutations by exposure to purine or riboflavin analogs, bacterial strains that already contain mutations that are known to affect their purine or riboflavin biosynthetic pathways can be utilized. For example, the present invention makes use of but is not limited to *B. subtilis* strain 1A382, which contains the mutation pur-60, making it auxotrophic for adenine. Because this mutation blocks the utilization of the riboflavin precursor inosine monophosphate (IMP) in a metabolic pathway other than riboflavin production, increased amounts of IMP are available for riboflavin biosynthesis, thus increasing riboflavin production. There are many other mutations which can be utilized to potentially increase riboflavin production, including but not limited to guaC3, his$^-$ and others that are included within the scope of the present invention. The guaC3 mutation prevents the conversion of GMP back into IMP (see FIG. 2), thus increasing the amount of riboflavin biosynthetic precursors available.

Suitable mutations affecting riboflavin overproduction can be mapped by various methods known in the art. In a specific embodiment, a mutation can be mapped by complementation of auxotrophic mutants.

Riboflavin Biosynthetic Genes

The riboflavin biosynthetic genes from various bacteria can be cloned for use in the present invention. Yeast or bacterial cells from species including but not limited to the genus Bacillus, *E. coli* and many other gram-positive and gram-negative bacteria can potentially serve as the nucleic acid source for the molecular cloning of the rib operon. The DNA containing the rib operon may be obtained, by standard procedures known in the art, for example, from a DNA library prepared by cloning chromosomal DNA or fragments thereof, purified from the desired bacterial cell, into a suitable vector for propagation of the gene. (See, for example, Maniatis et al., 1982, *Molecular Cloning, A Laboratory Manual*, Cold Spring Harbor Laboratory, Cold Spring Harbor, N.Y.; Glover, D. M. (ed.), 1982, *DNA Cloning: A Practical Approach*, MRL Press, Ltd., Oxford, U.K., Vol. I, II).

In the molecular cloning of the gene from chromosomal DNA, fragments are generated, some of which will encode the desired rib operon. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to agarose and polyacrylamide gel electrophoresis and density gradient centrifugation.

Once the DNA fragments are generated, DNA libraries are prepared using an appropriate cloning and/or expression vector. A large number of vector-host systems known in the art may be used. Possible vectors include, but are not limited to, plasmids or modified viruses, but the vector system must be compatible with the host cell used. For *E. coli* such vectors include, but are not limited to, bacteriophages such as λ derivatives, high-copy plasmids such as pBR322 or pUC plasmids, or low-copy plasmids derived from Pseudomonas plasmid RK2. For Bacillus such vectors include, but are not limited to, bacteriophages such as ρ11 (Dean et al., *J. Virol.* 20: 339, 1976; Kawamura et al., *Gene* 5:87, 1979) or φ105 derivatives (Iijima et al., *Gene* 9:115, 1980; Errington, *J. Gen. Microbiology* 130:2615, 1984; Dhaese et al., *Gene* 32: 181, 1984; Errington, J. in *Bacillus Molecular Biology and Biotechnology Applications*, A. T. Ganesan and J. A. Hoch, eds. (Academic Press, New York,), p. 217, 1986), high-copy plasmids such as pUB110 (Ehrlich, *Proc. Natl. Acad. Sci.* (*USA*) 74: 1680, 1977) or pBD64, or low-copy plasmids such as pE194 derivatives (Gryczan, T. J. in *The Molecular Biology of the Bacilli*, D. A. Dubnau, ed. (Academic Press, New York), pp. 307–329, 1982; Hoinouchi and Weisblum, *J. Bacteriol.* 150: 804, 1982). Recombinant molecules can be introduced into host cells via transformation, transfection, protoplasting, infection, electroporation, etc.

Once the DNA libraries are generated, identification of the specific clones harboring recombinant DNA containing the rib operon may be accomplished in a number of ways (as described, for example, in Maniatis et. al., supra). For example, if an amount of the operon or a fragment thereof is available from another bacterial source (e.g., from *E. coli*) and is sufficiently homologous to the riboflavin biosynthetic genes of Bacillus to hybridize thereto, that DNA can be purified and labeled, and the generated bank of DNA fragments may be screened by nucleic acid hybridization to the labeled probes (Benton, W. and Davis, R., 1977, *Science* 196:180; Grunstein, M. and Hogness, D., 1975, *Proc. Natl. Acad. Sci. U.S.A.* 72:3961). Alternatively, sequences comprising open reading frames of the endogenous rib operon, or subsequences thereof comprising about 10, preferably 15 or more nucleotides, may be used as hybridization probes. Such probes can be made synthetically, based on a portion of the nucleic acid or amino acid sequence (examples of which are provided below) of a gene product known to be encoded by the operon ("reverse genetics"). If a purified rib operon-specific probe is unavailable, cloned gene libraries of restriction fragments (from partial Sau3A-digests, for example) can be made in bacteria, especially *B. subtilis* or *E. coli*, and the rib operon-containing recombinant clones can be identified by either marker-rescue or complementation of known rib mutations.

In a preferred embodiment, the rib operon of *B. subtilis* can be isolated for use from an *E. coli* plasmid library of *B. subtilis* DNA. In particular, and as described below, the *B. subtilis* rib operon can be isolated by virtue of its homology to a radiolabelled, synthesized nucleotide probe that is derived from an internal region of a gene product known to be encoded by the operon of *B. subtilis*. Although a portion of the amino acid sequence for β-riboflavin synthase (Ludwig et al., *J. Biol. Chem.* 262:1016, 1987) can be the basis for such a probe, with the third nucleotide of each codon estimated from frequency of codon usage, a similar probe based on another region of this protein or another protein from the rib operon can be utilized and would fall within the scope of the present invention. The present invention further enables screening by use of synthetic probes which are derived from the nucleic acid sequence shown in FIG. 3.

Analogous methods to those detailed here can be used to isolate the rib operon of other bacteria, especially other Bacilli or *E. coli*. In a specific embodiment, such clones can be selected by assay for ability to hybridize to the labeled *B. subtilis* rib operon or a hybridizable portion thereof. It is well known in the art that starting from an appropriate mRNA preparation, cDNA can be prepared; such cDNA can also be used in accordance with the present invention to prepare vectors for the transformation of appropriate bacteria for riboflavin overproduction.

Once the host cells with recombinant DNA molecules that include the isolated rib operon or a portion thereof are identified, the DNA may be obtained in large quantities. This then permits the rib operon to be manipulated and its nucleotide sequence to be determined using various cloning and sequencing techniques familiar to those knowledgeable in the art.

For example, insertional mutagenesis can be used to locate and characterize the rib operon and genes thereof within a cloned piece of DNA. In a specific embodiment, rib-biosynthetic containing regions can be identified by inserting small cat (chloramphenicol acetyltransferase)-containing restriction fragments into several different restriction enzyme sites of the cloned DNA, and testing each derivative for insertional inactivation of riboflavin biosynthesis in an appropriate host (see below).

The cloned DNA corresponding to the rib operon can be analyzed by methods including but not limited to Southern hybridization (Southern, E.M., 1975, *J. Mol. Biol.* 98:503–517), Northern hybridization (see e.g., Freeman et al., 1983, *Proc. Natl. Acad. Sci. U.S.A.* 80:4094–4098), restriction endonuclease mapping (Maniatis et al., 1982, *Molecular Cloning, A Laboratory Manual*, Cold Spring Harbor Laboratory, Cold Spring Harbor, N.Y.), and DNA sequence analysis. Restriction endonuclease mapping can be used to roughly determine the genetic structure of rib operon. Restriction maps derived by restriction endonuclease cleavage can be confirmed by DNA sequence analysis.

DNA sequence analysis can be performed by any techniques known in the art, including but not limited to the method of Maxam and Gilbert (1980, *Meth. Enzymol.* 65:499–560), the Sanger dideoxy method (Sanger, F., et al., 1977, *Proc. Natl. Acad. Sci. U.S.A.* 74:5463), or use of an automated DNA sequenator (e.g., Applied Biosystems, Foster City, Calif.). As an example, the DNA sequence of the rib operon of *B. subtilis* is presented in FIG. 3.

Once the nucleotide sequence of the rib operon has been determined, putative open reading frames (ORFs) can then be identified along with the deduced amino acid sequence of their encoded product. Actual identification of the encoded product can be carried out, e.g., by performing S-30 coupled in vitro transcription/translation reactions, with various ORFs used as templates. Various mutational derivatives of the ORFs can also be tested for activity in functional assays of the S-30 reaction products, in order to test the function of the encoded products.

In a specific embodiment of the invention relating to the *B. subtilis* rib operon, and detailed in the examples below, the above-described methods were used to determine that *B. subtilis* riboflavin biosynthesis is controlled by a single operon of approximately 4.2 kb containing five biosynthetic genes: the β subunit of riboflavin synthase and ORFs designated 2, 3, 4, and 5 (see FIG. 4). ORFs 2, 3, 4, and 5 were subsequently shown to encode proteins with molecular weights of about 15 kd, 47 kd, 26 kd, and 44 kd, respectively. As described below, ORF 5 was shown to encode a putative rib-specific deaminase that catalyzes the reduction of a deaminated pyrimidine to a ribitylamino-linkage in an early step in riboflavin biosynthesis. Our data also indicated that ORF 4 encodes the α subunit of riboflavin synthase and ORF 3 encodes a GTP cyclohydrolase, while ORF 2 possibly encodes a rib-specific reductase. ORF 1 and ORF 6 were found to be outside the primary transcription unit of the rib operon. The primary site for initiation of transcription of the rib operon was determined to be probably the apparent $\sigma^A$ promoter located 290 bp upstream from the first gene in the operon, ORF 5 (FIG. 4, $P_1$). The coding regions, promoters and transcription termination sites of the *B. subtilis* rib operon are shown in Table VI below.

The present invention encompasses the nucleotide and amino acid sequences of the genes of the rib operon, as well as subsequences thereof encoding functionally active peptides, and sequences which are substantially the same as such sequences. A functionally active peptide, as used herein, shall mean a protein or peptide which is capable of catalysing a reaction leading to riboflavin biosynthesis. A functionally active nucleic acid sequence shall mean a sequence capable of regulating riboflavin biosynthesis. A sequence substantially the same as another sequence shall mean a sequence capable of hybridizing to the complementary sequence thereof. In addition, a nucleic acid sequence not naturally controlling the expression of a second nucleic acid sequence shall mean a sequence which does not control the expression of the second sequence in the bacterium from which the second sequence is isolated.

Once the genetic structure of the rib operon is known, it is possible to manipulate the structure for optimal use in the present invention. For example, the rib operon can be engineered to maximize riboflavin production.

Depending on the host-vector system utilized, any one of a number of suitable transcription and translation elements may be used. Promoters produced by recombinant DNA or synthetic techniques may also be used to provide for transcription of the inserted sequences. When propagating in bacteria the regulatory sequences of the rib operon itself may be used. In an embodiment in which the entire rib operon, or greater than one gene thereof, is desired to be expressed as a polycistronic message, a prokaryotic host is required. In an embodiment in which a eukaryotic host is to be used, appropriate regulatory sequences (e.g., a promoter) must be placed in the recombinant DNA upstream of each gene/ORF that is desired to be expressed.

Specific initiation signals are also required for efficient translation of inserted protein coding sequences. These signals include the initiation codon (ATG, GTG or TTG) and adjacent sequences, such as the ribosome binding site (RBS). It should be noted that the RBS of a given coding sequence can be manipulated to effect a more efficient expression of that coding sequence at the translational level. In cases where an entire open reading frame of the rib operon, including its own initiation codon and adjacent regulatory sequences, is inserted into the appropriate expression vectors, no additional translational control signals may be needed. However, in cases where only a portion of the coding sequence is inserted, or where the native regulatory signals are not recognized by the host cell, exogenous translational control signals, including the initiation codon, must be provided. The initiation codon must furthermore be in phase with the reading frame of the protein coding sequences to ensure translation of the entire insert. These exogenous translational control signals and initiation codons can be of a variety of origins, both natural and synthetic.

In addition, a host cell strain may be chosen which modulates the expression of the rib operon gene(s) or modifies and processes the gene product(s) thereof in the specific fashion desired. Expression from certain promoters can be elevated in the presence of certain inducers; thus, expression of the genetically engineered rib operon proteins may be controlled. In one embodiment, the regulatory regions of the operon, such as the promoter and the termination/anti-termination regulatory sequences, can be manipulated or replaced with constitutive or growth-regulated promoters to deregulate the rib operon and thus increase riboflavin production. Furthermore, appropriate cell lines or host systems can be chosen to ensure the desired modification and processing of the expressed proteins. Many manipulations are possible and within the scope of the present invention.

In one specific embodiment of the invention, the 5' regulatory sequence of the *B. subtilis* rib operon can be removed and replaced with one or more of several *B. subtilis* promoters; such a construction will cause high-level expression of the rib biosynthetic genes. This approach would involve the introduction of new restriction sites within a 20–30 bp region between the end of the transcription terminator and the RBS sequence of the first gene in the operon ORF 5. Such restriction sites can be introduced by either site-directed mutagenesis or by deleting all regulatory sequences upstream from the right-most BglII (BglII$_R$) site located within the first 30 bp of ORF 5 (see FIGS. 3 and 4) and inserting at this site a synthetic oligonucleotide that finishes off the 5' end of ORF 5 (including the ribosomal-binding site) and contains new upstream restriction sites. Once these constructions are made, promoter-containing restriction fragments with ends compatible to the new restriction sites can be introduced, causing expression of the rib genes under the control of the new promoter. Both constitutive and growth-regulated *B. subtilis* promoters can be used, including but not limited to strong promoters from the lytic bacteriophage SPO1 genes, veg, amy (amylase), and apr (subtilisin).

In another aspect of the invention, rib operon DNA fragments which have transcriptional regulatory activity (e.g., promoters) can be used to regulate the expression of heterologous gene products.

Introduction of rib operon into Bacterial Host

According to the present invention, the rib operon can be introduced into bacteria, including for example, Bacilli and *E. coli*, where it is expressed. In a preferred embodiment, the bacterial host is one of the mutant hosts described above. In a specific embodiment, the cloned rib operon is integrated into the host chromosomal DNA, where it is replicated and expressed along with host genomic DNA. In a most preferred embodiment, multiple copies of the rib operon are integrated into the host chromosomal DNA, thus providing for amplified expression of the rib operon in the deregulated host. One method in which this may be accomplished is chromosomal insertion of a cat-containing rib operon followed by chloramphenicol amplification of the operon, as detailed in the examples sections infra. One can also use a $tet^r$ gene, or certain other drug resistance genes that are expressed in Bacillus, with the same technique.

In specific embodiments, integration vectors containing the rib operon fragment can be engineered so as to contain the rib operon on the smallest possible DNA fragment, in an attempt to obtain greater amplification of the vector within the host chromosome. For example, vector DNA sequences may be deleted, and/or nonessential DNA flanking the rib operon can be deleted.

Riboflavin Production

In general, bacteria that are prototrophic for riboflavin survive on minimal medium in the absence of riboflavin. Production of riboflavin can be detected and quantified by various methods. In a preferred embodiment, overproduction of riboflavin is readily observed when overproducing bacteria are exposed to UV light at 366 nm, as described infra, producing an observable, yellow fluorescence. For example, many of the engineered plasmids of the present invention are produced in *E. coli*. For some of these plasmids, overproduction of riboflavin has been confirmed by this method. The amount of riboflavin produced can be quantitated, e.g., with reverse-phase high performance liquid chromatography (HPLC). Cell-free supernatants from bacteria can be fractionated over an HPLC column, as described infra, and monitored for riboflavin at 254 nm. By extrapolation from a standard curve, the concentration of riboflavin can be determined by the area of the peak on the chromatogram.

Riboflavin can also be quantitated by fluorescence spectrophotometry. For example, samples containing riboflavin can be read in a fluorescence spectrophotometer set at an emission wavelength of 525 nm and an excitation wavelength of 450 nm.

In addition, other methods known in the art are available to detect or quantitate riboflavin based on its physical and biological properties.

Fermentation

Riboflavin overproducing bacteria can be grown in vessels ranging from shake flasks to large "batch" fermentors, by methods known in the art (see below). In a preferred embodiment, nutrient feed can be manipulated to maximize riboflavin production at the minimum cost by varying the nutrients in the medium.

In a specific embodiment, amplified rib-containing genes can be maintained at high-copy number in the bacterial chromosome by the inclusion of about 60 μg/ml chloramphenicol in the inoculum seed strain (but not necessarily in the fermentor). Chemap 14-liter fermentors can be used at 1000 rpm with a head pressure of 0.6 atmospheres.

The cells (especially recombinant bacteria as specifically mentioned herein) are grown under suitable growth conditions. Such suitable growth conditions are characterized by limiting the availability of a component of the growth medium and/or feed medium in such a way that aerobic conditions for the growth of said recombinant bacterium are maintained. Such conditions can be also characterized e.g. by maintaining a level of dissolved oxygen at a concentration between about 5% to 30%. One skilled in the art is familiar with the fact that such levels of dissolved oxygen can vary dependent on the specific technical equipment used for growing said recombinant bacteria and for measuring said dissolved oxygen concentration. Under anaerobic conditions the synthesis of riboflavin is reduced. In some embodiments, the limiting component is chosen from a carbon source, nitrogen source, or a component required by the cells (e.g., in the feed medium). For example, if the cells are auxotrophic, for example, for methionine, a limiting level of methionine may be provided in the growth medium. In another example, such component could be glucose or a carbonic acid, e.g. a citric acid cycle acid, such as citric acid or succinic acid, or an amino acid.

EXAMPLE 1

Riboflavin-Overproducing *B. subtilis* Mutants

We describe in the examples herein the production of strains of *Bacillus subtilis* which overproduce riboflavin. In order to accomplish this, we used classical genetics, genetic engineering, and fermentation. Classical genetics with selection using purine and riboflavin analogs was used to deregulate the pathways for purine (riboflavin precursor) and riboflavin biosynthesis. Riboflavin production was increased further by cloning and engineering the genes of the riboflavin biosynthetic pathway (the rib operon), allowing for constitutive, high-level production of rate-limiting biosynthetic enzyme(s).

The biosynthesis of riboflavin in *B. subtilis* originates with GTP (FIG. 1). To obtain a host that overproduces riboflavin we used classical genetics to both increase the amount of GTP that the cell produces and to deregulate the riboflavin pathway. Purine overproduction in *B. subtilis* can be achieved by obtaining mutants resistant to purine analogs such as azaguanine and decoyinine, and other antagonists such as methionine sulfoxide (see e.g., Ishii and Shiio, *Agric. Biol. Chem.* 36(9):1511–1522, 1972; Matsui et al., *Agric. Biol. Chem.* 43(8):1739–1744, 1979). The riboflavin pathway can be deregulated by obtaining mutants resistant to the riboflavin analog roseoflavin (Matsui et al., *Agric. Biol. Chem.* 46(8):2003–2008, 1982). Roseoflavin-resistant strains were selected from several strains which had been previously mutagenized and which were resistant to several purine analogs. Described below are the methods used to produce a strain (RB50) which overproduces riboflavin.

8-Azaguanine-Resistant Mutants

*B. subtilis* is effectively killed by the purine analogue 8-azaguanine (Sigma Chemical Co., St. Louis, Mo.) at a concentration of 500 μg/ml, and resistant mutants appear spontaneously at a frequency of less than 1 in $10^8$. Ethyl methyl sulfonate (EMS; Sigma) at 30 μg/ml was used as a mutagen to increase the frequency of azaguanine-resistant ($Ag^r$) mutations. Mutagenesis was performed on cells from *B. subtilis* strain 168 by standard procedures (Miller, 1972, *Experiments in Molecular Genetics*, Cold Spring Harbor Laboratory, Cold Spring Harbor, N.Y.). After plating 4×10⁶ mutagenized cells on minimal medium (Sloma et al., *J. Bact.*

170:5557, 1988) containing 500 μg/ml azaguanine and restreaking for single colonies, 35 $Ag^r$ colonies resulted. One mutant, RB11 ($Ag^r$-11), was used in the construction of RB50.

Decoyinine-Resistant Mutants

Decoyinine-resistant ($Dc^r$) mutations were obtained spontaneously at a frequency of 1 in $10^6$ or after EMS mutagenesis at 1 in $10^5$ by plating cells on minimal medium containing 100 μg/ml of decoyinine (Upjohn Co., Kalamazoo, Mich.). A $Dc^r$ mutant of RB11 was obtained by mutagenesis with EMS as described above. One $Dc^r$ colony, RB15 ($Ag^r$-11, $Dc^r$-15), was used in the construction of RB50.

Transfer of the Ag and Dc Mutations

These purine analog-resistant mutations were transferred to a different strain background in order to isolate them from any unwanted EMS-induced mutations and to verify that the $Ag^r$ and $Dc^r$ mutations were due to single loci. Since part of the "carbon flow" from inosine monophosphate (IMP), a riboflavin precursor, is also used for adenine nucleotide biosynthesis, a host strain was selected that was blocked in the adenosine monophosphate (AMP) pathway via the mutation pur-60, allowing more carbon material to "flow" from IMP to the guanine nucleotide precursors of riboflavin (FIG. 2). *B. subtilis* strain 1A382 (hisH2, trpC2, pur-60) was made competent (Sloma et al., *J. Bact.* 170:5557 (1988)) and transformed (by the method of Gryczan et al., *J. Bact.* 134:318 (1978)) with total DNA prepared from the $Ag^r$/$Dc^r$ mutant RB15. The $Trp^+$ (tryptophan) revertant colonies were selected, with 3.3% (10/300) of those also being $Dc^r$ and 2.3% (7/300) $Ag^r$. This result was not unexpected since, due to "congression" (transformation of a second unlinked marker), a number of the $Trp^+$ colonies should also be resistant to decoyinine or azaguanine.

One $Dc^r$ colony, RB36 (his H2, pur-60, $Dc^r$-15), one $Ag^r$ colony, RB40 (his H2, pur-60, $Ag^r$-11), and one $Dc^r$/$Ag^r$ colony (which was also found to be his$^+$), RB39 (pur-60, $Ag^r$-11, $Dc^r$-15), were all selected for further study.

Methionine Sulfoxide-Resistant Mutants

Selection using high levels of methionine sulfoxide (MS; 10 mg/ml, Sigma) resulted in spontaneous mutants appearing at a sufficiently high frequency that mutagenesis with EMS was not necessary. The $Ag^r$/$Dc^r$ mutant, RB39, was streaked onto minimal medium containing 10 μg/ml MS. Resistant colonies were obtained and were restreaked for single resistant colonies. One strain, RB46 (pur-60, $Ag^r$-11, $Dc^r$-15, $MS^r$-46) was selected for further study.

Roseoflavin Resistant Mutants

Although many of these $Ag^r$, $Dc^r$ and $MS^r$ mutants were likely to be overproducing GTP, none of them produced levels of riboflavin detectable on plates. In order to deregulate the riboflavin biosynthetic pathway, conditions were determined to select for resistance to the riboflavin analog roseoflavin (Toronto Research Chemical). Maximum killing of cells occurred at 100 μg/ml of roseoflavin in minimal or complete medium; increasing the concentration did not result in any additional killing. Mutations to roseoflavin resistance ($RoF^r$) spontaneously occurred at a sufficiently high rate (approximately $5 \times 10^{-5}$) such that mutagenesis with EMS or other chemicals was not necessary.

Approximately 1000 $RoF^r$ colonies were obtained from each of the strains described above, 1A382, RB36, RB39, RB40 and RB46. $RoF^r$ mutants from all of these strains showed a low level of fluorescence on minimal media plates when exposed to long-wave UV light (366 nm), indicating some riboflavin production. One of the $RoF^r$ colonies obtained from RB46, RB46Y (pur-60, $Ag^r$-11, $Dc^r$-15, $MS^r$-46, $RoF^r$-46), when grown on minimal medium, produced 14 mg/l of riboflavin as determined by HPLC (described above).

Of all the strains treated, only RB39 and RB46 produced a significantly different phenotype when $RoF^r$ colonies were selected. Approximately 0.5% to 1.0% of the $RoF^r$ colonies of either RB39 or RB46 produced an intensely fluorescent, yellow colony. Of these colonies, RB51 (pur-60, $Ag^r$-11, $Dc^r$-15, $RoF^r$-51), arising from RB39, and RB50 (pur-60, $Ag^r$-11, $Dc^r$-15, $MS^r$-46, $RoF^r$-50), arising from RB46, produced a stable, fluorescent-yellow phenotype which correlated with a higher level of riboflavin production, as determined by HPLC. When grown in minimal medium, both RB50 and RB51 produced higher levels of riboflavin in their supernatants than the other $RoF^r$ strains, about 40 mg/l and 30 mg/l, respectively. The lineage of RB50 is depicted in FIG. 5.

Because intensely fluorescent (and thus riboflavin overproducing) colonies could be obtained in non-$MS^r$ strains such as RB51, it appeared that this mutation in general might not be contributing significantly to the higher production phenotype. Both of the other mutations, $Ag^r$ and $Dc^r$ ($Ag^r$-11 and $Dc^r$-15 in RB39), appear to be necessary to produce high levels of riboflavin since no intensely fluorescent $RoF^r$ colonies could be found in strains containing only the $Ag^r$-11 (from RB40) or $Dc^r$-15 (from RB36) mutation alone.

guac Mutations

Another possibly important mutation for achieving overproduction of GTP, and thus riboflavin, is guaC3, which prevents the conversion of GMP back into IMP (see FIG. 2). To construct a strain containing guaC3 that overproduces riboflavin, competent *B. subtilis* strain 62121 cells (guaC3, trpC2, metC7) (Endo et al., *J. Bact.* 15: 169, 1983) were transformed with RB50 DNA and selected for $Dc^r$ on plates containing 100 μg/ml of decoyinine. Thousands of $Dc^r$ colonies resulted. Of 200 colonies which were patched onto $Dc^r$ plates, one was found that exhibited the riboflavin overproduction phenotype (based on UV fluorescence), and was $RoF^r$. This colony was designated RB52 (guaC3, trpC2, metC7, $Dc^r$-15, $RoF^r$-50) and was reserved for subsequent study.

Other Analog-Resistant Mutants

Finally, because mutants resistant to several additional purine analogs also have been reported to be altered in purine metabolism, such mutations were assayed in order to investigate their effect on riboflavin-overproducing strains. It was determined that 500 g/ml of 8-azaxanthine, 1 mg/ml of 6-thioguanine, or 2 mg/ml of sulfaguanidine (Sigma) effectively kills wild-type *B. subtilis*. The azaguanine-resistant, riboflavin-overproducing strains RB50::[pRF8]$_{90}$ and RB53::[pRF8]$_{90}$ (see below) were found to be already resistant to azaxanthine. Although separate azaguanine- and azaxanthine-resistant mutations with different properties have been described previously, in this case the $Ag^r$-11 and $Ag^r$-53 mutations appear to also convey azaxanthine resistance.

HPLC Analysis of riboflavin in crude supernatants of *B. subtilis*

Accumulation of riboflavin in *B. subtilis* cultures was quantitated by reverse-phase HPLC. Riboflavin standards (Sigma Chemical Co., St. Louis, Mo.) or cell-free supernatants from strains to be tested were fractionated over a 4.6 mm×250 mm Vydac $C_{18}$ column equilibrated with 1% ammonium acetate (pH 6.0). At injection, the column was developed with a linear gradient of methanol and monitored for riboflavin at 254 nm. Authentic riboflavin (i.e. riboflavin "standard") elutes at the mid-point of the gradient.

EXAMPLE 2

Cloning B. subtilis rib operon

Our general strategy to isolate a restriction fragment containing the rib operon was to screen a "mini" E. coli plasmid library of B. subtilis DNA by hybridization with a synthetic oligonucleotide probe, the DNA sequence of which was partially derived from the published amino acid sequence for the β subunit of riboflavin synthase (Ludwig et al., J. Biol. Chem. 262:1016, 1987). A summary of the protocol is presented in FIG. 6.

A synthetic, 54-base "guess-a-mer" oligonucleotide probe was used for this screening based on amino acids 84–102 of the 240 amino acid riboflavin synthase protein, sequenced by Ludwig et al. (J. Biol. Chem. 262:1016–1021, 1987). The third nucleotide of each codon in the probe was chosen according to estimates made of the most frequent codon usage of B. subtilis, based upon, for example, some of the sequences available in GenBank® (Los Alamos Nat. Lab, Los Alamos, N.Mex.). The probe consisted of the following sequence:

5'-GGAGCTACAACACATTATGATTATGTTTGCAAT-GAAGCTGCTAAAGGAATTGCT-3'. To test the specificity of the probe, the $^{32}$P-labelled 54-mer DNA was hybridized to nylon filters containing EcoRI-digested chromosomal DNA (Southern, J. Mol. Biol. 98:503, 1975) isolated from wild-type and the mutant B. subtilis strains. The probe strongly hybridized to a single 9–10 kb fragment of EcoRI-digested B. subtilis (rib$^+$ met$^-$) DNA, which is in good agreement with the predicted size of the rib-containing fragment (Osina et al., FEBS. Lett. 196:75, 1986). A labelled fragment of the identical size was detected when the probe was hybridized to two mutant strains, RB46 (pur-60, Ag$^r$-11, Dc$^r$-15, MS$^r$-46) and RB50 (pur-60, Ag$^r$-11, Dc$^r$-15, MS$^r$-46, RoF$^r$-50), the latter being a riboflavin overproducer. These hybridization experiments were repeated using HindIII-cut chromosomal DNA, which resulted in the probe identifying a smaller, single fragment of approximately 1.8 kb; this latter result was useful in determining the general location of the rib biosynthetic operon within the cloned DNA.

Isolation of Plasmids pRF1, pRF2 and PRF3, Containing Wild-type rib Biosynthetic Genes A "mini" gene library of 9–11 kb EcoRI fragments from B. subtilis strain 168 (rib+) DNA was prepared using pRK290, a low-copy number vector derived from the Pseudomonas replicon RK2 (Ditta et al., Plasmid 13:149, 1985). EcoRI fragments (size 9–11 kb) of B. subtilis (rib$^+$ met$^-$) DNA were isolated by sucrose (10–40%) rate-zonal centrifugation. A four-fold excess of these fragments (0.22 µg) was ligated to EcoRI-cut pRK290 (0.26 µg), that had been dephosphorylated with calf intestinal alkaline phosphatase (CIAP), at a total DNA concentration of 10 µg/ml. Approximately 10 ng of ligated DNA was transformed into E. coli DH5 (F-, endA1, hsdR11 [r$_k$-, m$_k$+], supE$_{44}$, thi-1, λ-, recA1, gyrA96, relA1), resulting in tetracycline-resistant (Tc$^r$) colonies at a frequency of 7.7×10$^4$/µg of DNA. To determine the fraction of transformants containing insert DNA of 9–11 kb, plasmid mini-lysates were prepared from several Tc$^r$ transformants, and their DNA was analyzed by restriction enzyme digestion. About 40% of the Tc$^r$ transformants were found to contain single EcoRI-generated inserts of 9–11 kb.

Approximately 1140 of the Tc$^r$ colonies were screened with the $^{32}$P-labelled 54-mer probe specific for the riboflavin synthase gene. One colony gave a positive signal. Plasmid DNA, designated pRF1, was isolated from this clone and tested for Rib$^+$-marker rescue activity by transforming the DNA into B. subtilis 1A210 that contains the riboflavin-deficient mutation rib-2, and selecting for Rib$^+$ prototrophic colonies. pRF1 transformed 1A210 to Rib$^+$ prototrophy at a high frequency. Plasmid DNA from a randomly chosen Tc$^r$ transformant failed to rescue this marker.

Restriction enzyme analysis revealed that pRF1 actually contained two EcoRI-fragment inserts, of 10 kb and 11 kb. To determine which fragment contained the rib operon, EcoRI-digested pRF1 was probed with the $^{32}$P-labelled, 54-mer riboflavin synthase probe. The results indicated that only the smaller, 10 kb fragment cross-reacted with the probe. Moreover, when the 10 kb EcoRI fragment was recloned into the EcoRI site of pBR322, recombinant plasmids pRF2 and pRF3 resulted, representing the two possible orientations of insertion. Both plasmids were found to rescue the rib-2 mutation of B. subtilis 1A210 to prototrophy at a high frequency.

Isolation of Plamsids pRF6 and pRF7 Containing rib Biosynthetic Genes From RoF$^r$-B. subtilis Strain RB50

RB50 is one of the RoF$^r$ mutants of B. subtilis, produced as described above, that is deregulated for riboflavin biosynthesis. It has been reported that approximately 80% of RoF$^r$ mutations reside within the rib operon at the ribO locus (Stepanov, et al., Genetika (USSR) 13:490, 1977). Like the wild-type rib operon, rib genes in RB50 were also contained on a 9–10 kb EcoRI fragment; thus this fragment was cloned using the protocol outlined in FIG. 6, with pBR322 used as the cloning vector. Size-selected 9–11 kb EcoRI fragments (0.1 µg) from RB50 were prepared as before and ligated to a two-fold excess of ends of EcoRI-cut, dephosphorylated pBR322 DNA (0.34 µg) at a total DNA concentration of 22 µg/ml. Approximately 9 ng of ligated DNA was transformed into E. coli DH5, resulting in ampicillin-resistant (Ap$^r$) colonies at a frequency of 3.5×10$^5$/µg of DNA.

Restriction enzyme analysis of plasmid DNA isolated from a sampling of 12 Ap$^r$ colonies revealed that 50% contained plasmids with 9–11 kb EcoRI inserts. Approximately 1140 Ap$^r$ colonies were screened with the $^{32}$P-labelled 54-mer probe specific for the riboflavin synthase gene by colony hybridization. Six colonies gave positive signals. Plasmids pRF6 and pRF7, isolated from two of these six colonies, were identified by restriction enzyme analysis as containing inserts with the same orientation as pRF2 and pRF3, respectively. In addition, both plasmids were able to marker-rescue the rib-2 mutation at high frequencies.

EXAMPLE 3

Introducing rib$^+$ DNA Into B. subtilis

As described supra, the rib operon from both a wild-type strain and a RoF$^r$ mutant of B. subtilis were cloned as identical 10 kb EcoRI fragments into the EcoRI site of the E. coli replicon pBR322; the derivation of these recombinant plasmids is schematically diagrammed in FIG. 6. To introduce the 10 kb EcoRI fragment containing the rib operon into B. subtilis in multiple copies, and thus further increase riboflavin production, we constructed a plasmid vector which would allow integration into the B. subtilis chromosome. The integrated DNA was amplified by selecting colonies that would grow at high drug concentrations of chloramphenicol.

Construction of and Transformation with Integrational rib Plasmids pRF4 and pRF8

To construct the integrational vector, the drug-resistance gene chloramphenicol acetyltransferase (cat), which is selectable in B. subtilis, was introduced into pRF2 and pRF6, the pBR322 vectors with the 10 kb fragment from wild-type or RoF$^r$ B. subtilis strains, respectively. The plasmids pRF2 and pRF6 were digested with BamHI, which cuts the plasmids uniquely within the pBR322 sequence, and dephosphorylated with CIAP. The cleaved DNA was ligated to a 1.3 kb BamHI fragment containing the cat gene (Youngman et al., *Plasmid* 12: 1–9, 1984), and the ligated DNAs then transformed into *E. coli* DH5 cells (Hanahand, *J. Mol. Biol.* 166: 557, 1983). Approximately 80–90% of the Ap$^r$ transformants were chloramphenicol resistant (Cm$^r$); restriction analysis of the isolated plasmids (Maniatis et al.) confirmed that plasmid DNA from the Cm$^r$ colonies contained the 1.3 kb fragment. The plasmid containing the wild-type riboflavin fragment and the cat gene was designated pRF4; the plasmid containing the cloned riboflavin fragment from the RoF$^r$ strain was called pRF8. (Since the RoF$^r$ mutation was subsequently shown to be outside the rib operon, these plasmids are presumably identical).

The plasmids pRF4 and pRF8 were transformed into four different *B. subtilis* strains: the riboflavin overproducer RB50 (Ag$^r$-11, Dc$^r$-15, MS$^r$-$_{46}$, RoF$^r$-50), the RB50 parent RB46 (Ag$^r$-11, Dc$^r$-15, MS$^r$-$_{46}$), the RB50 parent 1A382, and IS75, a common laboratory strain. Competent IS75 and 1A382 cells were transformed with pRF4 or pRF8; these same plasmids were introduced into RB46 and RB50 by transformation of protoplasts (Chang and Cohen, *Mol. Gen. Genet* 168:111–115, 1979). The pRF4 or pRF8 DNA integrated into each of these four strains was amplified by selecting for colonies that grew at higher chloramphenicol concentrations. In each strain, we were able to obtain colonies that grew in up to 60 μg/ml of chloramphenicol.

In addition, RB52 (guac3, trpC2, metC7 Dc$^r$-15, RoF$^r$-50), produced by transforming the quaC3 *B. subtilis* strain 62121 with DNA from RB50, was made competent and transformed with pRF8. The integrated plasmid in one of the many Cm$^r$ colonies that resulted was amplified using 90 μg/ml of chloramphenicol. The resulting cells, RB52::[pRF8]$_{90}$, were grown to mid-log phase and plated on minimal media containing 500 μg/ml azaguanine. Approximately 20 Ag$^r$ colonies resulted. One such colony seemed to produce a more intense fluorescence. The lineage of this strain, RB53::[pRF8]$_{90}$, is given in FIG. 7.

EXAMPLE 4
Riboflavin Overproduction by Strains Containing pRF4 or pRF8

RB50 containing pRF4 or pRF8 displayed the riboflavin overproduction phenotype (yellow and UV-fluorescent colonies). Amplification of the rib$^+$ DNA in a wild-type strain or the parent strains of RB50 did not yield yellow or UV-fluorescent colonies, a finding that indicates that the RoF$^r$ mutation (which deregulates the biosynthesis of riboflavin) is required for chromosomal amplification of wild-type DNA to cause riboflavin overproduction. A series of shake flask fermentations were performed in 25 ml of riboflavin minimal medium (RMM, in Table I) in a 300 ml baffled flask (Bellco) to measure the production of riboflavin from RB50 that contained the integrated and amplified rib operon.

TABLE I

| COMPOSITION OF MEDIA | |
| --- | --- |
| RMM | g/l |
| Sodium glutamate | 2.0 |
| Casamino acids (Difco) | 0.2 |
| Yeast extract (Difco) | 0.2 |

TABLE I-continued

| COMPOSITION OF MEDIA | |
| --- | --- |
| RMM | g/l |
| KH$_2$PO$_4$ | 6.0 |
| K$_2$HPO$_4$ | 14.0 |
| (NH$_4$)$_2$SO$_4$ | 2.0 |
| Sodium citrate | 1.0 |
| MgSO$_4$.7H$_2$O | 0.2 |
| Adenosine | 0.05 |
| (adjusted to pH 7.0 and autoclaved) | |
| Maltose | 15.0 |
| (added as sterile 20% solution after autoclaving) | |

The fermentations were run with strains RB46, RB50 and RB50 containing pRF4 amplified by selection for resistance to 30 μg/ml of chloramphenicol (RB50::[pRF4]$_{30}$) and 90 μg/ml of chloramphenicol (RB50::[pRF4]$_{90}$). At 24 and 48 hours, supernatant samples were removed and measured for riboflavin content by reverse-phase HPLC.

As shown in Table II, RB50::[pRF4]$_{30}$ produced 0.3 g/l of riboflavin, and RB50::[pRF4]$_{90}$ produced 0.7 g/l of riboflavin, in 48 hours, which is significantly more than that produced by the strains without rib amplification, such as RB46 and RB50.

TABLE II

QUANTITATIVE ANALYSIS OF RIBOFLAVIN-CONTAINING SUPERNATANTS FROM *B. SUBTILIS*

| Strain | Culture Time (hours) | Riboflavin* (g/l) |
| --- | --- | --- |
| RB46 | 24 | 0.009 |
| RB50 | 24 | 0.02 |
| RB50::[pRF4]$_{30}$ | 24 | 0.1 |
| RB50::[pRF4]$_{90}$ | 24 | 0.4 |
| RB46 | 48 | 0.007 |
| RB50 | 48 | 0.05 |
| RB50::[pRF4]$_{30}$ | 48 | 0.3 |
| RB50::[pRF4]$_{90}$ | 48 | 0.7 |

*Riboflavin was measured using an HPLC assay.

The dramatic increase in riboflavin production resulting from amplification of rib genes in the deregulated host argues that information encoded by the cloned DNA is rate-limiting for riboflavin biosynthesis.

EXAMPLE 5
Mapping the RoF$^r$-50 Mutation

The RoF$^r$-50 mutation in RB50 appeared to be critical to the riboflavin-overproduction phenotype. To identify and possibly move the mutation into different strain backgrounds it was necessary to map the location of the RoF$^r$-50 mutation on the *B. subtilis* chromosome. Since pRF4 and pRF8 gave very similar levels of riboflavin production in all strain backgrounds, it seemed unlikely that the RoF$^r$-50 mutation was located on the cloned 10 kb EcoRI, rib-containing fragment. More likely, the RoF$^r$-50 mutation is an unlinked repressor-type mutation, possibly in ribC, a repressor mutation which has been reported to map in the lys-aroD region of the *B. subtilis* chromosome (Chernik et al., *Genetika* (USSR) 15:1569, 1979). To determine whether the RoF$^r$-$_{50}$ mutation was linked or unlinked to the riboflavin operon, competent *B. subtilis* 1A210 (rib-2) cells were transformed with RB50 DNA, selecting for rib$^+$. Thousands of rib$^+$ colonies resulted, and 200 colonies were patched onto tryptose blood agar base containing 100 g/ml of roseoflavin. No RoF$^r$ colonies resulted, and none of the colonies exhibited the riboflavin overproduction phenotype, confirming that the RoF$^r$-$_{50}$ mutation is not located in the rib operon.

EXAMPLE 6
Locatinq rib$^+$ Biosynthetic Genes Using CAT Insertional Mutagenesis FIG. 4 contains a restriction map of the rib-containing 10 kb EcoRI fragment of pRF2, prepared according to standard procedures. Restriction enzyme sites for XbaI, BglII, SstI, HpaI and NcoI are unique to the insert DNA, whereas SalI and PstI cut once in the insert and once in the vector; the insert does not contain any BamHI, XhoI or NheI restriction sites. Restriction enzyme HindIII cleaves the insert at multiple sites; the 54-mer probe specific for the riboflavin synthase gene hybridized to an approximately 1.8 kb HindIII fragment, suggesting that the rib operon must also reside in the general area surrounding the SalI and left-most BglII (BglII$_L$) sites.

In general, to determine the boundaries of the rib operon, small cat-containing restriction fragments were used to construct insertions and deletions in the rib+-cloned DNA fragment of pRF2.

E. coli plasmid pEcc1 served as the primary source of restriction fragments bearing a cat gene which confers chloramphenicol-resistance in both E. coli and B. subtilis. This plasmid, a derivative of pMI1101 (Youngman et al., Plasmid 12:1–9, 1984) in which a non-essential region of the plasmid was removed by standard recombinant DNA techniques, contains a 1.3 kb cat-containing fragment flanked by the "polylinkers" of M13mp7, and therefore is capable of generating cat cassettes with either SmaI, EcoRI, SalI, or BamHI ends. To generate SstI or XbaI-ended fragments containing the cat gene, the 1.3 kb cat-containing BamHI fragments of pEcc1 was isolated, the ends modified with HindIII linkers, and the modified fragment cloned into the HindIII site within the polylinker region of pIC10R, generating plasmid pEcc4.

Integrative plasmid derivatives were first constructed in E. coli and then transferred to the rib chromosomal locus of B. subtilis by DNA transformation. This was done by linearizing the plasmid by a restriction enzyme cut outside the cloned DNA insert, transforming competent B. subtilis strain 1A382 or PY79 (SPβ$^c$, SPβ$^c$ rib$^+$) cells with this cut DNA, and selecting for Cm$^r$. Because the pBR322 replicon is unable to replicate in B. subtilis, and the cat gene is bounded on both sides by sequences homologous to the rib$^+$ locus, the cat-containing insertion or deletion can only be inserted into the chromosome by a double-crossover recombination event to yield Cm$^r$ transformants. To determine whether the insertion or deletion inactivated riboflavin synthesis, Cm$^r$ colonies were assessed for growth on minimal medium agar plates with or without the presence of riboflavin (Rib phenotype).

As diagrammed in FIG. 8, cat-containing restriction fragments were inserted by ligation into the individual restriction sites for XbaI, SstI, SalI and BglII of pRF2, inserted between the pair of BglII or NcoI sites (generating deletions removing either a 2.0 kb BglII fragment or a 0.8 kb NcoI fragment) or inserted into single HaeIII and EcoRV sites of the approximately 1.8 kb HindIII fragment that hybridized to the rib-specific DNA probe, according to standard techniques. The results are shown in Table III.

TABLE III

CHARACTERIZATION OF INSERTION AND DELETION DERIVATIVES OF rib$^+$ DNA

| | B. subtilis$^b$ Riboflavin Phenotype |
|---|---|
| Insertion derivative$^a$ | |
| A (XbaI) | |
| r | + |
| l | ND |
| B (SstI$_L$) | |
| r | + |
| l | ND |
| C (SstI$_R$) | |
| r | — |
| l | — |
| D (BglII$_L$) | |
| r | — |
| l | — |
| E (SalI) | |
| r | — |
| l | — |
| F (BglII$_R$) | |
| r | — |
| l | — |
| G (HaeIII) | |
| r | ND |
| l | + |
| H (EcoRV) | |
| r | + |
| l | ND |
| Deletion derivative | |
| Bgl | |
| r | — |
| l | — |
| Nco | |
| r | + |
| l | + |

$^a$"r" (right) and "l" (left) identify the transcriptional orientation of the inserted cat gene relative to the restriction map in FIG. 8.
$^b$B. subtilis strain 1A382 (rib$^+$, trpC2, pur-60, hisH2) or PY79 (SP β$^c$, rib$^+$)

As summarized in FIG. 8 and Table III, insertions into the SalI, either BglII, or the "right most" SstI (SstI$_R$) sites, or deletion of the 2.0 kb BglII fragment, all generated Cm$^r$ colonies that could not produce riboflavin (Rib$^-$), indicating that the rib operon was centrally located within the cloned DNA. Significantly, removal of the 0.8 kb NcoI fragment apparently had no effect on riboflavin production (Rib$^+$), suggesting that one end of the rib gene cluster was located to the left of the "left most" NcoI (NcoI$_L$) site. The other end of the rib operon was initially determined to map within the approximately 1.8 kb HindIII fragment because the two insertions at sites within the fragment, EcoRV and HaeIII, as well as sites distal to the fragment, XbaI and SstI$_L$, all generated Cm$^r$ colonies that produced riboflavin.

EXAMPLE 7
Nucleotide Sequence of the rib operon

Based on the cat-insertional mutagenesis of the cloned 10 kb DNA fragment, the entire rib operon was localized within a 6.0 kb region bounded by the SstI$_L$ and NcoI$_L$ sites.

This 6.0 kb region of pRF2 containing the rib operon and flanking regions was sequenced by the dideoxy method of Sanger et al. (*Proc. Natl. Acad. Sci. USA* 74:5463, 1977). Briefly, M13 clones for sequencing were prepared either by subcloning specific restriction fragments into M13, by using the exonuclease activity of T4 DNA polymerase to generate a series of overlapping deletions (Dale et al., *Plasmid* 13:31, 1985), or by "shot-gun" cloning random fragments, from sonicated restriction fragments, into M13. In some cases, the nucleotide sequence across a restriction site juncture of adjacent fragments was also determined by primer extension sequencing. Approximately 5500 bp were sequenced on both strands and analyzed for sequences resembling typical open reading frames with gram positive-bacteria ribosome binding sites, gram-positive promoters and rho-independent transcription termination sites.

Analysis revealed six complete, non-overlapping open reading frames (FIG. 3): ORF 2 (124 amino acids), the gene coding for the β subunit of riboflavin synthase (154 amino acids), ORF 3 (398 amino acids), ORF 4 (215 amino acids), ORF 5 (361 amino acids) and ORF 6 (105 amino acids). Each ORF was preceded by a strong Bacillus ribosome binding site (RBS) with calculated thermostability ranging from $\Delta G=-16$ to $-22$ kcal/mol, and all of them were oriented in the same transcriptional direction. In addition, within the coding region of ORF 5, a second RBS site and ATG start codon were identified, potentially encoding a smaller protein of 248 amino acids. However, based on S-30 in vitro coupled transcription/translation reactions (see below), ORF 5 appears to encode only a 361 amino acid protein. Finally, part of another coding region, ORF 1, encoding the last 170 amino acids of a protein and oriented in the opposite direction, was also identified.

Based on the following observations, riboflavin biosynthesis in Bacillus is controlled by a single operon containing 5 genes: the β riboflavin synthase gene, ORF 2, ORF 3, ORF 4, and ORF 5, of which at least four, the β-riboflavin synthase gene, ORF 3, ORF 4 and ORF 5, unambiguously encode biosynthetic enzymes, with the remaining one, ORF 2, possibly encoding a biosynthetic enzyme.

1. ORF 3, ORF 4 and ORF 5 overlap restriction enzyme sites where insertion of cat-containing restriction fragments caused inactivation of riboflavin production in *B. subtilis* (FIGS. 4 and 8).

2. ORF 1 overlaps a restriction enzyme site(s) where insertion of cat-containing restriction fragments did not cause inactivation of riboflavin production in a rib$^+$ *B. subtilis* strain (Table III and FIG. 8), nor did it cause reduction of riboflavin production in the deregulated, RoF$^r$ *B. subtilis* strain RB52.

3. ORF 2 also overlaps a restriction enzyme site, EcoRV, where insertion of cat-containing restriction fragments did not cause inactivation of riboflavin production in a rib$^+$ *B. subtilis* strain (Table III and FIG. 8). However, such an insertion did cause a detectable reduction of riboflavin production in the deregulated, RoF$^r$ *B. subtilis* strain RB52, indicating that the mutated ORF 2 gene product was partially inactive for riboflavin production. The results suggest that ORF 2 does encode a rib-specific enzyme.

4. Two DNA sequences capable of forming stem-loop structures indicative of rho-independent transcriptional termination sites were identified within the intercistronic gaps between ORF 1 and ORF 2 and between ORF 5 and ORF 6 (FIGS. 4 and 9). Removal of structures between ORF5 and ORF6 enhances expression of riboflavin. The structures impart riboflavin sensitivity to lacZ-fusion constructs; thus, they can be used to impart such sensitivity to any other gene to which they are fused at the 5'-end upstream of the promoter.

5. A DNA sequence, TTGCGT-(17bp)-TATAAT, resembling the promoter recognized by the $\sigma^A$ (vegetative form) of *B. subtilis* RNA polymerase was identified approximately 290 bp upsteam from ORF 5, oriented in the same transcriptional direction as ORF 5 (FIG. 4). A transcriptional fusion of this promoter ($P_1$, on a 1.1 kb BglII-NcoI restriction fragment) to a promoterless *E. coli* lacZ gene ($P_1$-lacZ) displayed riboflavin-regulated expression of β-galactosidase activity in a rib$^+$, *B. subtilis* strain (62121) and high-level, constitutive (unregulated) expression of β-galactosidase activity in a rib$^+$, RoF$^r$ *B. subtilis* strain (RB52) only when the promoter was oriented in the same transcriptional direction as the gene, as shown in Table IV. Primer extension analysis was used to confirm the start site. Transcriptional and Northern analyses were used to show a polycistronic RNA of 4.2 kb encompasses the entire rib operon.

TABLE IV

RIBOFLAVIN-REGULATED EXPRESSION OF
$P_1$-LacZ TRANSCRIPTIONAL FUSIONS

| Strain (integrated plasmid) | β-Galactosidase Specific Activity (Miller Units) | |
| --- | --- | --- |
| | + Riboflavin (2 μg/ml) | − Riboflavin |
| *B. subtilis* 62121 ($P_1$-lacZ$^a$) | 1.3 | 4.2 |
| *B. subtilis* RB52 ($P_1$-lacZ$^a$) | 31 | 38 |
| *B. subtilis* 62121 ($P_1$-lacZ$^b$) | <0.1 | <0.1 |
| *B. subtilis* 62121 | <0.1 | <0.1 |

$^a$$P_1$ and lacZ oriented in the same direction
$^b$$P_1$ and lacZ oriented in opposite directions Based on these results, this $\sigma^A$ promoter, $P_1$, is a primary promoter for transcription of ORF 5, ORF 4, ORF 3, β-riboflavin synthase gene and ORF 2.

6. A second DNA sequence, TTGAAG-(17bp)-TACTAT, resembling a promoter recognized by the $\sigma^A$ (vegetative form) of *B. subtilis* RNA polymerase was identified within the 3' end of ORF 4, approximately 295 bp upstream from ORF 3 and oriented in the same transcriptional direction as ORF 3 (FIG. 4). Integration into *B. subtilis* by a Campbell-type recombination event of an *E. coli* plasmid containing this promoter sequence on a 0.7 kb SalI-BglII restriction fragment did not cause inactivation of riboflavin production in *B. subtilis*, results which indicated that this second sequence ($P_2$) has promoter activity and thus may actually control transcription (in addition to the $\sigma^A$ $P_1$, promoter) of ORF 3, the β subunit riboflavin synthase gene and ORF 2. LacZ fusions and Northern analysis confirmed the existence of this promoter.

7. A third DNA sequence, TTGAAT-(18bp)-TAAAAA, possibly resembling the promoter recognized by the $\sigma^A$ (vegetative form) of *B. subtilis* RNA polymerase was identified within the intercistronic region between the β subunit of the riboflavin synthase gene and ORF 2, approximately 83 bp upstream of ORF 2 and oriented in the same transcriptional direction (FIG. 4). This $\sigma^A$ promoter, $P_3$, may also control transcription of ORF 2, in addition to $P_1$ and $P_2$.

8. In vitro-coupled transcription/translation analysis of S-30 reactions of the cloned DNA confirmed that ORF 2, ORF 3, ORF 4, and ORF 5 all actually encoded proteins of the size predicted from their respective sequences.

9. Three of the five presumed enzymatic steps in riboflavin biosynthesis were assigned to specific coding regions by comparing predicted amino acid sequences or molecular weights of their products to published protein sequences, using GenBank®, or known protein sizes.

a. The putative protein encoded by the open reading frame between ORF 2 and ORF 3 almost identically matched the published 154 amino acid sequence of the β subunit for the riboflavin synthase enzyme (Ludwig et al., *J. Biol. Chem.* 262:1016, 1987). Only one amino acid difference was detected: lysine was substituted for glycine at residue 65. This enzyme is reported to catalyze the formation of 6,7-dimethyl-8-ribityllumazine from 5-amino-6-ribitylamino-2,4(1H,3H)-pyrimidinedione-5'-phosphate (FIG. 1, structures 5 and 4, respectively) and 3,4-dihydroxybutanone-4-phosphate.

b. A 39% identity in an 88-amino acid overlap was identified between the putative product of ORF5 and deoxycytidylate deaminase, a 188 amino acid protein encoded by the *E. coli* bacteriophage $T_2$ (Maley et al., *J. Biol. Chem.* 258:8290, 1983). Based on this result, ORF 5 most likely encodes the rib-specific deaminase that catalyzes the formation of 5-amino-6-(ribosylamino)-2,4(1H,3H)-pyrimidinedione-5'-phosphate from 2,5-diamino-6-(ribosylamino)-4(3H)-pyrimidinone-5-phosphate (FIG. 1, structures 3 and 2, respectively).

c. The predicted molecular weight of the ORF 4 gene product (26,000 Da) was in good agreement with the molecular weight of the α-subunit for riboflavin synthase (23,000 Da; Bacher et al., *J. Biol. Chem.* 255:632, 1980). Based on this result, ORF 4 encodes the α-subunit for riboflavin synthase, which catalyzes the final step of the biosynthetic pathway: dismutation of 6,7-dimethyl-8-ribityllumazine to riboflavin (FIG. 1, structures 5 and 6, respectively) and 5-amino-6-ribitylamino-2,4(1H,3H)-pyrimidinedione.

10. The remaining enzymatic steps in riboflavin synthesis were tentatively assigned to coding regions by aligning the position of ORFs to a physical map of rib mutations in the operon (Morozov et al., *Mol. Genet. Mik. Virusol.* no. 7:42 (1984)). Mutations for defective GTP cyclohydrolase were reported to map to the 0.5 kb HindIII fragment. Since ORF 3 encompasses this restriction fragment, we concluded that ORF 3, at least in part, encodes this enzymatic function, which catalyzes the formation of 2,5-diamino-6-(ribosylamino)-4(3H)-pyrimidinone-5'-phosphate from GTP (FIG. 1, structures 2 and 1, respectively). In addition, the biosynthetic gene encoding a rib-specific reductase was reported to be contained entirely within the approximately 1.8 kb HindIII fragment. Since this fragment contains only two complete coding regions, the β subunit of the riboflavin synthase gene and ORF 2, we speculate that ORF 2 encodes the reductase, which catalyzes the formation of 5-amino-6-(ribitylamino)-2,4(1H,3H)-pyrimidinedione-5'-phosphate from 5-amino-6-(ribosylamino)-2,4(1H,3H)-pyrimidinedione-5'-phosphate (FIG. 1, structures 4 and 3, respectively).

In addition, a similar rho-independent transcription termination site was detected in the apparent leader region of the operon, downstream of the putative $\sigma^A$ $P_1$ promoter but just upstream of the first coding region of the operon, ORF 5 (FIGS. 4 and 9). This potential terminator structure may be involved in regulation of the rib operon by a termination/anti-termination mechanism. In addition, a roseoflavin-resistant ($R_oF^R$) dependent regulatory region is present on a 0.7 kb SalI-BglII restriction fragment of ORF3.

Assignment of rib ORFs to Protein Products

One method for confirming whether the rib-specific ORFs encode proteins is to "visualize" the size and number of proteins synthesized from the cloned DNA in an S-30 in vitro coupled transcription/translation reaction using pRF2 and its various derivatives as templates. The S-30 fraction kit (New England Nuclear; used according to manufacturer's specifications) is especially efficient in translating *B. subtilis* genes due to the presence of their strong ribosome binding sites.

Using the cloned 10 kb EcoRI fragment of pRF2 or pRF4 as templates, we expected to detect five putative rib-specific proteins: β riboflavin synthase, 14.7 kilodaltons (kd) (Ludwig et al., *J. Biol. Chem.* 262:1016, 1987); and the proteins from ORF 2, 13.6 kd; ORF 3, 43.7 kd; ORF 4, 23 kd; and ORF 5, 39.7 kd. We also expected to detect at least two other proteins, encoded by ORF 6 (11.6 kd) and ORF 1 (at least 18.7 kd), as well as any additional proteins encoded by genes present in the unsequenced regions of the 10 kb cloned DNA fragment. In addition, vector-associated proteins, including the bla and cat antibiotic resistance gene products, were also expected (the tet gene is not strongly expressed in S-30 reactions).

Excluding the bla- and cat-specific proteins (32 kd and 18 kd, respectively) and other vector-associated proteins, a total of six major $^{35}$S-labelled proteins were detected, with molecular weights of 47 kd, 44 kd, 38 kd, 26 kd, 20 kd and 15 kd, on a 15%-SDS polyacrylamide gel of the S-30 reactions with pRF2 or pRF4. To assign these protein products to their corresponding rib-specific ORFs, S-30 reactions were repeated using various available deletion derivatives, cat-insertion derivatives, and subcloned fragments of the 10 kb EcoRI cloned DNA (FIG. 10). The results are shown in Table V.

TABLE V

RIB-SPECIFIC PROTEINS OBSERVED IN S-30 REACTIONS

| Plasmid | 47,000 Daltons (ORF 3) | 44,000 Daltons (ORF 5) | 26,000 Daltons (ORF 4) | 15,000 Daltons (ORF 2) |
|---|---|---|---|---|
| pRF2 | + | + | + | + |
| PRF4 | + | + | + | + |
| pRF21 | − | − | + | − |
| pRF5 | − | − | − | + |
| pRF29 | − | − | − | − |
| pRF12 | + | − | + | + |
| pRF10 | − | − | − | − |
| pRF38 | − | − | − | − |
| PRF24/pRF20 | − | + | + | + |
| pRF23 | + | − | + | + |

Based on these results, protein products were assigned to ORF 3 (47 kd); ORF 5 (44 kd); ORF 4 (26 kd); and ORF 2 (15 kd), with molecular weights in close agreement with the predicted sizes.

The assignment of products to ORF 2 and the β riboflavin synthase gene were less straightforward than the assignments to the other ORFs. Since the S-30 reaction of pRF2 produced a 15 kd protein which was close to the predicted size of the proteins encoded by either gene, it was first assumed that this protein band actually contained both protein species. However, the cat insertion into ORF 2 in plasmid pRF38 completely removed this protein band, replacing it with a much smaller protein of 6 kd, which is in close agreement with the predicted size of the truncated ORF 2. Based on these results, the 15 kd protein appears to be generated only by ORF 2. It is not clear why the β riboflavin synthase protein is not visualized on the gels of the S-30 reactions. Taken in total, however, the results confirmed the existence of five rib-specific coding regions: ORF 5, ORF 4, ORF 3, ORF 2 and the β riboflavin synthase gene.

In addition, ORF 1 appeared to encode a 38 kd protein, while no product was identified for ORF 6.

Regulatory Mechanisms of the rib Operon

In *B. subtilis*, a recurring pattern of gene organization and regulation for biosynthetic pathways has been observed by several investigators. The nucleotide sequences of the tryptophan biosynthetic pathway (Henner et al., *Gene* 34:169, 1984) and the de novo purine nucleotide pathway (Ebbole and Zalkin, *J. Biol. Chem.* 262:8274, 1987) of *B. subtilis* both contain clustered, overlapping genes transcribed as a polycistronic message and regulated at least in part by a novel transcription termination/anti-termination mechanism, involving a repressor protein which can be encoded by a gene unlinked to the biosynthetic operon (Zalkin and Ebbole, *J. Biol. Chem.* 263:1595, 1988). Since we found that the organization of the rib biosynthetic and regulatory genes is strikingly similar to those of the *B. subtilis* trp and pur pathways, we hypothesized that the rib operon might be regulated, at least in part, in a similar manner.

Briefly, the key characteristics of the transcription termination/anti-termination model include (Shimotsu et al., *J. Bacteriol.* 166:461, 1986): (i) the presence of a long 5' leader sequence that precedes the first gene in the operon; (ii) the presence in the RNA leader of two or more overlapping dyad symmetries that have the potential to form mutually exclusive RNA stem-loops, one structure functioning as a rho-independent transcription terminator and the other as an "anti-terminator" (blocking the formation of the rho-independent transcription terminator); (iii) under repressive conditions, the repressor protein, activated by the end product of the pathway, binds to the nascent mRNA at a site which prevents formation of the anti-terminator, thus allowing formation of the terminator which terminates transcription; (iv) under derepressive conditions, binding of the unactivated repressor is precluded, resulting in the formation of the anti-terminator causing read-through transcription into the coding region of the operon.

As discussed above, the most likely site for initiation of transcription in the rib operon is a $\sigma^A$ promoter, $P_1$, located about 290 bp upstream from the first gene in the operon. Preliminary analysis of the RNA leader sequence indicated that it contained most, if not all, of the structures required for regulation by the termination/anti-termination model. Within this region, a stem-loop structure followed by a string of thymidines resembling a rho-independent transcription terminator was identified approximately 50 bp upstream of ORF 5; this sequence has the potential to form a hairpin with a ΔG of −26 kcal/mol (FIG. 9). In addition, several potential stem-loop structures with ΔG's ranging from −13 to −16 kcal/mol were located within the rib 5' leader that could possibly qualify as the anti-terminator sequence.

In addition to the primary site for the initiation of transcription, usually located upstream from the first gene in the operon, there exist in some biosynthetic pathways secondary promoter sites located within the internal regions of the operon. The possibility of there being a second promoter site within the rib locus was also suggested by previous R-loop heteroduplex studies of the rib operon (Osina et al., *FEBS Letters* 196:75–78, 1986), showing two or more sites for the initiation of mRNA synthesis. Our preliminary analysis of the intercistronic gaps of the rib operon did not detect such secondary promoter sites. However, when this analysis was extended to all of the sequences within the operon, another $\sigma^A$ promoter, $P_2$, was identified within the 3' end of ORF 4, just downstream from the SalI restriction site (FIG. 4). Thus it is possible that the expression of ORF 2, ORF 3, and the β-subunit for riboflavin synthase is also under the control of this secondary promoter. In addition, a possible third $\sigma^A$ promoter, $P_3$, was identified just upstream of ORF 2. Therefore ORF 2 is possibly also under the control of this additional promoter.

The location of putative coding regions, promoters and transcription termination sites on the DNA sequence of the 5.5 kb *B. subtilis* rib-specific region is shown in Table VI.

TABLE VI

CODING REGIONS, PROMOTER, AND TRANSCRIPTION TERMINATION SITES OF THE *B. SUBTILIS* RIB OPERON

|  |  | bp Number[a] |
|---|---|---|
| Coding Regions | ORF 6 | 364–678 |
|  | ORF 5 | 1101–2183 |
|  | ORF 4 | 2197–2841 |
|  | ORF 3 | 2859–4052 |
|  | β riboflavin-synthase gene | 4088–4549 |
|  | ORF 2 | 4665–5036 |
|  | ORF 1 | 5567–5057[b] |
| $\delta^A$ Promoters | $P_1$ | 771–799 |
|  | $P_2$ | 2528–2556 |
|  | $P_3$ | 4545–4574 |
| rho-Independent Termination Sites | Upstream from 5' promoter | 708–748 |
|  | Within 5' leader RNA | 1034–1067 |
|  | At 3' end of rib operon | 5038–5090 |

[a] of FIG. 3.
[b] Coding region oriented in opposite direction.

EXAMPLE 8

Construction of vectors containing a modified rib operon

The above functional analysis of the rib operon of *Bacillus subtilis* for the first time delimiting the regulatory regions and open reading frames in the nucleotide sequence permits construction of new vectors which are useful for increasing the yield of riboflavin production. The knowledge of the location of the specific genes required for riboflavin biosynthesis, of the location of transcriptional control regions, and other relevant regions (e.g., RBS) in those genes allows changes in such regions to be made. There follow a few examples of such manipulations.

Construction of an integration plasmid with a rib operon on a smaller DNA fragment The integrating vector used to construct the riboflavin overproducing strain RB50::[pRF8] contains a 10 kb EcoRI fragment including the rib operon. Since the rib operon appears to occupy less than 6 kb of DNA a new integration vector was constructed (pRF40) containing the rib operon on a smaller DNA fragment. The smaller size of this clone allows higher amplification of rib genes resulting in higher yields of riboflavin.

Referring to FIG. 12, pRF40 was constructed from pRF36 which is a plasmid in which the 0.8 kb NcoI fragment of pRF2 is replaced with a cat gene. The rib operon is contained on a 6.5 kb XbaI-EcoRI fragment. This fragment was isolated and ligated to pUC19 (Yanisch-Perron et al., 33 *Gene* 103, 1985; available from New England Biolabs, Boston, Mass., and Bethesda Research Laboratories, Maryland) digested with XbaI and EcoRI. The ligated DNA was transformed into DH5α *E. coli* and plated onto LB plates containing 40 μg/ml X-gal and 50 μg/ml ampicillin. Analysis of miniprep DNA prepared from white colonies indicated that pRF39 contained the 6.5 kb XbaI-EcoRI fragment.

pRF39 was digested with EcoRI, treated with CIAP, and then ligated to a 1.6 kb EcoRI fragment containing the cat gene. The ligated DNA was then transformed into DH5α *E. coli* and appropriate colonies selected for plating onto LB+10 μg/ml chloramphenicol; two colonies were chloramphenicol-resistant. Analysis of miniprep DNA prepared from these colonies confirmed the presence of the cat gene. One of these plasmids is pRF40 (FIG. 14).

Construction of plasmids containing transcriptionally modified rib operon

As described above, it is useful to replace the promoter and operator regions of the riboflavin operon with promoters allowing constitutive expression of the riboflavin biosynthetic genes. Plasmids containing such constructs can then be used to produce bacterial strains which will produce increased levels of riboflavin. A few examples, not limiting in the invention, are provided below.

Referring to FIG. 13, the riboflavin promoter and regulatory region were removed and replaced with an SPO1 promoter. We took advantage of the BglII site located at position 1130 at the start of ORF3. Oligonucleotides were synthesized (RB5 and RB6, see FIG. 18) that recreated the DNA sequence 5' to the BglII site (the first few amino acids of ORF5 and the SD sequence) up to position 1058. Reconstruction of the 5'-end of the operon stopped before any of the proposed DNA regulatory structures (FIG. 13). At their 5' ends the oligonucleotides contained BamHI, NsiI, and EcoRI restriction sites, allowing for placement of various promoters 5' to the rib operon. Because of the various restrictions sites in the rib operon it was necessary to construct the operon with the new promoters in several steps, as follows.

A 1.4 kb SalI-BglII fragment was isolated from pRF36 (FIG. 13). This fragment was ligated with the two oligonucleotides and EcoRI-SalI-digested pUC19. The ligated mixture was then transformed into *E. coli* DH5α cells and plated onto LB containing 50 μg/ml ampicillin and 40 μg/ml X-gal. Minipreps were prepared from Ap$^r$ white colonies; one plasmid having the desired structure is pRF46 (FIG. 13).

pRF46 was digested with BamHI and SalI and the 1.4 kb fragment isolated. This fragment was ligated with the 400 bp EcoRI-BamHI fragment of pNH202 (pUC8 containing the SPO1-15 promoter, Lee and Pero, *J. Mol. Biol.*, 152:247–265, 1981) and pUC19 cut with SalI and EcoRI. The ligated DNA was then transformed in DH5α *E. coli*, which were plated onto LB+ampicillin+X-gal. Miniprep DNA was prepared from white colonies; and pRF48 had the desired structure (FIG. 13).

pRF48 was digested with EcoRI and SalI and the 1.8 kb fragment isolated. This fragment was ligated with the 4.0 kb XbaI-SalI fragment (containing the rest of the rib operon) from pRF2 and XbaI, EcoRI-cut pUC19. The ligated mixture was then transformed into *E. coli* DH5α cells which were plated on LB+ampicillin+X-gal. Miniprep DNA was prepared from white colonies; pRF49 had the desired structure, and supernatants from culture containing this plasmid was yellow, indicating riboflavin production (FIG. 13).

To place the cat gene in pRF49, to allow selection in *B. subtilis*, the plasmid was digested with XbaI and ligated to a 1.3 kb cat-containing XbaI fragment from pEcc4. The ligated DNA was transformed in *E. coli* DH5 cells. Hundreds of Ap$^r$ colonies resulted, and the colonies were patched onto plates containing LB+10 μg/ml chloromphenicol. Approximately 10% of the colonies grew on the chloramphenicol plates, indicating the presence of the cat gene. One cat-containing plasmid is called pRF50 (FIG. 14).

The above example shows placement of a new promoter upstream of ORF5. We found that it is also useful to place a promoter after P$_2$ between ORF3 and ORF4 in order to further increase riboflavin production. An example of such construction now follows.

Referring to FIGS. 14 and 15, to place a copy of the SPO1-15 promoter upstream of ORF3 we made use of the restriction sites adjacent to the ORF4-ORF3 junction. The ClaI site at position 2767 is located at the end of ORF4 and is unique in the rib operon. Another useful restriction site near the beginning of ORF3 is the DraI site at position 2892. Oligonucleotides were synthesized that recreated the sequence from the above-mentioned DraI site past the start of ORF3 and placed a unique BamHI site before the beginning of ORF3 (linkers P2-A and P2-B, FIG. 18). Another set of oligonucleotides recreated the sequence from the ClaI site past the end of ORF4 and placed an EcoRI site at that location (linkers P2-CII and P2-DII, FIG. 18). The SPO1-15 promoter, located on a EcoRI-BamHI fragment, was then be placed between the BamHI and EcoRI sites created by the oligonucleotides. The entire operon was put together with this additional SPO1-15 promoter as follows.

Referring to FIG. 15, the 750 bp SalI-BglII fragment containing the ORF4-ORF3 function was subcloned to pIC2OR (Marsh et al., *Gene* 32:481–485, 1984). The resulting plasmid, pRF57, was then digested with DraI and BglII, and the predicted 270 bp DraI-BglII fragment was isolated. This fragment and linkers P2-A and P2-B were ligated to pIC2OR cut with SalI and BglII. The linkers placed BamHI and SalI sites upstream of the 5' end of ORF3. (The SalI site was chosen for convenience since BglII and BamHI sites are compatible and will be removed later.) The ligation was transformed into *E. coli* DH5α cells. Plating onto LB medium+Amp and X-gal resulted in white colonies; pRF58 had the desired structure. The 330 bp BglII-SalI fragment from pRF58 was isolated and ligated with 3.3 kb BglII-XbaI fragment containing the 3'-end of the rib operon from pRF36 (FIG. 12) and pUC19 cut with XbaI and SalI. The ligated DNA was then transformed into *E. coli* DH5α cells, resulting in white colonies; pRF62 (FIG. 15) had the desired structure. For convenience, the 3.6 kb BamHI-XbaI fragment was isolated from pRF62 and subcloned into BamHI-, XbaI-cut pUC19 (pRF64, FIG. 15). This plasmid now contained the 3.6 kb 3'-end of the rib operon with an engineered BamHI site preceding ORF3.

To place the SPO1-15 promoter in front of the 3'-half of the rib operon containing the last three open reading frames, we digested pRF64 with EcoRI and BamHI and ligated it to a 400 bp EcoRI-BamHI fragment containing the SPO1-15 promoter. The ligated DNA was transformed into *E. coli* DH5 cells and miniprep DNA was prepared; pRF65 has the desired structure.

The SPO1-15 promoter was than engineered to place a ClaI site upstream of the promoter to reconstruct the end of ORF4. The EcoRI-BamHI fragment from pNH202 containing the SPO1-15 promoter was ligated with linkers P2-CII and P2-DII and pCI2OR-digested with BamHI and ClaI. The ligated DNA was then transformed into *E. coli* DH5α cells. White colonies resulted and miniprep analyses indicated that pRF63 had the desired structure. The 470 bp ClaI-BamHI fragment was isolated then from pRF63 and ligated to the 2 kb EcoRI-ClaI fragment from pRF49 containing the SPO1-15 promoter and the 5'-end of the rib operon and pRF64 (FIG. 15), containing the SPOL promoter and the 3'-end of the operon, digested with EcoRI and BamHI. The ligated DNA was then transformed into *E. coli* DH5α cells. Miniprep DNA was prepared; pRF66 had the desired structure. In addition, *E. coli* containing pRF66 produced small amounts of riboflavin on LB medium+ampicillin plates, confirming that the operon was still intact.

The last step was to ligate the cat gene into the unique XbaI sites of pRF66 as described above. The resulting plasmid, pRF69 (FIG. 15) contained the cat gene in the same direction as the rib operon.

To construct a plasmid containing the entire operon with the natural or wild-type ribP$_1$ promoter and the SPO1-15 promoter after ribP$_2$, the 6.3 kb EcoRI-BamHI fragment of pRF64, the 2.75 kb EcoRI-ClaI fragment of pRF36, and the 470 bp ClaI-BamHI fragment of pRF63 were ligated and tranformed into E. coli DH5α cells. About 50% of the Ap$^r$ colonies were yellow, indicating riboflavin production. Miniprep DNA was prepared from yellow colonies and pRF68 had the desired structure (FIG. 16). A cat gene was added to pRF68 at the XbaI site, as discussed above, to generate pRF71 (FIG. 16). This plasmid contained the cat gene in the same direction as the rib operon.

As another example of the construction of useful plasmids in this invention, there now follows an example in which one or more promoters can be introduced within the riboflavin operon without prior removal of existing DNA sequences.

As an example, a prototype modified operon was constructed in pRF78, which contains a single copy of the SPO1-15 promoter inserted within a 30 bp non-essential region located between ribP$_1$ and a putative rho-independent transcriptional termination site (FIG. 14), an inactivated ribP$_1$ promoter to prevent possible transcriptional interference of the SPO1-15 promoter, an active ribP$_2$ promoter, the five structural genes encoding rib biosynthetic enzymes, and approximately 1.5 kb of flanking DNA nucleotide sequences downstream from the end of the riboflavin operon.

Referring to FIG. 14, the 1.7 kb NcoI-PstI fragment of pRF2, a fragment that contains the 5' promoter region of the rib operon and flanking regions, was first subcloned into mp19, a derivative of the E. coli bacteriophage vector M13 (United States Biochemical Catalog, 60–61, 1987; available from New England Biolabs, Massachusetts). One recombinant phage, M1.7, was recovered and standard DNA sequence analysis of the promoter region revealed a spontaneous mutation of the −10 region of the ribP$_1$ promoter, a TA-to-CT change, which may inactivate the promoter. Single stranded DNA was prepared and annealed to a synthetically-generated 55 bp DNA oligomer (see FIG. 17), containing a combination of restriction enzymes sites, 5'-EcoRI-SmaI-BamHI-3', flanked on either side by additional sequences homologous to the DNA region upstream from ribP$_1$. Double-stranded DNA molecules were synthesized using standard site-directed mutagenesis (SDM) protocols. These DNA molecules were introduced into the E. coli host TG-1 (available from Amersham Corp. Illinois) by transfection to generate recombinant phage plaques. One recombinant phage was found to contain the desired modified DNA sequence, as determined by standard DNA sequence analysis.

The modified rib promoter region was then rejoined to the rib structural genes of the operon using a pair of unique NsiI restriction enzymes sites 750 bp apart that flank the ribP$_1$ region and surrounding sequences. Double-stranded DNA molecules of the phage recombinant were prepared, digested with NsiI, the 750 bp fragment isolated, and the fragment ligated to dephosphorylated, 8.7 kb NsiI fragment of pRF39ΔR1 (a plasmid derived from pRF39, FIG. 12, that contains the wild-type rib operon). The ligated DNA molecules were introduced into E. coli DH5α cells by transformation, selecting for ampicillin-resistance, which resulted in the recovery of an Ap$^r$ colony harboring the desired recombinant plasmid, pRF75.

The SPO1-15 promoter was next inserted upstream from ribP$_1$ by digesting pRF75 with a combination of EcoRI and BamHI enzymes, ligating the cut DNA to purified 400 bp EcoRI-BamHI SPO1-15-containing restriction fragment, and introducing the ligated DNA into E. coli DH5α cells by transformation, selecting for ampicillin-resistance. One Ap$^r$ colony was found to harbor the recombinant plasmid, pRF77, containing the desired SPO1-15-modified rib operon. A chloramphenicol-resistance gene, cat, on a 1.6 kb XbaI restriction fragment, was subsequently introduced into pRF77 at the unique XbaI site, generating plasmid pRF78 (FIG. 14).

This prototype operon was further modified to contain an active ribP$_1$ promoter, and/or a second copy of the SPO1-15 promoter introduced downstream from ribP$_2$ within a intercistronic region between the rib coding regions ORF3 and ORF4, as described above. For example, plasmid pRF88, containing a derivative of the modified rib operon in pRF78 with an active ribP$_1$ promoter (FIG. 14) was constructed by the same procedure described above, using a recombinant phage containing the wild-type ribP$_1$ promoter. In other examples, a second copy of the SPO1-15 promoter, located downstream from ribP$_2$, was inserted into the existing modified rib operon-containing plasmids pRF78 and pRF88 by removing the 2.0 kb BglII fragment of either plasmid DNA and inserting the 2.4 kb BglII fragment of pRF66, generating plasmids pRF81 and pRF89 respectively (FIG. 14).

Construction of Ade$^±$ RB50 strains

It is important to use strains of bacteria that require as few components to be added to a fermentation medium as possible. Such strains are cheaper to ferment in order to produce riboflavin. To this end, adenine revertants which contained amplified modified rib operons were constructed. These revertants may not be true revertants of pur-60, but rather include mutations at another site which suppresses the requirement for adenine. As discussed below they produce about 25% more riboflavin than the non-reverted strains. Examples of such constructions are now described.

Plasmids pRF8, pRF40, pRF50, pRF69, pRF71, pRF78, pRF81, pRF88 and pRF89 were each transformed into RB50 (a RoF$^r$, deregulated B. subtilis strain) selecting for chloramphonicol resistance (Cm$^r$). A resistant colony was chosen for each strain. Ade$^+$ revertants of each strain was isolated by growing bacteria in RMM1 broth containing 10 μg/ml adenosine, and plating samples of the cultures onto minimal agar plates. One colony from each Ade$^+$ strain was selected and the vector DNA was amplified by selecting colonies that grow on increasingly higher levels of chloramphenicol, to a maximum level of 60 μg/ml.

Second site Integration

As described above, it is important to amplify an engineered rib operon in the B. subtilis chromosome to achieve high titers of riboflavin. It is also important to ensure that the number of DNA copies of the rib operon within a chromosome are not limiting to riboflavin production. Further amplification of the rib operon can be achieved by integrating and amplifying copies of the rib operon at more than one site in the B. subtilis chromosome to further increase riboflavin yield. One example of how such second site integration can be achieved is described below.

The above described vectors have all relied upon the cat gene to select for integration at the site of the rib operon. In order to insert the rib genes at a second site, it is preferable to have a different antibiotic resistance gene for use at that second site. For example, a tetracycline-resistance (tet) from B. subtilis can be used (Perkins and Youngman, J. Bacteriol., 155:607–615, 1983). Such tet genes are well known to those of ordinary skill in the art and are readily available to such persons. In one such construction, for example, pRF78 (FIG.

14), which contains a modified version of the rib operon, the plasmid can be cut with XbaI and ligated to a 2.4 XbaI fragment containing the tet gene. The resulting plasmid contains the tet gene at the XbaI site and is called pRF85 as shown in FIG. 16.

A strain which is deleted for the entire rib operon and which has a tet gene integrated at a second site is required to cause integration of pRF85 at that site. One such site is the bpr gene encoding bacillopeptidase F, a minor non-essentiall extracellular protease. An *E. coli* plasmid containing the bpr gene, pKT2, (Sloma et al., *J. Bacteriol.*, 172:1470–1477, 1990) was digested with EcoRV. This EcoRV site is in the coding region of bpr. The DNA was then ligated to a 2.4 kb EcoRI fragment containing the tet gene that had been blunt-ended. The resulting plasmid (containing the tet gene at the EcoRV site of bpr) was called pKT2-tet. This DNA was linearized with EcoRI and then transformed into RB52, a strain deregulated for riboflavin synthesis. Tet$^r$ colonies resulted and one such colony was called RB54. The integrated tet gene at bpr will function as a homologous sequence for the integration of pRF85.

To ensure that the cloned riboflavin operon of pRF85 would be inserted at the second chromosomal site containing the tetracycline-resistance gene, a region containing the original riboflavin operon and flanking DNA, equalling that contained in pRF85, was deleted from the chromosome of RB54 by in vitro methods. Briefly, this involves first generating an *E. coli* recombinant plasmid where the cloned riboflavin operon and flanking regions between the NcoI and XbaI restriction sites are removed and replaced by a chloramphenicol-resistance gene, cat, that is expressed in *B. subtilis* bacteria. This plasmid is then used to delete the chromosomal riboflavin operon by transforming RF54 with linearized plasmid molecules and selecting for chloramphenicol resistant (Cm$^r$) bacteria. Cm$^r$ bacteria result from a recombinant event (marker-replacment) which replaces the wild-type rib genes with the deleted copy containing the cat gene.

Specifically, plasmid pRF34 (see example 6) was used to generate an *E. coli* plasmid containing an in vitro-generated riboflavin operon deletion. This plasmid is derived from pRF2 where the riboflavin operon is flanked on either end by two unique XbaI sites (one site located upstream from the 5'-end of the rib operon next to the deleted 0.8 kb NcoI fragment and the second site located approximately 1.6 kb downstream from the end of the operon) and a cat gene is inserted outside of this region. By digesting pRF34 with XbaI and ligating the cut DNA molecules under dilute DNA concentrations, a recombinant plasmid, pRF82, was recovered where a 7.2 kb region containing the riboflavin operon is removed and essentially replaced with the cat gene. Plasmid pRF82 was linearized by restriction enzyme digestion and the cut DNA used to remove the chromosomal riboflavin operon of RB54 by DNA transformation, selecting for Cm$^r$ bacteria, resulting in marker replacement. Cm$^r$ colonies were screened for riboflavin auxotrophy and one Rib$^-$Cm$^r$ colony, RB55, was recovered for further investigation.

Plasmid pRF85 was transformed into strain RB55, selecting for Rib$^+$. One Rib$^+$ transformant was chosen and called RB58. This strain has the rib operon integrated at bpr by homologous recombination between the tet$^r$ genes in the plasmid and the chromosome. A transducing lysate of RB58 was prepared using standard techniques, and it was used to transduce RB50::[pRF69], selecting for Tet$^r$. These resistant colonies were found to have the modified rib operon integrated at the site of the rib operon and at bpr. One such Tc$^r$ colony RB50:: [pRF69]$_{60}$:: [pRF85]$_{120}$Ade$^+$ was recovered for further study. The rib operon integrated at rib was amplified by selecting for colonies that grow in the presence of increasing levels of chloramphenicol as described above, and the second copy of the rib operon was amplified by selecting colonies that grow on increasing levels of tetracycline to 120 µg/ml.

EXAMPLE 9

Fermentative Production of Riboflavin

Evaluation of riboflavin-overproducing strains was conducted in Chemap 14-liter vessels in carbon-limited fed-batch fermentations, with riboflavin content measured by HPLC. Since enzymes encoded by the genes for riboflavin synthesis are rate-limiting, the rib genes, which were amplified, were maintained at high-copy number by the inclusion of 60 µg/ml chloramphenicol in the inoculum seed train, but not in the fermentor.

A culture of a riboflavin-overproducing strain such as *B. subtilis* RB50::[pRF69]$_{60}$Ade$^+$ was grown on Tryptose Blood Agar Base (TBAB Difco) containing 60 ug/ml of chloramphenicol (CAM). Colonies were transferred to 300 ml baffled flasks containing 25 ml of riboflavin minimal medium (RMM; containing sodium glutamate 2.0 g/l, Casamino acids (Difco) 0.2 g/l, Yeast extract (Difco) 0.2 g/l, KH$_2$PO$_4$ 6.0 g/l, K$_2$HPO$_4$ 14.0 g/l, (NH$_4$)$_2$SO$_4$ 2.0 g/l, sodium citrate 1.0 g/l, MgSO$_4$.7H$_2$O 0.2 g/l, glucose 15.0 g/l, pH 7.0) with 60 ug/ml CAM. The inoculated flasks were incubated by shaking at 250 rpm and 37° C. After 8 hours, sterile glycerol was added to a final concentration of 15% and 1 ml aliquots were stored at −80° C.

In order to initiate a fermentation a frozen vial of the appropriate strain, e.g., RB50::[pRF69]$_{60}$Ade$^+$ was thawed at 37° C. and transferred into a 300 ml baffled flask with 25 ml of RMM with 60 ug/ml CAM and shaken at 250 rpm and 37° C. After 8 hours, 6 ml of the growing culture was used to inoculate 300 ml of fermentation medium (see Table VII below) in a series of 2 liter transfer flasks. Each flask contained 300 ml of fermentation medium to which had been added 90 ml of 15% glucose. Chloramphemicol was added to a final concentration of 60 ug/ml. After incubation for 12 hours at 200 rpm on an shaker with a 2" diameter orbit at 37° C., the contents of each flask was transferred to 7 liters of fermentation medium in a 14 liter fermentation vessel.

During fermentation, the broth was continually monitored for pH and dissolved oxygen (DO$_2$). Off gas was continuously analyzed by quadrapole mass spectrometry and carbon dioxide evolution (CER) and oxygen uptake rates were recorded.

A comparison of several fermentations demonstrated the reproducibility of the control systems. The initial carbohydrate was exhausted from fermentation with RB50::[pRF8]$_{60}$ after 4 hours of growth, causing a rise in pH and a fall in CER. At that point, carbohydrate feeding was initiated and logarithmic growth resumed until DO$_2$ became limiting at 6 hours. The rate of carbohydrate feeding was computer-controlled to maintain the DO$_2$ between 10–20% of saturation throughout the remaining fermentation time.

Excess carbohydrate in the fermentors does lead to oxygen starvation and reduced riboflavin production. oxygen transfer limitations determine the duration of logarithmic growth, final cell density and the riboflavin production rate. To increase the oxygen transfer rate, Chemap fermentors were run at 1000 rpm with a head pressure of 0.6 atmospheres.

Supplementation of the medium carbohydrate feed with yeast extract led to an increase in riboflavin production as compared to media without supplementation (FIG. 11, open squares: RBF-14; Table VII). However, because of its high cost, the amount of yeast extract was systematically reduced by substituting less expensive, inorganic ingredients. Substitution of ammonium hydroxide for sodium hydroxide in pH control allowed a reduction of yeast extract in the feed and resulted in an increase in both cell mass and riboflavin titer (FIG. 11, closed squares: RBF-22; Table VII). Fermentation times were also reduced. In other fermentations, moreover, yeast extract was completely eliminated from the feed and replaced with a combination of inorganic salts of ammonium and phosphate, resulting in a further increase in riboflavin production and a reduction of process time (FIG. 11, open circles: RBF-23; Table VII).

The original RB50::[pRF8]$_{60}$ was auxotrophic for adenine because of its pur-60 mutation. When experiments were conducted to determine the minimum amount of adenosine required by the strain, in order to minimize its inhibition of earlier biosynthetic enzymes involved in the pathway leading to the riboflavin-precursor IMP (FIG. 2), RB50::[pRF8]$_{60}$ (and, in general, RB50 strains with a rib operon amplified within their chromosome) was found to be unstable in its adenosine requirement and prototrophic revertants (Ade$^+$) were produced at a fairly high frequency. In shake flasks, the Ade$^+$ revertants appeared to grow and produce riboflavin at least as well as the RB50::[pRF8]$_{60}$ parent. When evaluated in fermentors, the revertant, RB50::[pRF8]$_{60}$(Ade$^+$), did not require adenosine in the media formulation. More importantly, the revertant grew at a faster rate and produced 25% more riboflavin than its parent strain in less time. A titer of 5.4 g/l riboflavin was produced in 49 hours (FIG. 11, closed circles: RBF-29; Table VII). In additional fermentations, moreover, Hy Soy T was removed from the initial charge or medium and replaced with corn steep liquor, resulting in a further increase in riboflavin production to 6.3 g/l in 48 hours. (RBF-42, Table VII).

Under these fermentation conditions, further significant increases in riboflavin production were demonstrated using bacterial strains that contained engineered riboflavin operon DNA. Strains containing the wild-type riboflavin operon on a 6.5 kb EcoRI-XbaI restriction fragment, RB50::[pRF40]$_{60}$(Ade$^+$), produced 7.4 g/l of riboflavin in 48 hours. Moreover, strains containing a transcriptionally-modified rib operon where the ribP$_1$ promoter and regulatory region were replaced by the constitutive SPO1-15 promoter, RB50::[pRF50]$_{60}$ (Ade$^+$), produced 9.0 g/l of riboflavin in 48 hours. These results demonstrate that modification of the riboflavin operon through the removal of regulatory regions and/or through the introduction of stronger, constitutive exogenous promoters leads to increases in riboflavin titer.

TABLE VII

FERMENTATION COMPONENTS AND CONDITIONS

| Component | RBF-14 | RBF-22 | RBF-23 | RBF-29 | RBF-42 |
|---|---|---|---|---|---|
| Initial Charge (g/l) | | | | | |
| Glucose | 10.00 | 15.00 | 15.00 | 15.00 | 15.00 |
| Corn step liquor | — | — | — | — | 10.00 |
| Hy Soy T | 15.00 | 15.00 | 15.00 | 10.00 | — |
| Sodium glutamate | — | — | — | 5.00 | 5.00 |
| Amberex 500 | 15.00 | 15.00 | 20.00 | 20.00 | 20.00 |
| KH$_2$PO$_4$ | 5.00 | 5.00 | 7.50 | 7.50 | 7.50 |
| MgCl$_2$.6H$_2$O | 0.5 | 0.5 | 1.50 | 1.50 | 1.50 |
| MnSO$_4$ | 0.05 | 0.05 | 0.05 | 0.05 | 0.05 |
| Adenosine | 0.05 | 0.05 | 0.05 | — | — |
| MAZU DF37 | 2.50 | 2.50 | 2.50 | 2.50 | 2.50 |
| FeCl$_3$ | — | — | 0.025 | 0.02 | 0.02 |
| CaCl$_2$ | — | — | 0.50 | 0.50 | 0.50 |
| ZnSO$_4$ | — | — | 0.0005 | — | — |
| CuCl$_2$ | — | — | 0.001 | — | — |
| CoCl$_2$ | — | — | 0.0013 | — | — |
| Nutrient Feed (g/l) | | | | | |
| Amberex 500 | 160.00 | 120.00 | — | — | — |
| NH$_4$Cl | — | — | 7.50 | 7.50 | 7.50 |
| (NH$_4$)$_2$SO$_4$ | — | — | 7.50 | 7.50 | 7.50 |
| KH$_2$PO$_4$ | — | — | 15.00 | 15.00 | 15.50 |
| MgSO$_4$.7H$_2$O | — | — | 2.50 | 2.50 | 2.50 |
| DL-70 syrup (as DS) | 600.00 | 600.00 | 600.00 | 660.00 | 600.00 |
| pH Control Range | | | | | |
| 6.6 | H$_2$SO$_4$ | H$_2$SO$_4$ | H$_2$SO$_4$ | H$_2$SO$_4$ | H$_2$SO$_4$ |
| 6.5 | NaOH | NH$_4$OH | NH$_4$OH | NH$_4$OH | NH$_3$ |
| Conditions | | | | | |
| Air (vvm) | 1.0 | 1.5 | 1.5–2.0 | 1.5 | 1.50 |
| RPM | 1000.0 | 1000.0 | 1000.0 | 1000.0 | 1000.0 |
| Temp °C. | 37.0 | 37.0 | 37.0 | 37.0 | 37.0 |
| Pressure (bar) | 0.5 | 0.5 | 0.5–0.75 | 0.6 | 0.6 |
| Riboflavin (g/l) | 3.4 | 4.1 | 4.3 | 5.4 | 6.3 |
| | (64 hrs) | (56 hrs) | (53 hrs) | (49 hrs) | (48 hrs) |
| Dry Weight (g/l) | 33.6 | 36.0 | 36.8 | ND | 44.6 |

The kinetics of riboflavin production in the various fermentations were analyzed using the Luedeking-Piret model. In all cases, the specific productivity declined from the conclusion of the exponential growth phase to the end of fermentation. Also, it was clear that riboflavin production was growth-associated under the fermentation conditions used.

We have discovered that the yield of riboflavin can be increased by changing the fermentation components and conditions. The yield of riboflavin can be increased compared to those conditions described above using those fermentation components and conditions shown in Table VIII.

TABLE VIII

| | RBF 150 (g/liter) | RBF 184 (g/liter) |
|---|---|---|
| Initial Batch | | |
| Yeast Extract | 20 | 20 |
| Glucose | 25 | 25 |
| KH$_2$PO$_4$ | 7.5 | 7.5 |
| MgCl$_2$.H$_2$O | 1.5 | 1.5 |
| CaCl$_2$.2H$_2$O | 1.0 | 1.0 |
| MnSO$_4$ | 0.05 | 0.05 |
| FeCl$_3$.6H$_2$O | 0.025 | 0.025 |
| Mazu DF37C | 2.5 | 2.5 |
| Corn Steep Liquor | 10 | — |
| Sodium Glutamate | 5 | 5 |
| (NH$_4$)$_2$SO$_4$ | — | 0.3 |
| Feed Medium (3 liters total used) | | |
| Glucose | 583.3 | — |
| NaCitrate | 6.67 | 6.67 |
| KH$_2$PO$_4$ | 15 | 15 |
| Succinic Acid | 1.67 | 1.67 |
| MgSO$_4$.7H$_2$O | 1.67 | 1.67 |
| Corn Syrup Solids | — | 833 |

Briefly, in one such fermentation the starting material is 6.65 liters of batch medium and 0.35 liters of bacterial (RB50::[pRF50]$_{60}$Ade$^+$) inoculant. Oxygen levels are monitored with a Chemap polarographic dissolved oxygen electrode. Dissolved oxygen levels are maintained at 15%±5% by means of computer regulated addition of the feed medium. Total feed added is about 3.0 liters in 48–56 hours. Fermentation pH is maintained at 6.5±0.1 (using 1N $H_2SO_4$ and $NH_3$ gas), and fermenter pressure is maintained at 0.6 bars, temperature at 37° C., and air flow at 10.5 liters/min. Under these conditions, strain RB50::[pRF50]$_{60}$(Ade$^+$) produced 11.0 g/l riboflavin in 48 hours, which represents an improvement in production of approximately 20% compared to the previous fermentation conditions. An increase in riboflavin production was demonstrated (RBF150, Table VIII) using the bacterial strains RB50::[pRF69]$_{60}$(Ade$^+$) containing a transcriptionally-modified riboflavin operon containing two SPO1-15 promoters, one replacing ribP$_1$ and regulatory sequences, and a second inserted between ORF3 and ORF4. This strain produced 13.0–14.0 g/l riboflavin in 48 hours, and 15 g/l in 56 hours, demonstrating that increased transcription of the riboflavin operon using two strong exogeneous promoters increases production levels of riboflavin. Finally, a further increase in riboflavin production was demonstrated using the bacterial strain RB50::[pRF69]$_{60}$::[pRF85]$_{120}$Ade$^+$ containing two amplifiable rib loci as in Example 8. This strain was grown at pH 6.8 and 39° C. using the modified fermentation medium shown in Table VIII (RBF 184) and riboflavin was isolated.

Deposits of Microorganisms

Plasmid pRF69, and strains containing plasmids pRF50 and pRF78, as well as strain RB58 have been deposited with the American Type Culture Collection Rockville, Md. on the following dates, and have been assigned the following accession numbers.

| Material | Deposit Date | Accession Number |
|---|---|---|
| pRF69 | June 6, 1990 | 68338 |
| RB58 | May 30, 1990 | 55053 |
| pRF50 | May 30, 1990 | 68332 |
| pRF78 | May 30, 1990 | 68333 |

Bacillus subtilis strain RB50 was deposited with the Agricultural Research Culture Collection (NRRL), Peoria, Ill., under the Budapest Treaty on the International Recognition of the Deposit of Microorganisms for the Purposes of Patent Procedures, and was assigned accession number B 18502. Applicants' assignee, Hoffmann-LaRoche, acknowledges its responsibility to replace these cultures should they die before the end of the term of a patent issued hereon, 5 years after the last request for a culture, or 30 years, whichever is the longer, and its responsibility to notify the depository of the issuance of such a patent, at which time the deposits will be made available to the public with all restrictions imposed by the depositor on availability to the public irrevocably removed. Until that time the deposits will be made irrevocably available to the Commissioner of Patents under the terms of 37 C.F.R. §1–14 and 35 U.S.C. §112.

The present invention is not to be limited in scope by the microorganism deposited since the deposited embodiment is intended as a single illustration of one aspect of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosures of which are incorporated by reference in their entirety.

Other embodiments are within the following claims.

We claim:

1. A purified nucleic acid comprising a bacterial rib operon which includes a bacterial ORF3 structural gene and an exogenous promoter, said ORF3 structural gene being hybridizable to B. subtilis rib ORF3 and encoding a protein that has ORF3 activity, said promoter being positioned to transcribe said ORF3 structural gene.

2. A purified nucleic acid comprising a bacterial rib operon which includes a bacterial ORF5 structural gene and an exogenous promoter, said ORF5 structural gene being hybridizable to B. subtilis rib ORF5 and encoding a protein that has ORF5 activity, said promoter being positioned to transcribe said ORF5 structural gene.

3. The purified nucleic acid of claim 2, wherein said promoter is located 5' upstream of said ORF5, with no terminators intervening between said promoter and said ORF5.

4. The purified nucleic acid of claim 1 or claim 2 wherein said bacterial rib operon comprises at least three open reading frames selected from the group consisting of a first open reading frame which hybridizes with B. subtilis ORF2 and encodes a protein that has ORF2 activity, a second open reading frame which hybridizes with B. subtilis ORF3 and encodes a protein that has ORF3 activity, a third open reading frame which hybridizes with B. subtilis ORF4 and encodes a protein that has ORF4 activity, a fourth open reading frame which hybridizes with B. subtilis ORF5 and encodes a protein with ORF5 activity, and a fifth open reading frame which hybridizes with B. subtilis β-riboflavin synthase gene and encodes a protein that has β-riboflavin synthase activity, said purified nucleic acid comprising a promoter not naturally associated with said rib operon, said promoter being positioned to transcribe each of said bacterial rib operon open reading frames.

5. The purified nucleic acid of claim 1, wherein said purified nucleic acid is present on a plasmid selected from the group consisting of pRF69, pRF71, pRF81 and pRF89.

6. The purified nucleic acid of claim 2 wherein said purified nucleic acid is present on a plasmid selected from the group consisting of pRF50, pRF69, pRF78 pRF81, pRF85, and pRF89.

7. Purified nucleic acid comprising a bacterial rib operon which includes a bacterial ORF3 structural gene and an exogenous promoter, said ORF3 structural gene hybridizing to B. subtilis rib ORF3, said promoter being positioned to transcribe said ORF3 structural gene, said purified nucleic acid being present on a plasmid selected from the group consisting of pRF69, pRF71, pRF81, and pRF89.

8. Purified nucleic acid comprising a bacterial rib operon which includes a bacterial ORF5 structural gene and an exogenous promoter, said ORF5 structural gene hybridizing to B. subtilis rib ORF5, said promoter being positioned to transcribe said ORF5 structural gene, said purified nucleic acid being present on a plasmid selected from the group consisting of pRF50, pRF69, pRF78, pRF81, pRF85 and pRF89.

9. A bacterium comprising the purified nucleic acid of claim 1, 2, or 4.

10. A bacterium comprising the purified nucleic acid of claim 7 or 8.

11. A Bacillus subtilis strain RB50 as deposited with the NRRL and assigned accession number B 18502, strain RB58 as deposited with ATCC and assigned accession number 55053, or riboflavin-producing variants of either strain thereof.

12. A recombinant bacterium comprising an exogenously introduced nucleic acid sequence, which sequence comprises a bacterial ORF3 structural gene and an exogenous promoter, said promoter being positioned to transcribe said ORF3 structural gene, said ORF3 structural gene:

encoding an amino acid sequence that has ORF3 activity, hybridizing to *B. subtilis* rib ORF3; and being expressed by said recombinant bacterium such that the recombinant bacterium produces a riboflavin titre of at least 10 g/l when fermented using standard commercial batch and feed conditions.

13. A recombinant bacterium comprising an exogenously introduced nucleic acid sequence, which sequence comprises a bacterial ORF5 structural gene and an exogenous promoter, said promoter being positioned to transcribe said ORF5 structural gene, said ORF5 structural gene:

encoding an amino acid sequence with ORF5 activity, hybridizing to *B. subtilis* rib ORF5; and being expressed by said recombinant bacterium such that the recombinant bacterium produces at least 10 g/l of riboflavin when fermented using standard commercial batch and feed conditions.

14. The recombinant bacterium of claim 12 wherein said exogenously introduced nucleic acid sequence further comprises a bacterial ORF5 structural gene, said promoter being positioned to transcribe said ORF5 structural gene, said ORF5 structural gene being specifically hybridizable to *B. subtilis* rib ORF5 and being expressed by said bacterium.

15. The recombinant bacterium of claim 12 wherein said exogenously introduced nucleic acid sequence comprises a bacterial rib operon comprising at least three open reading frames selected from the group consisting of a first open reading frame which hybridizes with *B. subtilis* ORF2 and encodes a protein that has ORF2 activity, a second open reading frame which hybridizes with *B. subtilis* ORF3 and encodes a protein that has ORF3 activity, a third open reading frame which hybridizes with *B. subtilis* ORF4 and encodes a protein that has ORF4 activity, a fourth open reading frame which hybridizes with *B. subtilis* ORF5 and encodes a protein that has ORF5 activity, and a fifth open reading frame which hybridizes with the *B. subtilis* β-riboflavin synthase-encoding ORF and encodes a protein that has β-riboflavin synthase activity.

16. The recombinant bacterium of any one of claims 12–15 in which said exogenously introduced nucleic acid sequence is positioned in the chromosome of said recombinant bacterium.

17. The recombinant bacterium of claim 12, wherein said exogenous promoter is a first exogenous promoter, and said exogenously introduced nucleic acid sequence further comprises a ORF4 structural gene and a second exogenous promoter, a) said ORF4 structural gene being hybridizable with *B. subtilis* ORF4 and encoding a protein that has ORF4 activity, b) said second exogenous promoter being positioned to transcribe said ORF4 structural gene, and c) said first exogenous promoter being positioned between said ORF4 structural gene and said ORF3 structural gene to transcribe said ORF3 structural gene.

18. A recombinant bacterium comprising an exogenously introduced nucleic acid sequence comprising at least one bacterial rib operon open reading frame selected from the group consisting of a first open reading frame which hybridizes with *B. subtilis* ORF2 and encodes a protein that has ORF2 activity, a second open reading frame which hybridizes with *B. subtilis* ORF3 and encodes a protein that has ORF3 activity, a third open reading frame which hybridizes with *B. subtilis* ORF4 and encodes a protein that has ORF4 activity, a fourth open reading frame which hybridizes with *B. subtilis* ORF5 and encodes a protein that has ORF5 activity, and a fifth open reading frame which hybridizes with the *B. subtilis* β-riboflavin synthase-encoding ORF and encodes a protein that has β-riboflavin synthase activity, at least two copies of said exogenously introduced nucleic acid being positioned in the chromosome of said recombinant bacterium, said exogenously introduced nucleic acid is expressed by said recombinant bacterium such that riboflavin biosynthesis by the recombinant bacterium is increased relative to biosynthesis by a bacterium that is identical to said recombinant bacterium except for the absence of said exogenously introduced sequence, and the bacterium produces at least 10 g/l of riboflavin when fermented using standard commercial batch and feed conditions.

19. The recombinant bacterium of claim 18 wherein said bacterial rib operon is a Bacillus rib operon.

20. The recombinant bacterium of claim 18 wherein said exogenously introduced nucleic acid sequence comprises a bacterial rib operon of at least the following five open reading frames: a first open reading frame which hybridizes with *B. subtilis* ORF2 and encodes a protein that has ORF2 activity; a second open reading frame which hybridizes with *B. subtilis* ORF3 and encodes a protein that has ORF3 activity; a third open reading frame which hybridizes with *B. subtilis* ORF4 and encodes a protein that has ORF4 activity; a fourth open reading frame which hybridizes with the *B. subtilis* ORF5 and encodes a protein that has ORF5 activity; and a fifth open reading frame which hybridizes with the *B. subtilis* β-riboflavin synthase-encoding ORF and encodes a protein that has β-riboflavin synthase activity.

21. The recombinant bacterium of claim 18 which contains a second exogenously introduced nucleic acid sequence comprising at least one open reading frame selected from the group consisting of a first open reading frame which hybridizes with *B. subtilis* ORF2 and encodes a protein that has ORF2 activity, a second open reading frame which hybridizes with *B. subtilis* ORF3 and encodes a protein that has ORF3 activity, a third open reading frame which hybridizes with *B. subtilis* ORF4 and encodes a protein that has ORF4 activity, a fourth open reading frame which hybridizes with *B. subtilis* ORF5 and encodes a protein that has ORF5 activity, and a fifth open reading frame which hybridizes with the *B. subtilis* β-riboflavin synthase-encoding open reading frame and encodes a protein that has β-riboflavin synthase activity, said second exogenously introduced nucleic acid being positioned in the chromosome of said recombinant bacterium, said second exogenously introduced nucleic acid being expressed by said recombinant bacterium such that riboflavin biosynthesis by the bacterium is increased relative to a bacterium that is identical to said recombinant bacterium except for the absence of said second exogenously introduced nucleic acid sequence.

22. The recombinant bacterium of claim 21, wherein said first exogenously introduced nucleic acid is present in multiple copies at said first site, and said second exogenously introduced nucleic acid is present in multiple copies at said second site.

23. The recombinant bacterium of claim 22, wherein said first exogenously introduced nucleic acid is present in at least 5 copies at said first site, and said second exogenously introduced nucleic acid is present in at least 5 copies at said second site.

24. The recombinant bacterium of claim 18 further characterized in that said exogenously introduced nucleic acid comprises an exogenous promoter positioned to transcribe said open reading frame.

25. The recombinant bacterium of claim 24 wherein said promoter is positioned in an intercistronic region of one of said bacterial rib open reading frames.

26. The recombinant bacterium of claim 25, wherein said promoter is located between said ORF3 and said ORF4, in a region 5' upstream of ORF3.

27. The recombinant bacterium of claim 24, wherein said promoter is located 5' upstream of said ORF5, with no terminators intervening between said promoter and said ORF5.

28. The recombinant bacterium of claim 12, claim 13, or claim 24 wherein said promoter is a constitutive promoter.

29. The recombinant bacterium of claim 12, claim 13, or claim 24 wherein said promoter is an SPO1 promoter.

30. The recombinant bacterium of claim 12, claim 13, or claim 18 wherein a said exogenously introduced nucleic acid further comprises a ribosome binding site not naturally associated with a rib structural gene in said exogenously introduced nucleic acid.

31. The recombinant bacterium of claim 12, claim 13 or claim 18 wherein said host bacterium is resistant to a purine analog selected from the group consisting of: 8-azaguanine; decoyinine; and methionine sulfoxide.

32. The recombinant bacterium of claim 12, claim 13, or claim 18 in which said bacterium is resistant to roseoflavin.

33. The recombinant bacterium of claim 12, claim 13, or claim 18 wherein said bacterium is a gram positive bacterium.

34. The recombinant bacterium of claim 33 wherein said bacterium is a member of the genus Bacillus or Cornyebacterium.

35. The recombinant bacterium of claim 12, claim 13, or claim 18 wherein said bacterium is a gram negative bacterium.

36. The recombinant bacterium of claim 35 wherein said bacterium is a member of the genus Escherichia or Klebsiella.

37. The recombinant bacterium of claim 12, claim 13, or claim 18 in which each said bacterial rib operon open reading frame is a B. subtilis rib operon open reading frame.

38. The recombinant bacterium of claim 37 in which said bacterium is a Bacillus or an E. coli bacterium.

39. A recombinant bacterium comprising an exogenously introduced nucleic acid sequence, which sequence comprises a bacterial ORF3 structural gene and an exogenous promoter, said promoter being positioned to transcribe said ORF3 structural gene, said ORF3 structural gene:
    encoding an amino acid sequence that has ORF3 activity,
    hybridizing to B. subtilis rib ORF3 under conditions which do not permit hybridization of non-ORF3 DNA to B. subtilis rib ORF3; and
    being expressed by said recombinant bacterium such that the recombinant bacterium produces a riboflavin titre of at least 10 g/l when fermented using standard commercial batch and feed conditions.

40. A recombinant bacterium comprising an exogenously introduced nucleic acid sequence, which sequence comprises a bacterial ORF5 structural gene and an exogenous promoter, said promoter being positioned to transcribe said ORF5 structural gene, said ORF5 structural gene:
    encoding an amino acid sequence that has ORF5 activity
    hybridizing to B. subtilis rib ORF5 under conditions which do not permit hybridization of non-ORF5 DNA to B. subtilis rib ORF5; and
    being expressed by said recombinant bacterium such that the recombinant bacterium produces a riboflavin titre of at least 10 g/l when fermented using standard commercial batch and feed conditions.

41. A recombinant bacterium comprising an exogenously introduced nucleic acid sequence comprising at least one bacterial rib operon open reading frame selected from the group consisting of:
    a first open reading frame which hybridizes with B. subtilis ORF2 under conditions which do not permit hybridization of non-ORF2 DNA to B. subtilis rib ORF2 and which encodes a protein that has ORF2 activity,
    a second open reading frame which hybridizes with B. subtilis ORF3 under conditions which do not permit hybridization of non-ORF3 DNA to B. subtilis rib ORF3 and which encodes a protein that has ORF3 activity,
    a third open reading frame which hybridizes with B. subtilis ORF4 under conditions which do not permit hybridization of non-ORF4 DNA to B. subtilis rib ORF4 and which encodes a protein that has ORF4 activity,
    a fourth open reading frame which hybridizes with B. subtilis ORF5 under conditions which do not permit hybridization of non-ORF5 DNA to B. subtilis rib ORF5 and which encodes a protein that has ORF5 activity, and
    a fifth open reading frame which hybridizes with the B. subtilis β-riboflavin synthase-encoding ORF under conditions with do not permit hybridization to non-β-riboflavin synthase-encoding ORF and which encodes a protein that has β-riboflavin synthase activity,
    at least two copies of said exogenously introduced nucleic acid being positioned in the chromosome of said recombinant bacterium, said exogenously introduced nucleic acid being expressed by said recombinant bacterium such that riboflavin biosynthesis by the recombinant bacterium is increased relative to biosynthesis by a bacterium that is identical to said recombinant bacterium except for the absence of said exogenously introduced sequence, and the bacterium produces at least 10 g/l of riboflavin when fermented using standard commercial batch and feed conditions.

42. A recombinant bacterium comprising an exogenously introduced nucleic acid sequence comprising at least one bacterial rib operon open reading frame selected from the group consisting of a first open reading frame which is B. subtilis ORF2, a second open reading frame which is B. subtilis ORF3, a third open reading frame which is B. subtilis ORF4, a fourth open reading frame which is B. subtilis ORF5, and a fifth open reading frame which is B. subtilis β-riboflavin synthase-encoding ORF, at least two copies of said exogenously introduced nucleic acid being positioned at a first site in the chromosome of said recombinant bacterium,
    said bacterium further comprising a second exogenously introduced nucleic acid sequence comprising at least one open reading frame selected from the group consisting of a first open reading frame which is *B. subtilis* ORF2, a second open reading frame which is *B. subtilis* ORF3, a third open reading frame which is *B. subtilis* ORF4, a fourth open reading frame which is *B. subtilis* ORF5, and a fifth open reading frame which is the *B. subtilis* β-riboflavin synthase-encoding open reading frame, said second exogenously introduced nucleic acid being positioned at a second site in said chromosome, said first site being different from said second site, each of said first and said second exogenously introduced nucleic acids being expressed by said bacterium such that:

riboflavin biosynthesis by the bacterium is increased relative to a bacterium that is identical to said recombinant bacterium except for the absence of said first and said second exogenously introduced nucleic acid sequences, and the bacterium produces at least 10 g/l of riboflavin when fermented using standard commercial batch and feed conditions.

43. The recombinant bacterium of claim 42 in which said bacterium is a *B. subtilis* bacterium.

* * * * *